(12) United States Patent
Parvin et al.

(10) Patent No.: US 8,099,257 B2
(45) Date of Patent: Jan. 17, 2012

(54) BIOMETRIC QUALITY CONTROL PROCESS

(75) Inventors: Curtis Parvin, Chesterfield, MO (US); John Yundt-Pacheco, Fairview, TX (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 63 days.

(21) Appl. No.: 11/709,386

(22) Filed: Feb. 22, 2007

(65) Prior Publication Data

US 2007/0198213 A1 Aug. 23, 2007

Related U.S. Application Data

(63) Continuation-in-part of application No. 11/344,705, filed on Feb. 1, 2006, now Pat. No. 7,299,153, which is a continuation of application No. 10/227,183, filed on Aug. 23, 2002, now Pat. No. 7,050,933.

(60) Provisional application No. 60/314,923, filed on Aug. 24, 2001.

(51) Int. Cl.
*G06F 19/00* (2011.01)

(52) U.S. Cl. .......................................... 702/179; 702/84

(58) Field of Classification Search .................... 702/19, 702/21–25, 30–32, 81, 84, 179–181, 183; 436/8–19; 340/3.3, 3.32, 3.42–3.43
See application file for complete search history.

(56) References Cited

U.S. PATENT DOCUMENTS

| | | | | |
|---|---|---|---|---|
| 4,202,033 A | * | 5/1980 | Strobel | 436/183 |
| 5,633,166 A | * | 5/1997 | Westgard et al. | 436/8 |
| 5,937,364 A | * | 8/1999 | Westgard et al. | 702/83 |
| 5,941,820 A | * | 8/1999 | Zimmerman | 600/300 |
| 6,223,143 B1 | * | 4/2001 | Weinstock et al. | 703/17 |
| 7,299,153 B2 | * | 11/2007 | Parvin et al. | 702/179 |

FOREIGN PATENT DOCUMENTS

| | | |
|---|---|---|
| EP | 0 962 872 A2 | 12/1999 |
| WO | WO 97/42588 | 11/1997 |
| WO | WO 00/12968 | 3/2000 |

OTHER PUBLICATIONS

Cembrowski, G., et al., "Assessment of "Average Normals" Quality Control Procedures and Guidelines for Implementation," Am. J. Clin. Pathol. 81:492-499 (1984).

(Continued)

*Primary Examiner* — Bryan Bui
(74) *Attorney, Agent, or Firm* — Stinson Morrison Hecker LLP; Mark C. Young

(57) ABSTRACT

Systems and methods configured to guide and manage laboratory analytical process control operations. A Biometric quality control (QC) process application is configured to monitor bias and imprecision for each test, characterize patient population data distributions and compare, contrast, and correlate changes in patient data distributions to any change in QC data populations. The Biometric QC process monitors the analytical process using data collected from repetitive testing of quality control materials and patient data (test results). The QC process identifies the optimal combination of, for example, frequency of QC testing, number of QCs tested, and QC rules applied in order to minimize the expected number of unacceptable patient results produced due to any out-of-control error condition that might occur. A method of determining an optimum frequency for bracketing patient data into batches using a minimum number of quality control samples is also provided.

15 Claims, 37 Drawing Sheets

OTHER PUBLICATIONS

Cooper, "Quality Control Practices and Preferences in Today's Clinical Laboratory: A Report for Government Regulators, Decision Makers and Advisors," MLO, pp. 56-65 (Jun. 1997).

Crowder, 1989, "Design of Exponentially Weighted Moving Average Schemes," Journal of Quality Technology 21(3):155-162.

Fraser, C.G., 1999, "General strategies to set quality specifications for reliability performance characteristics," Scand. J. Clin. Lab. Invest. 59:487-490.

Howanitz et al., 1997, "Clinical laboratory quality control: a costly process now out of control," Clinica Chimica Acta 260:163-174.

Lucas and Crosier, 2000, "Fast Initial Response for CUSUM Quality-Control Schemes: Give Your CUSUM a Head Start," Technometrics 42(1):102-107.

Neubauer, 1997, "The EWMA control chart: Properties and comparison with other quality-control procedures by computer simulation," Clinical Chemistry 43(4): 594-601.

Ricos, et al., 1999, "Current databases on biological variation: pros, cons and progress," Scand. J. Clin. Lab. Invest. 59:491-500.

Tetrault and Steindel, 1995, "Daily Quality Control Exception Practices Data Analysis and Critique," Q-Probes: Short term studies of the laboratory's role in quality care. College of American Pathologists, pp. 1-17.

Westgard et al., 1981, "A Multi-Rule Shewhart Chart for Quality Control in Clinical Chemistry," Clin. Chem. 27(3):493-501.

Ye et al., 2000, "Performance Evaluation and Planning for Patient-Based Quality Control Procedures," Am. J. Clin. Pathol. 113:240-248.

\* cited by examiner

BIOMETRIC QUALITY CONTROL PROCESS

CROSS-REFERENCE TO RELATED APPLICATIONS

This application is a Continuation-in-Part of U.S. patent application Ser. No. 11/344,705, filed on Feb. 1, 2006 now U.S. Pat. No. 7,299,153, which is a Continuation of U.S. patent application Ser. No. 10/227,183, filed on Aug. 23, 2002, now issued as U.S. Pat. No. 7,050,933, which is a Continuation-in-Part of U.S. Provisional Patent Application Ser. No. 60/314,923, filed on Aug. 24, 2001, all which are specifically hereby incorporated herein by reference in their entireties for all purposes.

STATEMENT REGARDING FEDERALLY SPONSORED RESEARCH OR DEVELOPMENT

Not applicable.

BACKGROUND OF THE INVENTION

1. Field of the Invention

The present invention relates generally to processes for implementing Biometric Quality Control (QC), and more particularly to systems and methods for guiding and managing laboratory analytical process control operations.

Advances in laboratory technology have improved test performance beyond the ability of conventional process control systems to monitor performance effectively. The process control system used by most laboratories since the early 1980s is that of Westgard. (See, J. O. Westgard, P. L. Barry, M. R. Hunt: A Multi-Rule Shewhart Chart for Quality Control in Clinical Chemistry CLIN. CHEM. 27/3, 493-501, 1981). This system is based on a set of six core statistical rules, each having statistical power to detect random and systematic deviations from the norm.

In an effort to keep up with technology, Westgard evolved his core system with selection grids. These were quickly followed by power function graphs, Ops Specs charts, and QC Validator. Validator is software designed to recommend statistical rules based on analytical goals defined by the lab for each test. The latest version of Validator incorporates biological variation. Even with these improvements, the Westgard scheme continues to utilize a relatively complex statistical process control framework. This approach, often misapplied, results in frequent alarms normally judged false or unwarranted when compared to medical decision limits (medical relevance). There is no universally accepted alternative to Westgard. Labs must continue to use this system or to design and validate their own QC scheme in order to meet federal and accreditation requirements creating a patchwork of analytical process control schemes. While this patchwork generally results in acceptable outputs, it is marred by widely varying costs, inconsistent application and failed expectations. (See, Cooper William G., Quality control practices and preferences in today's clinical laboratory: A report for government regulators, decision makers and advisors, MLO, June 1997, pp. 57-65; Tetrault Gregory A., Steindel, Steven J., Daily Quality Control Exception Practices Data Analysis and Critique, CAP Q-Probe, 1994; and Howanitz Peter J., Tetrault Gregory A., Steindel Stephen J, Clinical Laboratory Quality Control: A Costly Process Now Out of Control). Labs have expressed both concern and frustration in journal articles, at public forums, in focus groups, to commercial sales representatives and through public commentary.

Laboratories around the world employ various schemes to control the analytical process. In the United States, the most common application is Westgard. Outside the US, applications range from prescriptive German RiliBAK rules to individualized applications and Westgard. European laboratories are generally more sophisticated in their approach employing biological variation and seeking standardization among laboratories.

Statistical rules for monitoring the analytical process, such as Westgard, can be used alone or in combination. If the rules are combined (multi-rule), then the power of error detection increases. Many labs may not understand how to apply the rules. Consequently, false error detection may frequently lead to test operator indifference. For example, a CAP Q-Probe study conducted in 1994 found that many laboratories respond to a QC error flag by merely repeating the control. No reasoned troubleshooting occurs unless the test operator is unsuccessful in getting the control value to fall within acceptable limits. Reasons for not immediately troubleshooting may include: easier to retest than troubleshoot, laziness, lack of knowledge, habit, and no accountability to troubleshoot correctly.

Rather than accept that some type of error might be present in the test system when a statistical flag occurs, labs may move immediately to some form of remedy rather than troubleshooting. The basic premise is that the statistical control system they use creates too many unwarranted errors so they automatically assume the error flag is false. The quickest remedy in this environment is to get the control value within range. To do so, some labs may repeat the control in hopes that the next value will be within limits (playing the odds), repeat with fresh control product, check or repeat calibration, or make up fresh reagent. Sometimes limited troubleshooting may be employed, including, for example, testing of assayed control materials to detect systematic error, looking at a history of control outliers, and calling the manufacturer for guidance or word of any national performance trends. Each of these actions is taken without any reasonable justification other than one of them usually corrects the error at least temporarily. Typically, the most common causes of QC error flags include random error, environmental conditions, control range too tight or incorrectly calculated, reagent (lot change, deterioration, contamination), control problems, calibration, sampling error, instrument malfunction, and poor maintenance.

Laboratory staff typically consider troubleshooting to be complex and often unguided. The production atmosphere of a typical lab and limited resources may contribute to a philosophy of avoiding troubleshooting unless absolutely necessary. The assumption follows that if troubleshooting could be focused, guided, or deemed necessary and productive, laboratory staff would engage in the effort. In general, it is desirable to make troubleshooting far easier by, for example, providing a QC system that identifies actionable error (i.e., eliminates false error detection), providing online troubleshooting advice, providing interactive online user groups so labs can exchange information readily, basing analytical process control on medical relevance limits (where appropriate), providing an analysis of the most frequently observed errors and determining the most likely cause of the error flag, providing instrument-specific troubleshooting guides, posting control stability claims and interlabs online, providing method group statistics, providing continuing education, and providing parallel lots for troubleshooting.

Another practice characteristic that is relevant to development of a Biometric model is when and at what frequency quality control materials are tested. Typically, controls are predominately tested at the beginning of each batch of patient specimens, e.g., in coagulation, hematology, immunoassay, and urinalysis, with possibly a little higher frequency of random placement in toxicology and special chemistry. General chemistry is one department where random placement of QC materials may often occur. While random placement of QC materials will detect some errors, such random placement is not a scientific approach to detecting errors and provides no quantified determination of when (in a stream of patient samples) such QC materials should be tested. Furthermore, random placement of QC materials provides no verifiable or calculated assurance of a level at which errors are being detected, or even whether errors are likely to be detected at all 2. Description of Related Art

BRIEF SUMMARY OF THE INVENTION

The present invention provides, in one aspect, systems and methods configured to guide and manage laboratory analytical process control operations. In certain aspects, the present invention provides a Biometric quality control (QC) process application configured to monitor bias and imprecision for each test, characterize patient population data distributions and compare, contrast, and correlate changes in patient data distributions to any change in QC data populations. The Biometric QC application of the present invention is also configured to provide alerts to an operator when actionable error is present and guide the operator in troubleshooting.

Routine quality control involves the periodic testing of QC samples in order to detect an out-of-control error condition that may have occurred at any point in time. An accurate assessment of a routine QC strategy must account for the interplay between the size of an out-of-control error condition, the subsequent risk of producing unacceptable patient results, the frequency of QC testing, and the chance of rejecting a QC rule when it is applied. In certain aspects, the Biometric QC application of the present invention considers the expected number of unacceptable patient results due to an out-of-control error condition as an important outcome measure for QC performance. The QC design strategy of the present invention identifies the optimal combination of frequency of QC testing, number of QCs tested, and QC rules applied in order to minimize the expected number of unacceptable patient results produced due to any out-of-control error condition that might occur.

The Biometric QC application of the present invention, in certain aspects, monitors the analytical process using data collected from repetitive testing of quality control materials and patient data (test results). Aspects and advantageous features of the present invention will be discussed herein using various terms such as "Biometric model", "model", "Biometric application", "application", "system", etc., and such terms are not intended to limit the invention in any manner. The Biometric model is the application and mathematical algorithms that underlie the processes of the present invention.

The Biometric model of the present invention, in one embodiment, includes several new statistical models and modifications to two previously published models for monitoring both QC and patient data; EWMA (Exponentially Weighted Moving Averages) and CUSUM (Cumulative Sums). Both of these models can be applied to population means and variances. EWMA, with modifications, is the primary mechanism to monitor both routine QC data and patient population data for mean and variance. CUSUM is provided as an alternative mechanism for those users who prefer CUSUM.

Using today's QC parlance, exceeding an EWMA (or CUSUM) QC limit will require troubleshooting and corrective action. To the contrary, if the patient data EWMA (or CUSUM) limit is exceeded, this is considered an actionable event leading to troubleshooting, corrective action, and confirmation testing. Violation of the EWMA (or CUSUM) for variance limits for routine QC constitutes an actionable error. Operators should investigate possible sources of random error.

Labs should perform confirmation testing after a Change Event occurs. Confirmation testing typically includes testing a replicate series of control materials to determine performance acceptability. A "Change Event" is defined as any event that has potential to affect the analytical process subsequent to the event. Change events include but are not limited to activities such as calibration, change of reagent lot, and any instrument maintenance (other than daily).

Labs should test control materials routinely, but the frequency and level (concentration) of QC to be tested for routine QC is customizable for each test. Customization is based on a novel simulation model that compares risk (e.g., defined as the number of patient test results containing unacceptable error out of the total population) to the frequency of QC testing. Both risk and QC frequency are based on the number and magnitude of actionable errors that occur for the test derived from the evaluation period, the uncertainty of measurement for each test, the estimated total error for each test, and biological variation where appropriate.

Advantageous features of certain aspects of the Biometric model of the present invention include:

The Biometric model is based on the probability of reporting a patient test result containing unacceptable error rather than the probability of run rejection.

The Biometric model recognizes and addresses the random on-going nature of testing.

The Biometric model uses EWMA (or CUSUM) as a primary monitor for both QC and patient data.

Time of day and day of the week are used to further characterize patient population data to calculate a z-score for use by the EWMA (or CUSUM) model.

Current truncation techniques often assume a Gaussian distribution and use symmetrical truncation. Truncation limits for patient data for each test are determined by simulation and may or may not be symmetrical.

Routine QC is preferably monitored by a single rule only. The 1ks rule is based on method performance and clinical or medical relevance rather than statistical error and is user-defined reflecting laboratory quality goals for a particular test.

Westgard rules (e.g., multi-rule) are not used.

The frequency of routine QC and which levels (concentration) of control to test are determined by modeling the risk of reporting patient test results containing unacceptable error for various combinations of control frequency and concentration.

The frequency and character of routine QC for each test is re-evaluated at regular intervals and adjustments made when necessary.

Confirmation testing is preferably required after actionable error is identified and resolved by troubleshooting and corrective action.

Confirmation testing is preferably required after a Change Event occurs.

The application is able to de-identify patient data so the data can be used without compromising patient privacy.

Troubleshooting may be aided by electronic versions or internet access to electronic versions of all instrument manuals that are keyword searchable.

The application is advantageously designed so that large hospital and laboratory organizations can install the Biometric model locally and manage an organization-wide database themselves, sharing selected information with the application.

The application is able to provide comparative performance indices based on:
- calibration curves
- assay temperature
- wavelength(s) required for the assay
- number of reagents dispensed
- clinical parameters
- method of analysis In certain aspects, the application advantageously tracks one or more of instrument calibrations, frequency of calibration, reagent lot changes, frequency of reagent changes, maintenance of instruments. Each of these parameters can contribute to analytical error.

In certain aspects, the frequency of routine QC and which concentrations (levels) of control to test are derived by simulation and determined by acceptable risk. Control confirmation testing is required whenever a Change Event occurs. Change Events include, for example, calibration, reagent lot change, maintenance other than daily maintenance, and a notified change in a test system (e.g., new antibody or reagent reformulation)

The application of the present invention includes several statistical process modules operating simultaneously in a dynamic analytical environment. These modules are advantageously designed to achieve optimum output of patient test results within prescribed quality limits.

According to one aspect of the invention, a system is provided that determines an optimal patient-based quality control strategy for a laboratory based on the laboratory's patient population, analytical processes, and laboratory utilization. The system, in one aspect, defines the optimal quality control strategy to be the strategy with the smallest expected number of bad results that are produced because of undesired changes in the analytical testing process. A patient-based quality control strategy requires specification of the patient result distribution truncation limits and the parameters for the statistical quality control rule. Therefore, the system determines values for these parameters that result in the smallest expected number of bad results. Estimation of the expected number of bad results that are produced due to an undesired change in the analytical testing process is preferably accomplished by computer simulation.

The system of the present invention typically requires 3 to 12 months of time and date-stamped patient data for each test. In one aspect, these data are used for three separate purposes. First, the data are used to estimate time trends in the patient results distribution. Second, the patient data are utilized in the computer simulations of the analytical testing process, rather than assuming some standard distribution for the patient data (such as the typically used normal distribution). Third, the data are used to establish truncation limits that will exclude a specified fraction (%) of each patient result distribution.

The system of the present invention recognizes that the distribution of patient data is not constant over time. Patient data vary (normal versus abnormal) during the day and between days. For example, the distribution is different on weekend days versus weekdays. The same holds true for holidays or days when certain patients, such as dialysis patients, are processed versus a normal weekday. Recognizing and allowing for hourly, daily and seasonal variations enables the system to use both normal and abnormal patient test results. In one aspect, the 3 to 12 months of time- and date-stamped patient data for each test are used to estimate time trends in the distribution of patient results throughout the 168 hours of a week by estimating a smoothed average and standard deviation of patient results for each hour of the week. The time-interval baseline is unique to each individual test and each individual laboratory.

The system of the present invention uses computer simulation to determine the fraction (%) of the patient-results distribution to truncate that produces the smallest expected number of bad results. The algorithm determines how much data should be truncated on either end of the distribution to minimize the standard deviation of the truncated population relative to the truncated sample size. Consequently, the truncation limits determined by the system are typically nonparametric. A mean and standard deviation are calculated for each truncated population (time-interval baseline). These statistics are used to normalize patient data.

The system, in one aspect, applies an exponentially weighted moving average (EWMA) quality control rule to the normalized patient data that fall within pre-determined truncation limits. The system uses computer simulation to determine the optimal parameters of the EWMA rule that result in the smallest expected number of bad results produced. Typically, data used with EWMA models are not normalized.

According to another aspect of the invention, the system includes a testing confirmation module configured to simultaneously assess the impact of a range of potential event-related random and/or systematic out-of-control error conditions on the risk of producing bad patient results. The confirmation testing model typically requires that two quality specifications be specified: the maximum tolerable false rejection rate for confirmation testing and the maximum tolerable risk for producing bad results due to any possible out-of-control error condition associated with the event. These two quality specifications are used to determine the values for three parameters: the number of control samples to test at each concentration level of control material and two rejection thresholds. In one aspect, the thresholds are numerically derived to be optimal in the sense that they meet the two quality specifications using the fewest number of control samples. One threshold is used to test primarily for systematic out-of-control error conditions and the other is used to test for random out-of-control error conditions (an increase in imprecision).

After an event occurs, control materials are tested in multiples of the number of concentrations of materials normally tested. The results obtained from testing the control materials are transformed to z-scores. For an assessment of systematic error, the z-scores are averaged and compared to the first threshold limit. For an assessment of random error, the standard deviation of the z-scores is computed and compared to the second threshold limit. If neither limit is exceeded, the analytical process is assumed to be within operating specifications. If either limit is exceeded, the analytical process is assumed to be outside operating specifications, which requires identification of root cause and corrective action. Corrective action is preferably followed by another cycle of confirmation testing.

According to yet another aspect of the present invention, a system relies on input from the patient-based QC module and the confirmation testing module contained within the larger process. Based on inputs from these modules, the system recommends an appropriate, test-specific, routine QC testing strategy that produces the lowest expected number of bad patient test results due to undetected and undesired changes in the analytical process.

In one aspect, the system includes an algorithm that addresses test stability/instability, imprecision, frequency of error signals over time, and risk of producing a bad result. These inputs allow the algorithm to produce a test specific routine QC strategy that specifies the appropriate frequency of testing QC materials and the number of materials to be tested at each point in the analytical process.

In another aspect of the present invention, a method of determining an optimum frequency of bracketing patient sample data for a given QC Rule includes multiplying the probability of producing unacceptable results due to the presence of an out-of-control condition ($P_E$) by the average number of patient results reported during the undetected error condition ($ANP_{reported}$) to determine the number of unacceptable results reported $E(N_U)$. Given the probability of detecting an error ($P_{ed}$), the $ANP_{reported}$ is calculated by multiplying $(1-P_{ed}) \cdot (1/P_{ed}-\frac{1}{2}) \cdot E(N_B)$ for a given batch size $E(N_B)$. Multiplying $P_E \cdot (1-P_{ed}) \cdot (1/P_{ed}-\frac{1}{2})$ results in the average run length of unacceptable errors reported, or $ARL_U$. The number of unacceptable results reported $E(N_U)$ for a given batch size $E(N_B)$ is then calculated from $E(N_U)=ARL_U \cdot E(N_B)$ An optimum batch size for a given $E(N_U)$ can thus be calculated from $E(N_B)=E(N_U)/ARL_U$. A QC system is tested on patient samples at a frequency corresponding to the calculated batch size using a minimum number of QC samples.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 13 is the product of FIGS. 11 and 12.

DETAILED DESCRIPTION OF EXEMPLARY EMBODIMENTS

Definitions for various terms as used herein can be found at the glossary section at the end of this section in Appendix B.

Figure 1:
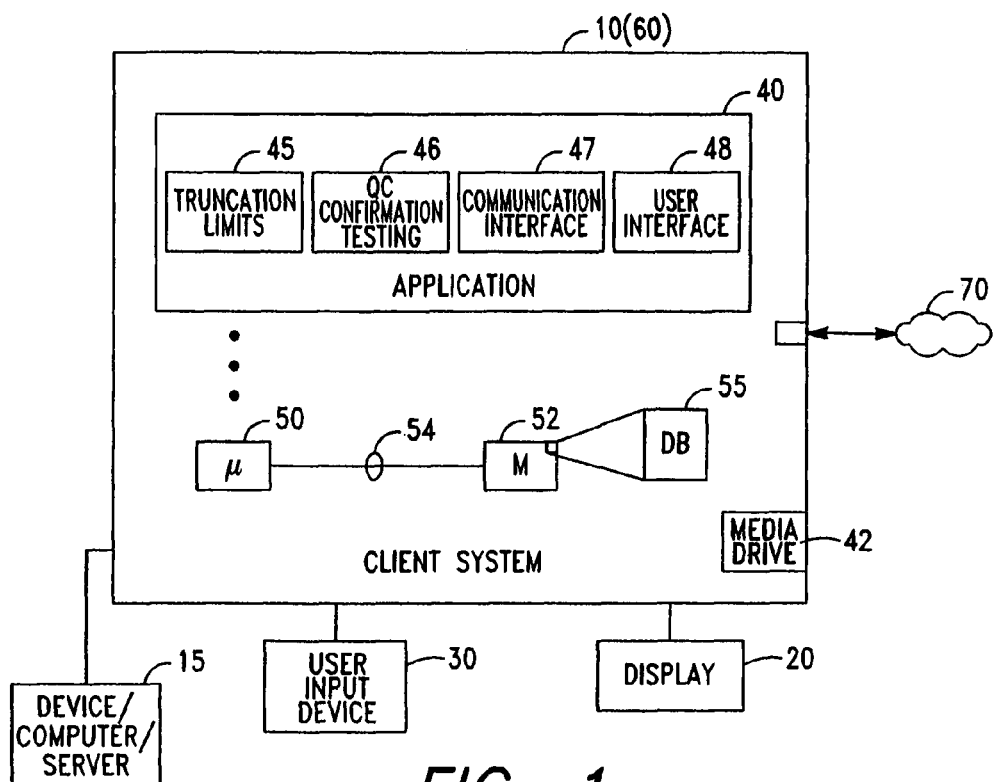
FIG. 1 illustrates a client computer system configured with a Biometric QC application module according to the present invention.
Figure 2:
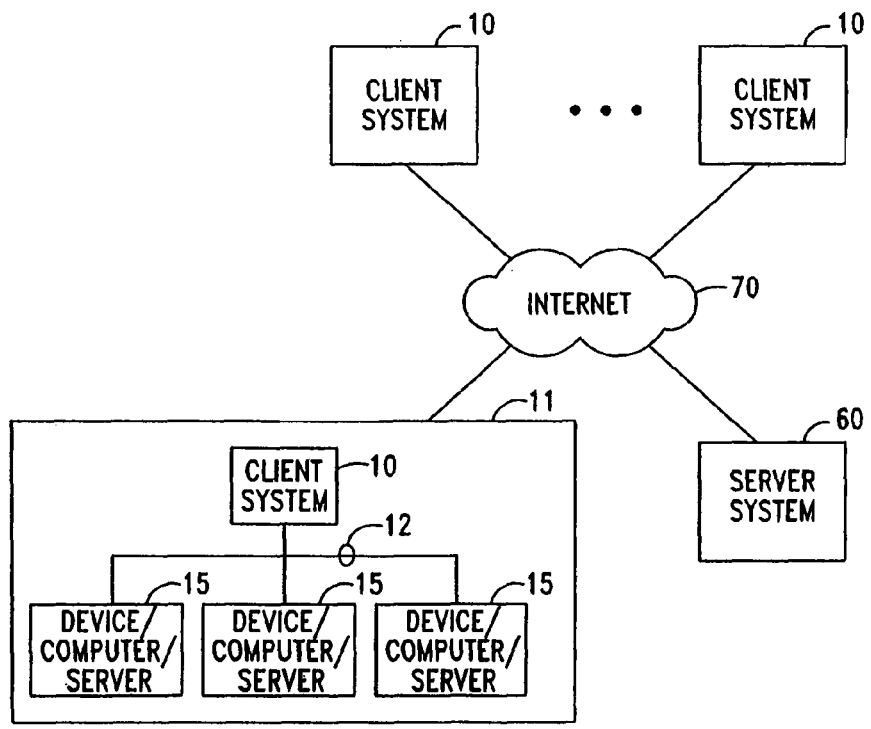
FIG. 2 illustrates a network arrangement for executing a shared application and/or communicating data and commands between multiple computing systems and devices according to another embodiment of the present invention.

FIG. 1 illustrates a client computer system 10 configured with a Biometric QC application module 40 (also referred to herein as, for example, "Biometric QC application" or "Biometric QC module") according to the present invention. FIG. 2 illustrates a network arrangement for executing a shared application and/or communicating data and commands between multiple computing systems and devices according to another embodiment of the present invention. Client computer system 10 may operate as a stand-alone system or it may be connected to server 60 and/or other client systems 10 and devices 15 over a network 70.

Several elements in the system shown in FIGS. 1 and 2 include conventional, well-known elements that need not be explained in detail here. For example, a client system 10 could include a desktop personal computer, workstation, laptop, or any other computing device capable of executing Biometric QC module 40. In client-server or networked embodiments, a client system 10 is configured to interface directly or indirectly with server 60, e.g., over a network 70, such as a LAN, WAN, the Internet, etc., and/or directly or indirectly with one or more other client systems 10 and devices 15, e.g., over network 70. Client system 10 typically runs a browsing program, such as Microsoft's Internet Explorer, Netscape Navigator, Opera or the like, allowing a user of client system 10 to access, process and view information and pages available to it from server system 60 or other server systems over Internet 70. Client system 10 also typically includes one or more user interface devices 30, such as a keyboard, a mouse, touchscreen, pen or the like, for interacting with a graphical user interface (GUI) provided on a display 20 (e.g., monitor screen, LCD display, etc.).

In one embodiment, Biometric QC application module 40 executes entirely on client system 10 (e.g., stand alone), however, in some embodiments the present invention is suitable for use in networked environments, e.g., client-server, peer-peer, or multi-computer networked environments where portions of code may be executed on different portions of the network system or where data and commands (e.g., Active X control commands) are exchanged. In local network embodiments, interconnection via a LAN is preferred, however, it should be understood that other networks can be used, such as the Internet or any intranet, extranet, virtual private network (VPN), non-TCP/IP based network, LAN or WAN or the like. For example, in FIG. 2, a LAN 12 interconnects multiple devices to a client system 10. Such a network is exemplary of a laboratory or hospital environment 11 where multiple instruments are connected to a system 10 (e.g., LIS). LAN 12 may include wireless and wired links and nodes, and use various communication protocols as are well known.

In preferred aspects, server 60 acts as a central computer system that executes a majority, or all, of the Biometric QC module code, and each client system 10 acts as a terminal or log-in point for a user. For example, client system 10 may reside in a laboratory or a hospital environment 11 (e.g., part of a LIS) and server 60 may reside in a remote location, e.g., geographically remote. In such a configuration, Biometric QC processing code is preferably executed entirely on server 60, with data and commands sent between client system 10 over network 70. For example, if client system 10 resides in a laboratory, client system 10 would provide the required data (e.g., patient test results/data, and other information from a local database and local instruments and devices) for processing by server 60, which would then provide processing results back to client system 10, or other computer system. It should be appreciated that the Biometric QC application code may execute entirely on a single system or portions may execute on both systems 10 and 60 (or on multiple systems in other embodiments) as desired for computational efficiency purposes. Additionally, a client system 10 in environment 11 may execute a portion or all of the Biometric QC processing code.

Returning to FIG. 1, according to one embodiment, client system 10 (or server 60) and some or all of its components are operator configurable using a Biometric QC module 40, which includes computer code executable using a central processing unit 50 such as an Intel Pentium processor or the like coupled to other components over one or more busses 54 as is well known. Computer code including instructions for operating and configuring client system 10 (or server 60) to process data content, monitor and control QC processes, and render GUI images as described herein is preferably stored on a hard disk, but the entire program code, or portions thereof, may also be stored in any other volatile or non-volatile memory medium or device as is well known, such as a ROM or RAM, or provided on any media capable of storing program code, such as a compact disk (CD) medium, digital versatile disk (DVD) medium, a floppy disk, and the like. An appropriate media drive 42 is provided for receiving and reading documents, data and code from such a computer-readable medium. Additionally, the entire program code of module 40, or portions thereof, or related commands such as Active X commands, may be transmitted and downloaded from a software source, e.g., from server system 60 to client system 10 or from another server system or computing device to client system 10 over the Internet as is well known, or transmitted over any other conventional network connection (e.g., extranet, VPN, LAN, etc.) using any communication medium and protocols (e.g., TCP/IP, HTTP, HTTPS, Ethernet, etc.) as are well known. It should be understood that computer code for implementing aspects of the present invention can be implemented in a variety of coding languages such as C, C++, Java, Visual Basic, and others, or any scripting language, such as VBScript, JavaScript, Perl or markup languages such as XML, that can be executed on client system 10 and/or in a client server or networked arrangement. In addition, a variety of languages can be used in the external and internal storage of data, e.g., patient results, device and instrument information (e.g., IDs, date/time stamps, calibration information, temperature information, etc.), and other information, according to aspects of the present invention.

According to one embodiment, Biometric QC application module 40 includes instructions for monitoring and controlling QC processes, as well as providing user interface configuration capabilities, as described herein. Application 40 is preferably downloaded and stored in a hard drive 52 (or other memory such as a local or attached RAM or ROM), although application module 40 can be provided on any software storage medium such as a floppy disk, CD, DVD, etc. as discussed above. In one embodiment, application module 40 includes various software modules for processing data content. For example, a communication interface module 47 is provided for communicating text and data to a display driver for rendering images (e.g., GUI images) on display 20, and for communicating with devices 15 and/or another computer or server system in network embodiments. A user interface module 48 is provided for receiving user input signals from user input device 30. Communication interface module 47 preferably includes a browser application, which may be the same browser as the default browser configured on client system 10, or it may be different. Alternatively, interface module 47 includes the functionality to interface with a browser application executing on client 20.

Application module 40 also includes a truncation limits module 45 including instructions to process patient data to determine truncation limits, and a QC Confirmation testing module 46 including instructions to determine optimal QC rule(s) as will be discussed in more detail below. Compiled statistics (e.g., device and instrument information), patient information, and other information are preferably stored in database 55, which may reside in memory 52, in a memory card or other memory or storage system such as an attached storage subsystem (e.g., RAID), for retrieval by truncation limits module 45, confirmation testing module 46, and other parts of Biometric QC application module 40. It should be appreciated that application module 40, or portions thereof, as well as appropriate data can be downloaded to and executed on client system 10.

Figure 3:
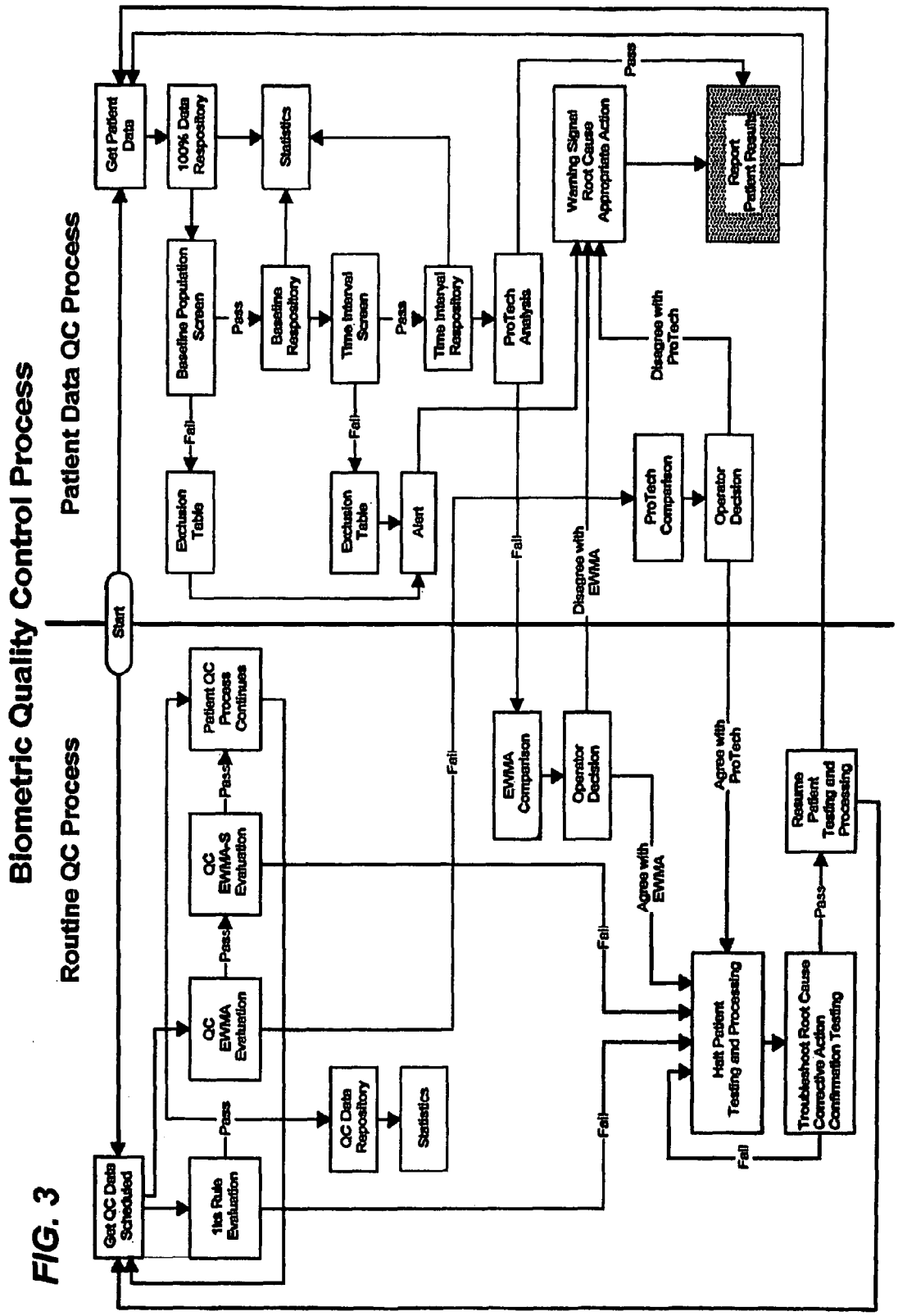
FIG. 3 illustrates a general overview of a QC process implemented by the Biometric QC application according to one embodiment.

FIG. 3 illustrates a general overview of a QC process implemented by Biometric QC application 40 according to one embodiment. The process of FIG. 3 is useful for monitoring instrument and test data and identifying the need for instrument maintenance or calibration. In preferred aspects, a QC model and a patient-based data model are used to quantify the reliability of the testing platform. Preferably the two models are based on EWMA protocols, however, CUSUM may also be used. For example, in one embodiment, routine QC testing is monitored by a single rule based on laboratory quality goals. Preferably a 1ks rule (e.g., 13s rule) using a standard Shewhart (Levey-Jennings) chart, or a mean/SD rule using a normalized scale, is used. The patient based model allows the system to identify the source of a shift in performance of an instrument or device. Shifts in performance are a common problem in laboratories and may be based on a variety of factors including for example, an artifact of the control product, instrument malfunction and reagent impurity.

In one embodiment, the system generates out-of-control error flags, and if troubleshooting verifies that an error exists, corrective action takes place. For example, corrective action may include calibration, maintenance, reagent change, etc. Corrective action constitutes an "event" that triggers a statistical model which determines what control levels need to be tested and in what quantity (i.e., how many replicates) to verify corrective action and troubleshooting was effective. The system also determines the frequency of quality control testing and the levels to be tested, based on, for example, unplanned maintenance, precision, bias, unplanned reagent changes, unplanned calibrations and unplanned use of fresh controls. Bias and precision for each instrument is preferably continuously monitored by the system.

EWMA, used in one embodiment to track patient data for maintenance/calibration, is also used as an error detection mechanism. In one embodiment, the system is sensitized to specific patient data populations, and patient data is filtered, e.g., truncated.

Returning to FIG. 3, a general description of one embodiment of a biometric model according to the present invention will be given. As shown, the routine QC and patient data-based QC processes run simultaneously and in parallel. The biometric model requires configuration prior to use. In a first configuration step, parameters are set for the frequency and character (e.g., number of QC test samples) of routine QC testing for each test (e.g., analyte). In a second configuration step, the QC rule (e.g., 1ks rule) is set for monitoring data generated by the routine QC process for each test. Another configuration step includes optimizing the QC rule (e.g., EWMA model) for monitoring data generated by routine QC testing for each test. Also, the QC rule (e.g., EWMA model) is optimized for monitoring variance of data generated by routine QC testing for each test. Another configuration step includes establishing a patient data QC protocol for each test, e.g., by truncating time-interval patient data and determining a mean and standard deviation of the remaining data population by hour of day and day of week. The QC rule (e.g., EWMA) is then optimized for accepting normalized patient data to monitor the analytical process for each test. Another configuration step includes setting parameters for confirmation testing for each test.

After the model is installed equilibration of the model is performed, e.g., by operating the model on new data for a period of time making adjustments to set parameters as appropriate. During operation of the model, QC materials are routinely tested for each test as required by the model. For example, a 1ks rule is used in one aspect. If the 1ks rule test fails, patient testing is halted, a root cause is established and/or corrective action is taken. Confirmation testing is performed, and patient testing resumes if confirmation testing passes. In another aspect, an EWMA rule is also applied to the routine QC data. If the EWMA rule fails, patient testing is halted, a root cause is established and/or corrective action is taken. In another aspect, an EWMA test for variance is applied to the data. If the EWMA variance test fails, patient testing is halted, a root cause is established and/or corrective action is taken.

On the patient QC side, patient data is normalized for each test according to the hour of day and day of week. An optimized EWMA model is then applied to the normalized data. If the EWMA model triggers an error signal, patient sample testing is halted and routine QC is performed as above. Whenever a defined event (e.g., change event) occurs during the course of a day, confirmation testing is performed. Additional and alternative aspects and features of the biometric QC process shown in FIG. 3 will be described herein and in Appendix A.

Appendix A provides and discusses additional aspects and embodiments of the present invention. It should be appreciated that the various "features" presented in Appendix A should not be taken as limiting, but rather, the various "features" as set forth in Appendix A are intended to teach and illustrate similar, additional and/or alternative aspects and embodiments to the embodiments and aspects discussed herein.

Truncation Limits Module

According to one embodiment of the present invention, the Biometric QC application module 40 includes a module 45 configured to determine truncation limits for a patient population. In preferred aspects, truncation module 45 determines truncation limits using the following general steps (which are each described in more detail below):

1. Collect all patient results over a given period of time. For example, a minimum of 91 days worth of data is useful, but one year's worth of data or more is preferable.

2. Determine patient-result truncation limits. Patient-result truncation limits are preferably determined when setting up a laboratory and when there is a significant change in the system. Examples of significant changes include a change in the population the laboratory services, a change in a reagent formulation, or an observed change in the distribution of results. Determining truncation limits typically assumes that the percentage of the patient population to exclude has been determined (see step 4). Two preferred processes for determining truncation limits include 1) determining truncation limits equidistant from the median of the un-truncated population, and 2) determining truncation limits that maximize the decrease in the standard deviation of the truncated population relative to the number of samples that are truncated (i.e., removed from the database). The second methodology is preferred, but the two methods may give similar results in many cases. In one embodiment, the second methodology is used as the primary process for determining truncation limits and the first methodology is used as a "sanity" check.

3. For each hour of the week, calculate the mean and the standard deviation of the truncated patient results.

4. Determine the optimal percentage of patient results to truncate for each analyte. It should be understood that although the steps are discussed in a given order, the steps are not necessarily performed in the order given. For example, Step number 4 is preferably performed before Step number 2.

Collect all Patient Results Over a Given Time Period

The patient results preferably contain complete days and complete weeks of data so that when the simulation "wraps," it wraps to the correct hour and the correct day of the week. In certain aspects, for each patient result, the minimum information required includes:

A unique instrument identifier (ID);

The date and time the instrument performed the result, e.g., date/time stamp;

The minimum and/or maximum reportable results for the analyte (e.g., any result less than the minimum is reported with a "<" and any result above the maximum is reported with a ">"); and The number of significant digits (nsd) to which patient results are rounded (e.g., 1, 0.1, 0.01, etc.).

Unique Instrument ID

An identifier or other information uniquely identifying the instrument from which the data is preferably provided. If multiple instruments of the same type are used, they can be treated as a single instrument if they all process similar patient samples. However if one instrument is used for stat requests and another for routine requests, or if one serves outpatient testing and another serves emergency department patients, etc., then the patient results for each instrument are preferably analyzed separately.

Date/Time Stamp

Most laboratory systems capture and store many different date/time stamps. Preferably, the date/time stamp associated with the time the instrument actually performed the test is provided to the system. However, the date/time stamp associated with when the test was ordered, when the sample was collected, when the sample was received in the lab, or when the result was verified, may be used. If the date/time the instrument performed the test is not available, the next best date/time is the one that comes closest to approximating the correct time order the results were tested on the instrument.

In labs that autoverify results, result verification dates and times may not be a good choice. Results that fail autoverification (which tend to be "abnormal" results) may include delayed verification times relative to results that pass autoverification, messing up the time order of the results in a way that is correlated with the magnitude of the results, thereby creating apparent time series trends that don't really exist.

Results preferably cover complete days and complete weeks. Results collection can start any day of the week, but if there are 26 weeks of data that start on a Tuesday, then the last day should be the Monday that is 26*7=182 days later.

In certain aspects, it is preferred that a few extra hours of results at each end are included; that is, results would start a few hours before 12:00 AM Tuesday and end a few hours after 12:00 AM of the Tuesday that is 182 days later. This allows complete data for the first and last hour of the week when calculating patient result means and SDs by hour of the week using a moving window.

In one embodiment, the day of the week information is not necessary so long as the actual (calendar) date is provided. In certain aspects, for example, algorithms are used for determining the day of the week. For example in MATLAB the function weekday(date) returns a number between 1 and 7 denoting the day of the week (e.g., Sunday=1, . . . , Saturday=7) of the given date.

Minimum and/or Maximum Reportable Results

The minimum, maximum, and rounding factor (e.g., nsd) are preferably provided to the system, however such information can typically be inferred from the patient results themselves. It is generally safer to have the laboratory provide this information for each analyte. In order to utilize all of the patient data, patient results with a "<" are replaced with the minimum result−1*nsd, and results with a ">" are replaced with the maximum result+1*nsd.

The Number of Significant Digits

As stated in the previous section, the nsd can usually be inferred from patient results; however, it is safer to have the laboratory provide this information for each analyte.

Determine Truncation Limits

According to one embodiment, two processes are used to determine truncation limits to achieve the desired percentage of patient results that are outside truncation limits (pctout). In this embodiment, methodology 2 is preferably used as the primary method, and methodology 1 is used as a "sanity check." If the truncation limits from the two methods differ greatly, the cause should be investigated. It should be understood that each methodology may be used solely and separately. The two methodologies will now be discussed with reference to MATLAB functions and protocols, however it should be understood that other programming languages and applications may be used, for example, C, C++, Mathematica, Visual Basic, COBOL, PASCAL, FORTRAN, etc.

Methodology 1

According to one embodiment, truncation limits equidistant from the median of the un-truncated population are determined as follows:

1. Determine the total number, Nres, of patient results (e.g., using MATLAB, if the patient results are stored in a vector named "result" then the function length(result) will return the number of results in the vector).

2. Calculate the median (med) of all Nres results (e.g., in MATLAB the function median(result) will calculate the median of the results in the vector result).

3. Calculate the set of unique absolute differences, uadisttomed, between each patient result and the median (e.g., in MATLAB the function abs(x) will calculate the absolute value of x and the function unique(x) will return a vector that contains exactly one occurrence of each unique value in the vector x).

4. For each value of uadisttomed:

a. Determine the number of results, Nresout, whose absolute difference from the median, med, exceeds uadisttomed.

b. Calculate the percent truncated, pctresout=Nresout/Nres.

5. Select, automatically or manually, the value of uadisttomed that gives the pctresout that is closest in value to the target, pctout.

6. Calculate the lower truncation limit, tlo=med−uadisttomed and the upper truncation limit, thi=med+uadisttomed using the selected value of uadisttomed.

Methodology 2

According to one embodiment, truncation limits that maximize a decrease in the standard deviation of the truncated population relative to the number of samples that are truncated are determined as follows:

A. Calculate the SD of all patient results, for example:

1. Determine the total number, Nres, of patient results.

2. Calculate the standard deviation, SDres, of all the results (e.g., in MATLAB the function std(result) calculates the standard deviation of the results in the vector result).

B. Determine unique patient results, for example:

1. Determine all the unique values, ures, of the patient results.

2. Sort the unique values, ures, from smallest to largest (e.g., the MATLAB function unique(result) will return the unique result values in sorted order).

C. Initially set the truncation limits to the lowest and highest result and the percent truncated to zero, for example:

1. Let tlo=the smallest ures value.

2. Let thi=the largest ures value.

3. Set pctout=0.

D. Move in truncation limits from one tail and recalculate: Repeatedly move in (automatically or manually) the truncation limits from one or the other tail of the result distribution and recalculate the percent outside truncation limits until the percent outside truncation limits exceeds pctout, for example:

1. Count the number of results, Nrestlo, that equal tlo.

2. Count the number of results, Nresthi, that equal thi.

3. Calculate the standard deviation, SDrestlo, of the results that are greater than tlo and less than or equal to thi (include the results that equal tlo to those that are already excluded).

4. Calculate the standard deviation, SDresthi, of the results that are ≧tlo and <thi (include the results that equal thi to those that are already excluded).

5. Compare the value of (SDres−SDrestlo)/Nrestlo to the value of (SDres−SDresthi)/Nresthi.

E. Determine which tail gives the greater reduction.

$$(SDres-SDrestlo)/Nrestlo > (SDres-SDresthi)/Nresthi$$

For example, if (SDres−SDrestlo)/Nrestlo>(SDres−SDresthi)/Nresthi then moving in the lower truncation limit produces the larger decrease in SDres relative to the number of samples lost due to truncation.
 1. Replace tlo with the smallest value of ures that is >tlo.
 2. Replace SDres with SDrestlo.

(SDres−SDrestlo)/Nrestlo≦(SDres−SDresthi)/Nresthi

For example, if (SDres−SDrestlo)/Nrestlo≦(SDres−SDresthi)/Nresthi then moving in the upper truncation limit produces the larger decrease in SDres relative to the number of samples lost due to truncation.
 1. Replace thi with the largest value of ures that is <thi.
 2. Replace SDres with SDresthi.
F. Determine the number of results, Nresout, that are less than tlo or greater than th. (This calculation preferably includes all values, including replicates.)
G. Calculate the percent of results outside truncation limits For example, pctresout=Nresout/Nres provides the percent of results outside truncation limits. When pctresout becomes greater than or equal to pctout, the corresponding (tlo,thi) pair gives pctresout>pctout and the (tlo,thi) pair at the step just prior gives pctresout<pctout. Select as the lower and upper truncation limits the (tlo,thi) pair that minimizes the absolute difference between pctresout and pctout. This is done by determining the first tL,tU pair, and that tL gives the larger SD decrease.

Calculate Patient Means and SDS for Each Hour of the Week

According to one embodiment, a calculation of the patient means and standard deviations (SDs) for each hour of the week is performed as follows:

Require that each moving window contains a minimum number of results. (e.g., twenty would be an adequate number, but forty or more would be better.)

Use a moving window of one hour±one hour (e.g., to create a three-hour window) whenever the window has at least the minimum number of results. Using a moving window smoothes the estimates of the means and SD and helps increase the sample sizes of the estimates.

If the one hour±one hour window has fewer than the minimum number of results, widen the window by including the results that are closest in time to the one hour±one hour window until the window contains at least the minimum number of values. For example, if the current window is 5 results short then find the 5 results closest in time to the current window and widen the window just enough to include these 5 results.

The calculations generally require the following input values: a collection of patient results within truncation limits, resin; the hour of the week, hrwk, for each result (e.g., hrwk ranges from 1 to 7*24=168); the week number, wkn, of the result (e.g., if there are 13 weeks of data in resin then wkn ranges from 1 to 13); and the half-width of the moving window, whlfwdth (e.g., in hours) used to calculate the means and standard deviations.

The calculations generally provide the following output results: Nresin(hrwk)—the number of results used in the calculations for hour of the week, hrwk; avgresin(hrwk)—the average of the results within the window for the hour; SDTresin(hrwk)—the total standard deviation for the hour; SDBresin(hrwk)—the week-to-week (between-week) standard deviation for the hour; and SDWresin(hrwk)—the within-week standard deviation for the hour.

According to one embodiment, a calculation is performed as follows for each hour of the week:
1. Determine the results, resin(hrwk) that are within the moving window for hour hrwk.

For the first whlfwdth hours of the week (hrwk=1 to whlfwdth), resin(hrwk) will be the results where hour of the week ≧hrwk−whlfwdth+168 or ≦hrwk+whlfwdth. (The left half of the window needs to "wrap").

For each hour between whlfwdth+1 and 168−whlfwdth, resin(hrwk) will be the results where hour of the week ≧hrwk−whlfwdth and ≦hrwk+whlfwdth.

For the last whlfwdth hours of the week (hrwk=168−whlfwdth+1 to 168), resin(hrwk) will be the results where hour of the week ≧whlfwdth−hrwk or ≦whlfwdth+hrwk−168. (The right half of the window has to "wrap")
2. Determine the number, Nresin(hrwk), of results defined by resin(hrwk).
3. Calculate the average, avgresin(hrwk) of the results defined by resin(hrwk).
4. Calculate the deviations devavgresin(hrwk)=resin(hrwk)−avgresin(hrwk).
5. Perform a one-way random effects analysis of variance (ANOVA) on the deviations devavgresin versus week number, wkn to obtain SDTresin, SDBresin, and SDWresin. For example, the MATLAB function [SDTresin,SDBresin,SDWresin]=sdtbw(devavgresin,wkn) can be used to perform the necessary ANOVA calculations.

Create Analyte-Specific, Truncated Populations

In one embodiment, it is preferable to determine the truncation limits that minimize the worst case expected number of "bad" results produced or reported during an out-of-control error condition (ANPTE) over a wide range of error conditions. In general, a "bad" result is a result where the difference between the true concentration and the measured concentration exceeds the total allowable error specification ($TE_a$). ANPTE should be measured by simulation. Therefore, determining analyte specific truncation limits based on worst-case ANPTE performance requires accurate simulation of the time-series characteristics of the patient results in order to calculate ANPTE for different sets of truncation limits and different magnitudes of out-of-control error conditions.

In certain aspects, implementing a patient-based quality control (QC) rule requires the following parameters:
 Truncation limits—tlo and thi;
 The average of patient results within truncation limits for each hour of the week—avgresin(hrwk);
 The total standard deviation of patient results within truncation limits for each hour of the week—SDTresin(hrwk);
 Number, Npat, of consecutive within-truncation-limits patient samples to average; and
 The two parameters that define the QC rule, for example:
 w and q for the EWMA rule.
 h and k for the CUSUM rule
 Note: In certain aspects, only the EWMA rule is implemented, however, the CUSUM rule may be implemented additionally or alternatively.

QC performance measures to evaluate a patient-based QC rule typically include:
 $ANP_{fr}$ (The average number of patient results between false rejections);
 $ANP_{ed}(SE,RE)$, SE≠0, RE>1 (The average number of patient results to error detection when an out-of-control error condition with shift=SE and increase in stable analytic imprecision=RE exits)
 ANPTE(SE,RE), SE≠0, RE>1 (The average number of "bad" results produced during an out-of-control error condition with shift=SE and increase in stable analytic imprecision=RE)

Selecting the Patient-Based QC Parameters

Ideally, one specifies a target $ANP_{fr}$, and then selects the parameters that minimize the maximum (worst-case) value of ANPTE(SE,RE) over a wide range of out-of-control conditions. However, because the patient-based QC parameters are typically all inter-related, finding the "optimal" combination (including the "optimal" truncation limits) may be a complicated task. Accordingly, in one embodiment, determining truncation limits when using the EWMA rule is performed as follows:

1. Specify a target $ANP_{fr}$ for the patient-based QC rule;
2. Set Npat=1;
3. Select an EWMA parameter w that is optimal for detecting $SE=TE_a$;
4. Find truncation limits that eliminate one or more of the following percentages of patient results: 0.5%, 1%, 2%, 5%, and 10%;
5. For each set of truncation limits:
   a. Calculate avgresin(hrwk) and SDTresin(hrwk);
   b. Find (by simulation) the EWMA parameter,q, that gives the target $ANP_{fr}$;
   c. Calculate (by simulation) Peak=(ANPTE($-TE_a$)+ ANPTE($TE_a$))/2; and
6. Select the truncation limits that minimize the value of Peak.

This approach optimizes truncation limits for detecting SE errors but ignores the effect of RE error conditions. $TE_a$ can be given as either an absolute value or a percent. The published Ricos limits may be used.

Simulation of in-Control, Time-Series Patient Results

According to one embodiment, a time-series bootstrap approach based on block resampling of consecutive sets of patient results over time is implemented by Biometric QC module 40 to simulate in-control, time-series patient results. The patient results (data) and their date/time stamps are utilized in the simulation. In this embodiment, data preferably covers complete days and complete weeks and is sorted by date and time (a few extra hours of patient results at the beginning and end is generally not desired in this case).

The simulation of in-control patient data proceeds as follows according to one embodiment:

1. Generate a random date and time within the date and time interval spanned by the patient data. The first date/time stamp in the patient database immediately following the random date/time marks the beginning point of the simulation.
2. Find all the results that proceed or follow this point in time by, for example, no more than W minutes (e.g., w=120 minutes).
3. If the number of results within ±w minutes of the current result is <10, then continue searching backward and forward in time until 10 results are identified.
4. Randomly sample one of the results within the ±w minute block. This is the first simulated patient result.
5. Move to the next date/time stamp and repeat the process.
6. Continue in this fashion until the QC rule rejects.

In this embodiment, one "tricky" part occurs when the simulation is near the beginning or ending date of the patient data, because the simulation needs to "wrap around" from the last date/time point to the first date/time point in the database. This is why it is preferred that the database contain complete days and complete weeks of data so that when the simulation wraps around it wraps to the correct hour of the day and day of the week.

An example of a useful MATLAB function for simulating in-control time-series patient results follows:

---

MATLAB Function-Simwin.m

```
function [r,rb,rn]=simwin(result,day,hr,minute,winlen,minnum)
% Determines a random sampling window for each result in the
% patient result vector. For the result in row i, the sampling
% window begins at row rb(i) and includes rn(i) rows ie., rows
% rb(i) to rb(i)+rn(i)-1. The window width is derived to span
% +/-winlen minutes. Whenever the +/-winlen window fails to include
% at least minnum results, the window is widened the shortest length
% of time in either direction necessary to include minnum results
minday=min(day);
[et,ordr]=sort((day-minday)*24*60+hr*60+minute);
if ordr(:)~=[1:length(et)]'
    error('results must be in date/time order')
end
% start at either the first or second day depending on which gives
% the largest time range and most complete first and last day
strt1=min(find(day==minday));
maxday=minday+fix((max(day)-minday)/7)*7-1;      % make complete weeks
end1=max(find(day==maxday));
et1=et(end1)-et(strt1);
mindaynxt=min(day(day>minday));
strt2=min(find(day==mindaynxt));
maxdaynxt=mindaynxt+fix((max(day)-mindaynxt)/7)*7-1;
end2=max(find(day==maxdaynxt));
et2=et(end2)-et(strt2);
if et1>=et2
    et=et(strt1:end1);
    r=result(strt1:end1);
else
    et=et(strt2:end2);
    r=result(strt2:end2);
end
n=length(r);
wl=zeros(size(r));
wr=wl;
shft=1;
gor=find(et(shft+1:n)-et(1:n-shft)<=winlen);
% gor = rows where et(i+shft)-et(i)<=winlen (gor: "go right")
```

-continued

MATLAB Function-Simwin.m

```
while ~isempty(gor)               % keep widening windows until all exceed +/-winlen
        wr(gor)=wr(gor)+1;        % wr = # rows window extends to the right
        gol=gor+shft;             % gol = rows where et(j)-et(j-shft)<=winlen
% Note if row i is within winlen of row i+shft
% then row j=i+shft is within winlen of row i
        wl(gol)=wl(gol)+1;   % wl = # rows window extends to the left
        shft=shft+1;
        gor=find(et(shft+1:n)-et(1:n-shft)<=winlen);
end
i=find(wl+wr+1<minnum); % rows with < minnum within window
while ~isempty(i); % keep widening windows until all have at least minnum
        m=i((i-wl(i)>1) & (i+wr(i)<n)); % rows that don't abutt either end
        gol=[i(i+wr(i)==n);m((et(m)-et(m-wl(m)-1))<=(et(m+wr(m)+1)-et(m)))];
        % extend to the left if current window abutts the right end or if the
        % next time pt to the left is closer than the next time pt to the right
        gor=[i(i-wl(i)==1);m((et(m)-et(m-wl(m)-1))>(et(m+wr(m)+1)-et(m)))];
        % extend to the right if current window abutts the left end or if the
        % next time pt to the right is closer than the next time pt to the left
        wl(gol)=wl(gol)+1;
        wr(gor)=wr(gor)+1;
        i=find(wl+wr+1<minnum);
end
rb=[1:n]'-wl;                     % beginning row number for window
rn=wl+wr+1;                       % number of rows within window.
```

The MATLAB function named simwin determines the points that are within the window for each of the observed values. This algorithm requires the 91-day vector of patient results with the day, hour, and minute of each result. The simwin function figures out ½ of the window width (w) for a moving window. Within the function, minnum assures that a minimum number of results in the window exist.

For example, using a minimum number of 10 and a window of ±120 minutes, if a particular window contains fewer than 10 results, the window is widened until the minimum number of results is obtained. This results in a 1 in 10 chance of sampling a particular result. Using is approach, the chances of sampling the exact same results is very small. For example, after 5 windows have been sampled, the chances of sampling the same results is approximately 10−5.

The input into the function simwin are a particular value for the window width (w) and the minimum number of samples in the window (minnum). The output of simwin produces two variables—rb and rn, where rb is the beginning row of the window (rows are associated with a particular date and time), and rn is the number of rows in the window. Together, rb and rn determine the window that defines the rows.

The algorithm uses a moving window of the results. The simulation takes actual laboratory results with date and time stamp, in order, by date and time, and figures out a window that is well defined and simulates the results but makes use of the time-distribution of the data. Using this approach, a very large number of data points can be simulated, for example, if 5,000 patient data points are used, an effective simulation of a database of 500 million data points can be performed.

Another useful algorithm for simulating results that reflect the time-series nature of the underlying data is the MATLAB function nttsim:

MATLAB Function-nttssim.m

```
function nextres=nttssim(result,rb,rn,timptr)
% function to simulate the next result
% result = patient result vector in time sorted order
% rb = result row # of first result for sampling window
% rn = number of results in sampling window
% timptr = a vector of length Nsim that contains pointers
%          to the date and time of the simulated result
% nextres = vector of length Nsim of the next set of simulated results
Nres=length(result);
Nsim=length(timptr); % # of simulated results generated concurrently
timptr=mod(timptr,Nres)+1; % wrap to beginning when get to end
nextres=result(rb(timptr)+fix(rand(Nsim,1).*rn(timptr)));
```

The inputs for the function nttsim are the set of patient raw data (result vector), rb, rn (where rb and rn are the output from the function simwin.m), and a time pointer (timptr), which keeps track of where we are in time in the series of results. Within the function, timptr is defined as a vector of length Nsim that contains pointers to the date and time of the simulated result (nextres), where nextres is a vector of length Nsim of the next set of simulated results. Stated another way, timptr is a vector and the number of rows it contains is the number of simulations that are being performed simultaneously. When a simulation is performed, each row is a separate trial. For example, if 10,000 simulations are desired, create a vector that contains 10,000 rows. Each row will be a separate simulation trial, so that 10,000 simulations will be performed.

One way to populate the timptr vector is to randomly generate numbers between 1 and the number of results in the patient-result vector, populate all rows (for example 1000 rows) of the timptr vector with these random numbers, use these points as random starting points for this simulation trial, at each step, move to the next point in time (i.e., the next row in the timptr vector), and at this row, the nextres line of the nttssim.m function determines which result will be used as the next random result.

When the last result in the timptr vector is reached, the algorithm must loop around to the first result in the timptr vector. The mod of MATLAB is useful for doing this.

Figure 4:
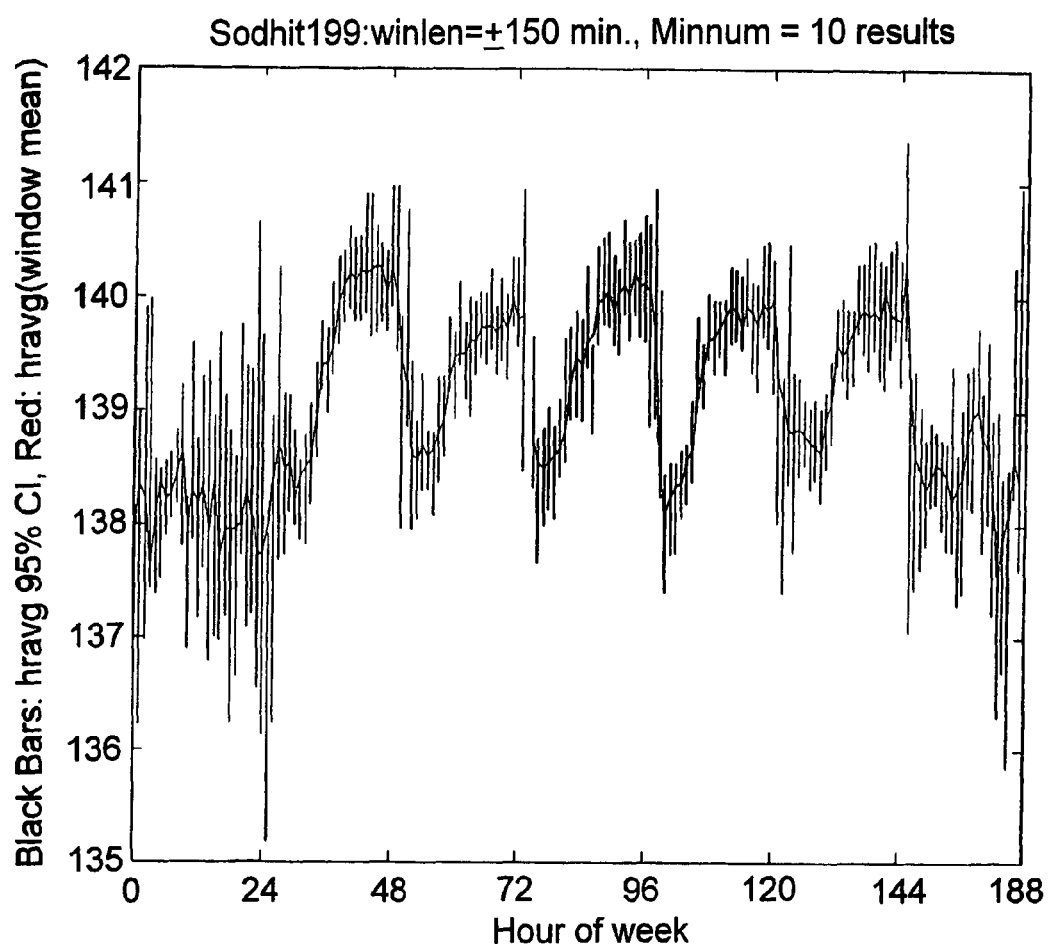
FIG. 4 shows an example of expected values for each hour of the week when a simulation has been run according to one embodiment.

FIG. 4 shows an example of expected values for each hour of the week when a simulation has been run. In FIG. 4, the hourly mean of the window (shown by the red line) was kept, and the hour-to-hour curve was replaced with vertical bars that represent a 95% confidence of the hourly mean of the window. To clarify, the red curve represents the mean of the simulation window and the vertical bars represent the actual mean of the values within the hour ±2 SD of the mean of the actual data. This provides a better sense of the number of points that went into the hourly mean of the window and provides an overview of the precision with which the hourly average was determined. This decreases apparent discrepancies between the red and blue lines when some hours have no or very few data points. If this curve is doing its job the red line should be approximately at the center of the vertical bars. It should be noted that each hour includes all the data points run within that hour over a year, so 2000 specimens/hour represents 2000 specimens/hour per year.

The close fit of the moving window mean to the raw patient mean demonstrates that the simulation models the time-series nature of the data accurately with a winlen of 150 minutes and a minimum number of results per window of 10.

Figure 5:
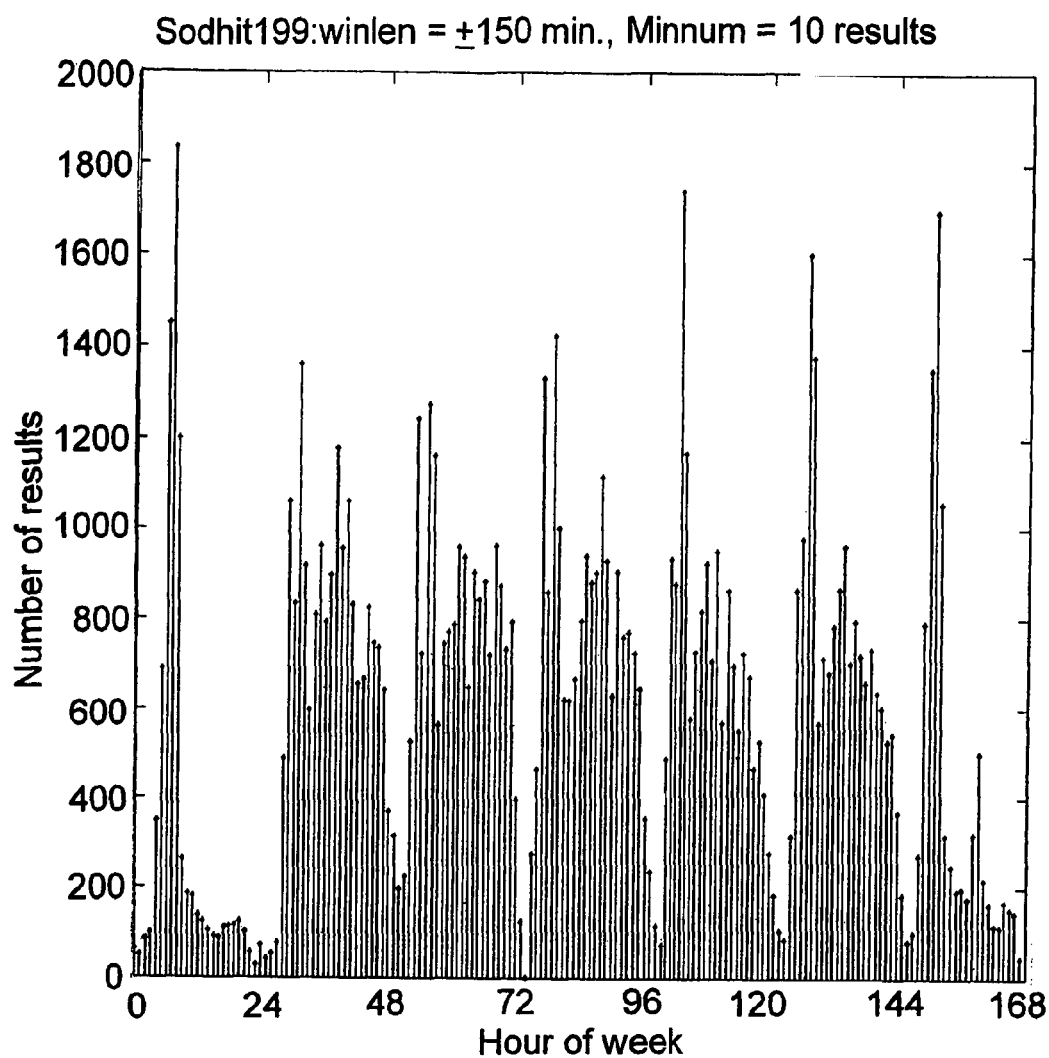
FIG. 5 shows an example of the number of results per hour according to one embodiment.

FIG. 5 shows an example of the number of results per hour.

It should be noted that because the population modeled should be homogeneous, instruments serving different populations (e.g., routine, stat, or ICU) should be modeled separately. Also, the purpose of performing simulations with different window lengths and minimum number of samples is to determine how to set the window lengths and minimum number of samples to obtain an optimal autocorrelation between real and simulated data. Using a minimum of 10 samples (and a ±120 min to a ±150 min window), however, should be sufficient for most labs.

Figure 6:
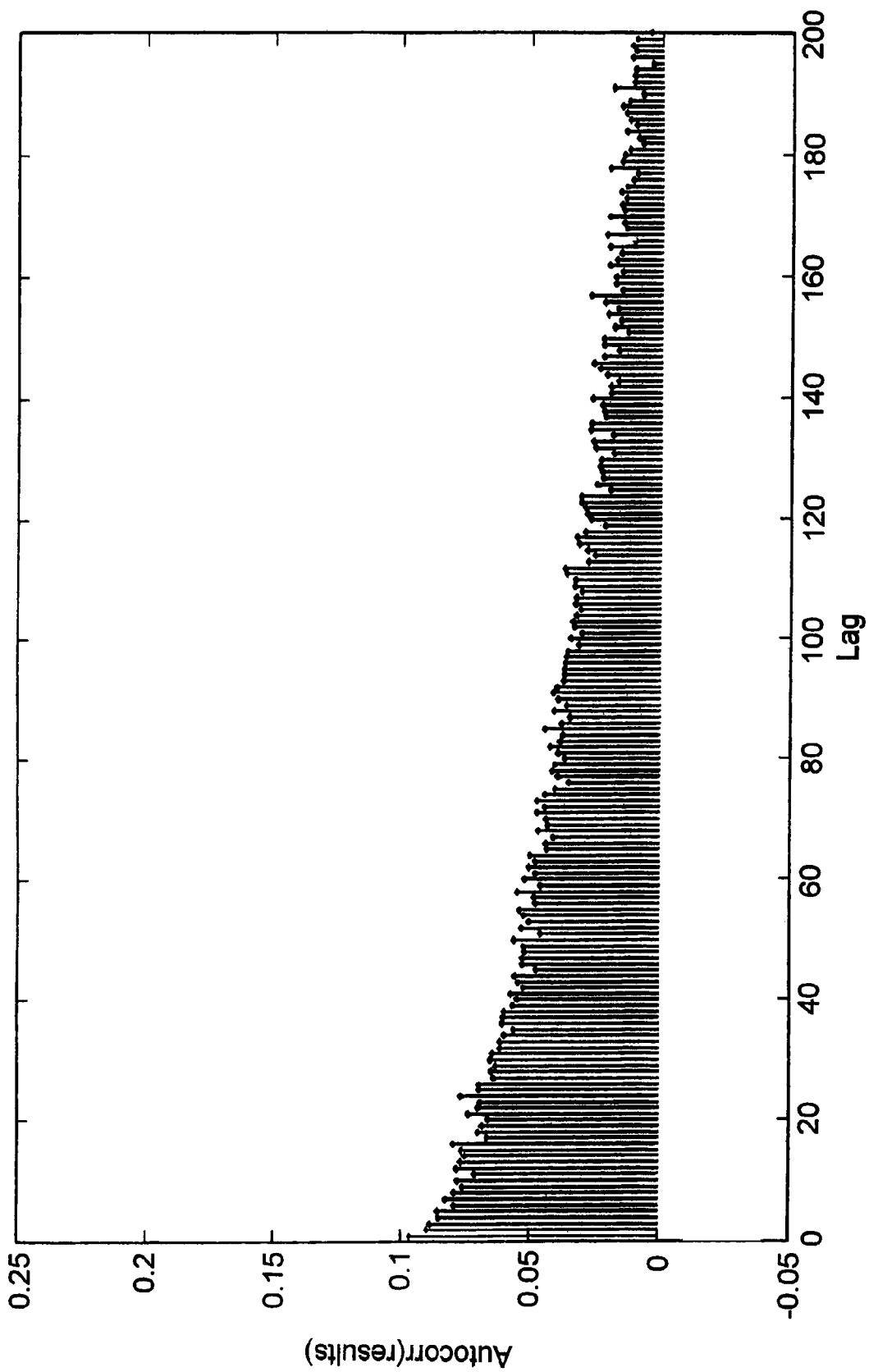
FIG. 6 and FIG. 7 show example autocorrelation functions which demonstrate that the algorithm adequately represents the serial correlation in the data according to one embodiment.
Figure 7:
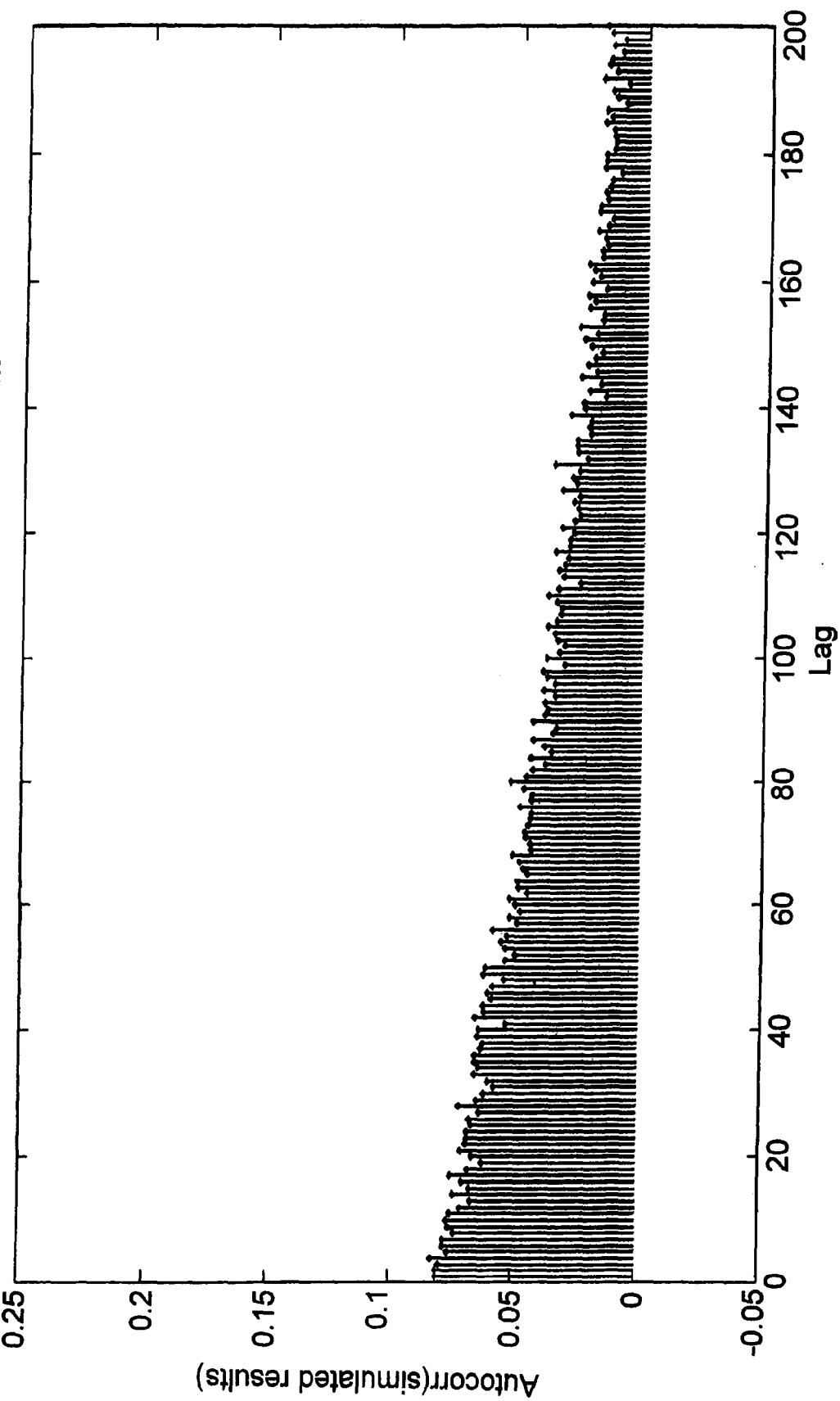

FIG. 6 and FIG. 7 show example autocorrelation functions which demonstrate that the algorithm adequately represents the serial correlation in the data. The points at 0.09 on the y-axis represent the correlation of pairs of data formed by each result and the result immediately prior to it. (The correlation for each of these pairs is 0.09.) The autocorrelation function determines how much independence the results have from one another.

As lag (the number of results prior to the result) increases, the correlation decreases. This demonstrates that there is a serial correlation in the data. For example, results on Monday morning are more similar to one another (e.g., less independent and more correlated) than they are to results on Friday afternoon.

For FIG. 7, the same number of data points contained in the original raw patient data used for the simulated. For example, for 60K data points in the patient data, the timptr vector should be populated with 60K simulated data points. FIG. 6 shows the autocorrelation for simulated data and demonstrates that the algorithm preserves autocorrelation observed with the raw patient data.

Figure 8:
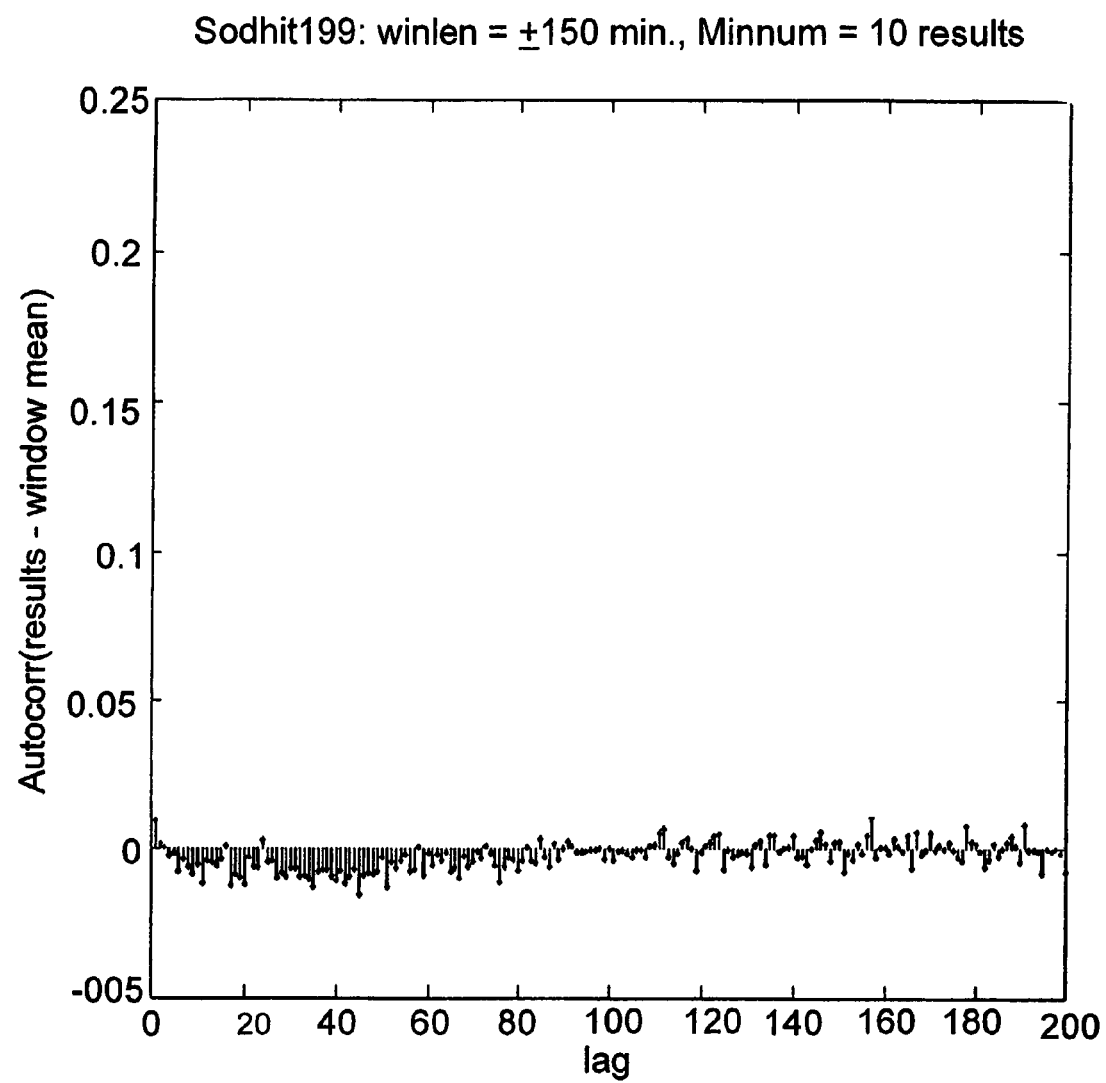
FIG. 8 represents an autocorrelation between actual and simulated results according to one embodiment.

FIG. 8 represents an autocorrelation between the actual and simulated results. The justifies using an hour-by-hour average, because if not, only white noise is left (i.e., there is no correlation).

If only three months worth of data is provided and those days occur at the end of the year, the data may over-represent unusual days. Operating characteristics can be modified as more data are acquired/provided. For example, the initial operating characteristics can be set using the available lab data and when a year's data has been obtained, the operating characteristics can be re-evaluated. These operating characteristics should be stable until there is a change in the patient population. When a change in the patient population occurs, the operating characteristics should be recalculated.

Simulation of an Out-of-Control Error Condition

In one embodiment, simulation of an out-of-control error condition is performed by Biometric QC application 40.

Simulating an out-of-control error condition generally involves determining how to transform the distribution of patient results so that the mean and SD of the transformed distribution accurately manifests the out-of-control error condition. The fact that the patient result data used in the simulations are typically rounded may cause some problems when trying to accurately simulate an out-of-control error condition. According to one embodiment, a strategy is provided for creating an out-of-control result distribution to overcome the problems associated with rounding as follows:

1. For result, x, first "unround" the result by adding a uniformly distributed random number between ±0.5*nsd to x; call it $x_T$.

2. Next, add $SE(x_T)$ to $x_T$, where $SE(x_T)$ is the magnitude of the out-of-control error condition at concentration $x_T$.

3. Next, round the result to nsd digits. If the out-of-control result is outside the minimum or maximum reportable results, replace it with the minimum−1*nsd or maximum+1*nsd respectively.

In certain aspects, when simulating SE error conditions, if the total allowable error specification ($TE_a$) for the analyte is given as a constant, it is preferred to specify SE as a constant, and if $TE_a$ is given as proportional to concentration, to specify SE as proportional to concentration. Unlike simulations of control QC strategies, both negative and positive SE error conditions are preferably simulated because the non-normal distributional characteristics of the patient distributions mean that symmetrical behavior between positive and negative error conditions can't be expected.

It is preferred that SE range between ±2TEa. Also, any combination of SE and RE error is preferably handled in the following way:

1. Unround as above.

2. Next, multiply the unrounded result by a normally distributed random number with mean=0 and variance=$(RE^2-1)*SD(x_T)$, where $SD(x_T)$ is the stable analytic imprecision at concentration $x_T$ and RE is the magnitude of the increase in imprecision given in multiples of stable analytic SD.

3. Next, add $SE(x_T)$ and round to nsd digits as before.

Simulating the out-of-control time series characteristics of patient results proceeds in the same way as for in-control results except that an out-of-control result is randomly sampled from the ±w minute block of transformed results on either side of the current date/time stamp.

An example of a useful MATLAB function for simulating an out-of control error condition follows:

```
function reserr=sereerr(result,Sa,reprng,nsd,ase,bse,RE)
% create an out-of-control vector of patient results, reserr, from an
% in-control vector, result, assuming SE=ase+(bse−1)*result and or
RE>=1.
% resunrnd is the in-control unrounded measured result
% resunrnderr is resunrnd with error due to the out-of-control error
condition
% Sa = the analytical SD for each result
% reprng = min and max reportable value for result
% nsd = number of significant digits results are rounded to
Nres=length(result);          % total number of results
minres=reprng(1)−nsd;         % make min value = lower limit − nsd
maxres=reprng(2)+nsd;         % make max value = upper limit + nsd
resunrnd=result+(rand(Nres,1)−0.5)*nsd; % "unround" the results
Sainc=sqrt(RE. 2−1).*Sa;      % additional SD needed to increase to
                              re*Sa
% add extra random error and shift by SE
resunrnderr=ase+bse*normrnd(resunrnd,Sainc);
% round and limit to [minx,maxx]
reserr=min(maxres,max(minres,round(resunrnderr/nsd)*nsd));
```

The above MATLAB function sereerr (systematic error-random-error error) functions to transform the distribution of the raw patient data to simulate a particular systematic or random out-of-control situation. The inputs for the function sereerr include raw patient values (results vector), analytic imprecision of the method, and Sa vector. The Sa vector represents the analytic SD, which is the inherent analytic imprecision of the stable process for each result concentration. The Sa vector has the same length as the results vector and contains the analytic imprecision for every result in the results vector at the concentration of the result. The value in the Sa vector can be absolute or a percentage. In the case of an absolute imprecision, every value in the Sa vector would be the same. In the case of a percentage imprecision, the values in the Sa vector vary depending on the value in the results vector.

Additional inputs for the function sereerr include Reprng (Report range is the minimum and maximum reportable values for the assay), nsd (the number of significant digits. The function uses the nsd to "unround" the raw data results), ase (represents the intercept for the systematic error), bse (represents the slope for the systematic error), and RE (represents random error). Ase and bse are used to simulate constant and proportional shifts in raw patient values. For example, if a=1 and b=1, every shifted result is 1 more than the original and the shift is constant, and if a=0 and b=1.1, every shifted result is 10% higher than its original result and the shift is proportional. RE=1 indicates the stable analytic imprecision, and RE=2 indicates an out-of-control error condition resulting in a doubling of the stable analytic imprecision of the assay.

Because results in the raw patient data are rounded, the function "unrounds" each value to make the simulation work well. To do this, a uniform random number, e.g., ±0.5 (the rounding width), is added to the patient results.

QC Confirmation Testing Module

According to one embodiment of the present invention, the Biometric QC application module 40 includes a QC Confirmation Testing module 46 configured to determine an optimal QC rule (and associated number of QC samples) needed to confirm that the analytical process is still in control after an event has occurred. The optimal rule minimizes the worst case probability of producing "bad" results (pQE) because of an error condition associated with the event. In preferred aspects, the QC Confirmation Testing module 46 determines an optimal QC rule using the following general steps.

Step 1—Identify a Relevant Performance Measure

According to one embodiment, the algorithm includes a module configured to determine an optimal QC rule (and associated number of QC samples) needed to confirm that the analytical process is still in control after an event has occurred. In one embodiment, the optimal rule to be determined should minimize the worst-case probability of producing "bad" results (pQE) because of an error-condition associated with the event.

This approach is consistent with the basic approach for routine QC tests, except that for routine QC testing an error occurring is modeled at some point in time and then it is determined how many samples are needed to detect the condition.

Step 2—Select a QC Rule

The $\bar{X}/S$ rule is preferably used, because it has been shown that the $\bar{X}/S$ rule is the best QC rule for testing a single group of QC samples. (See, e.g., Parvin C A. New insight into the comparative power of quality-control rules that use control observations within a single analytical run. Clin Chem 1993; 39:440-7).

Step 3—Determine the pQE

Two probabilities are required to calculate the probability of producing a bad result (pQE): 1) the probability of producing a bad result due to an out-of-control error condition (dpE), and 2) the probability of error detection (ped). The pQE is equal to the increase in the probability of producing "bad" results because of the error condition multiplied by the probability of failing to detect the error condition, as given in the following formula: pQE=dpE*(1−ped). Using this approach, the probability of producing a "bad" result (pQE) can be determined when using a specific QC rule after an event.

Figure 9:
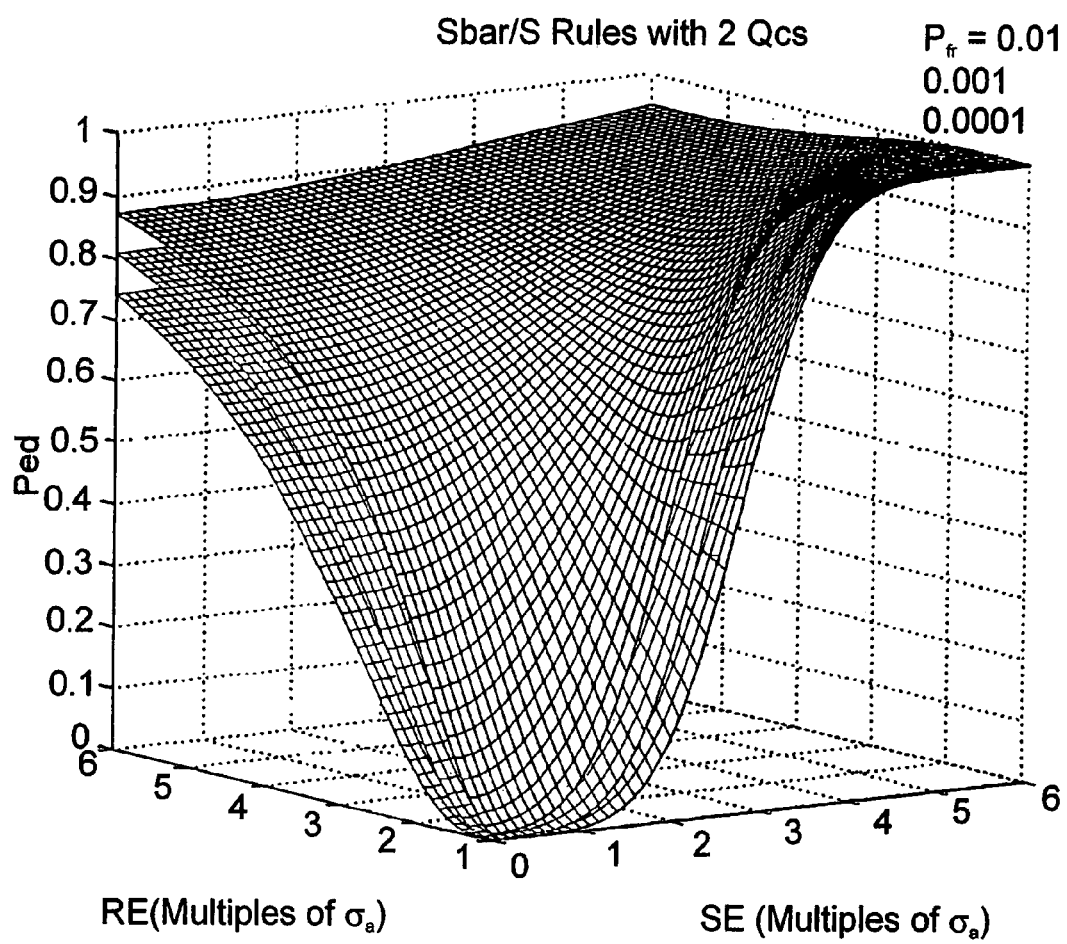
FIG. 9 shows power functions for an $\overline{X}/S$ rule with rejection limits set to give three different false rejection rates ($p_{fr}$=0.01,0.001,0.0001) according to one embodiment.
Figure 11:
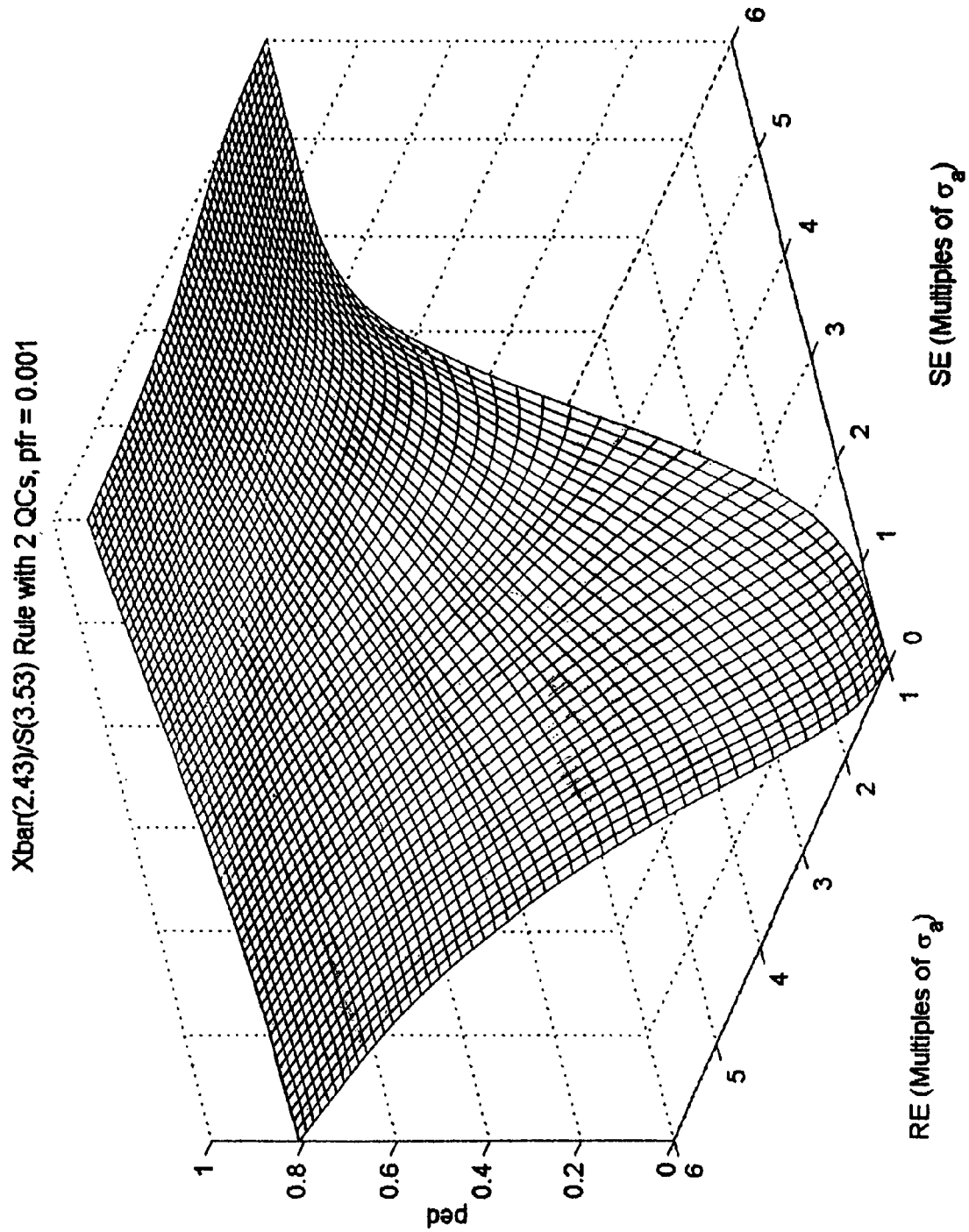
FIG. 11 shows the probability of error detection for a particular QC rule according to one embodiment.
Figure 13:
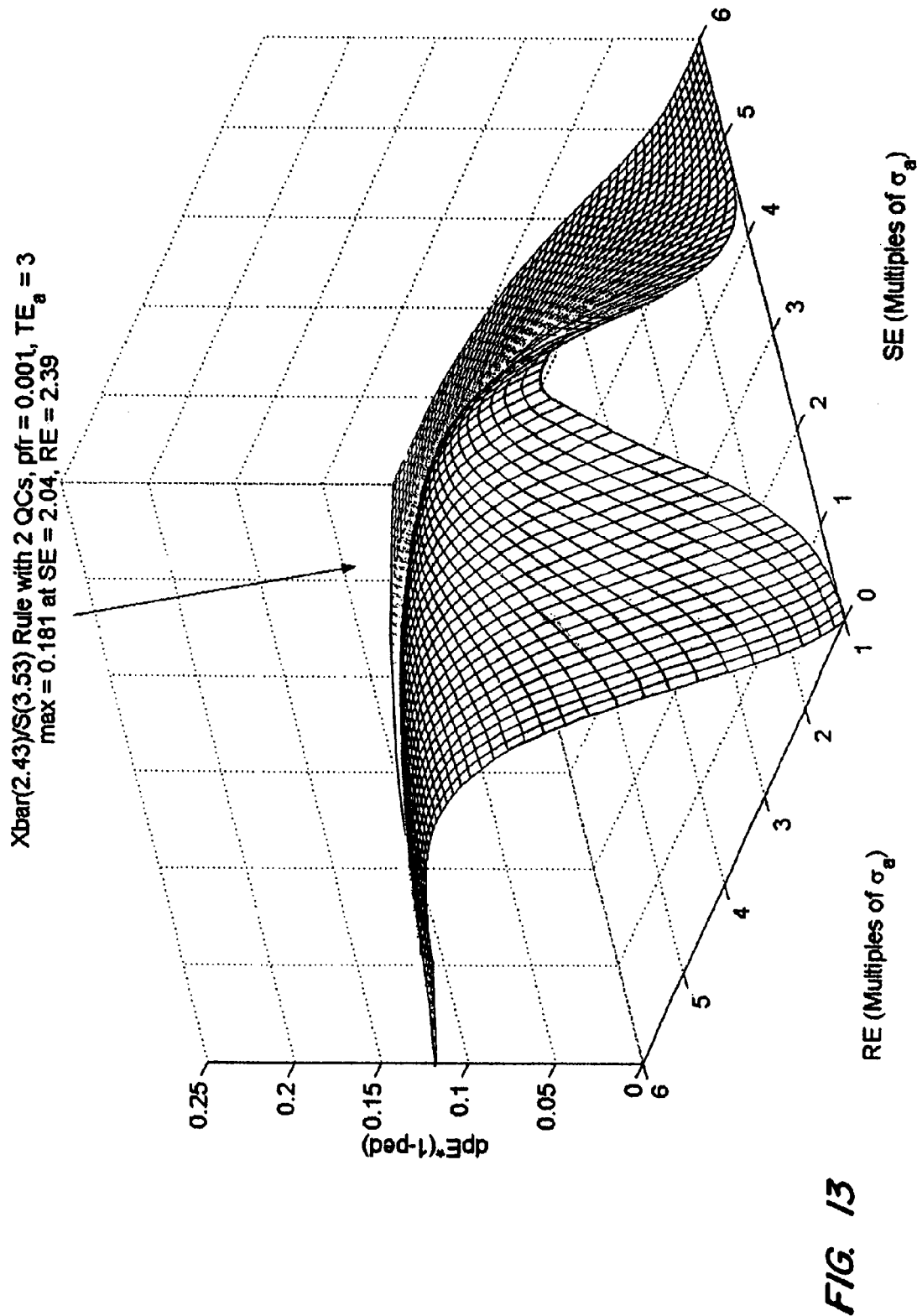
FIG. 13 shows the probability of producing "bad" results if this QC rule is used after an "event" according to one embodiment.
Figure 14:
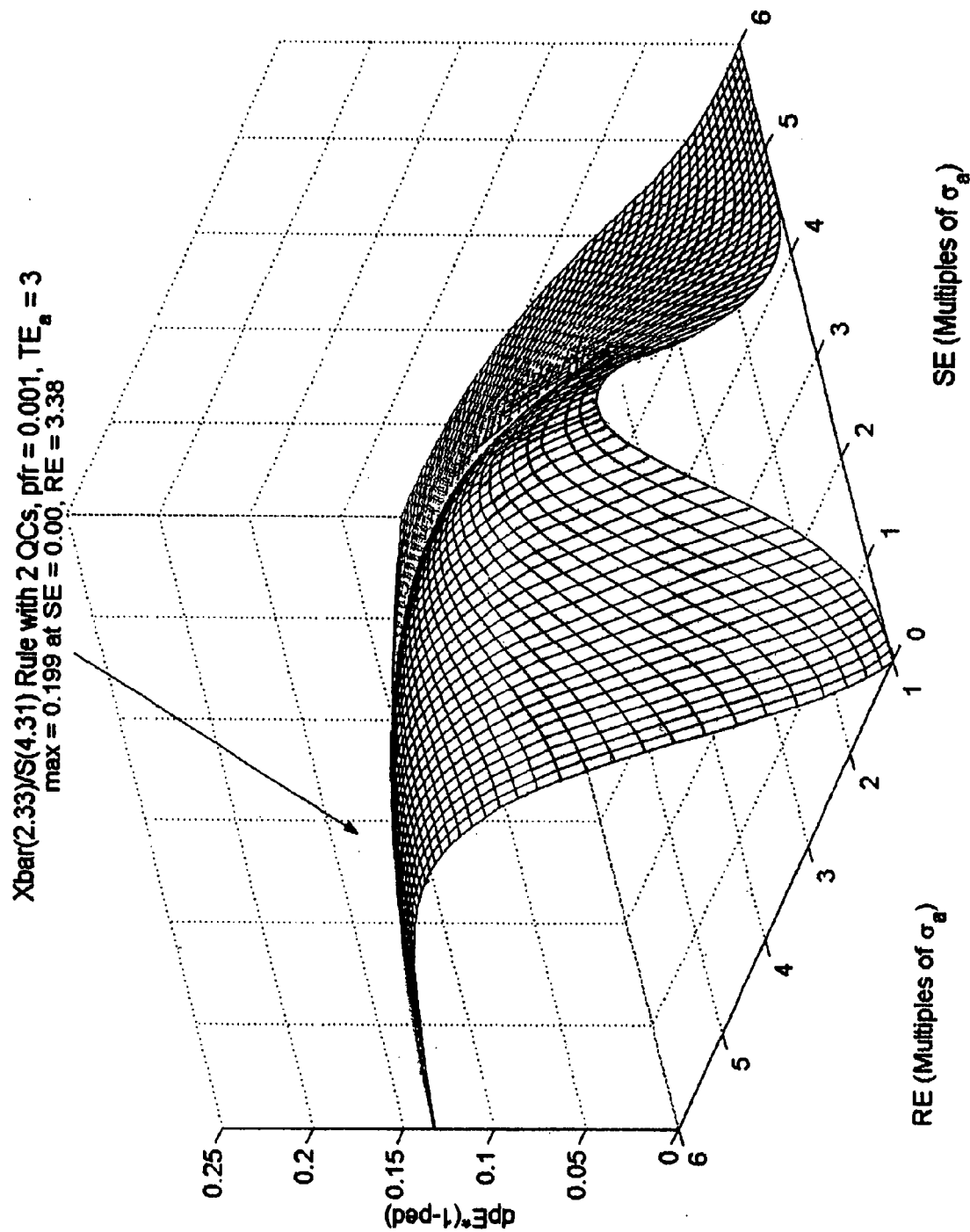
FIGS. 14 through 18 show how the pQE surface changes as the control limits for the $\overline{X}/S$ rule are varied to provide more or less error detection for SE errors versus RE errors according to one embodiment.
Figure 15:
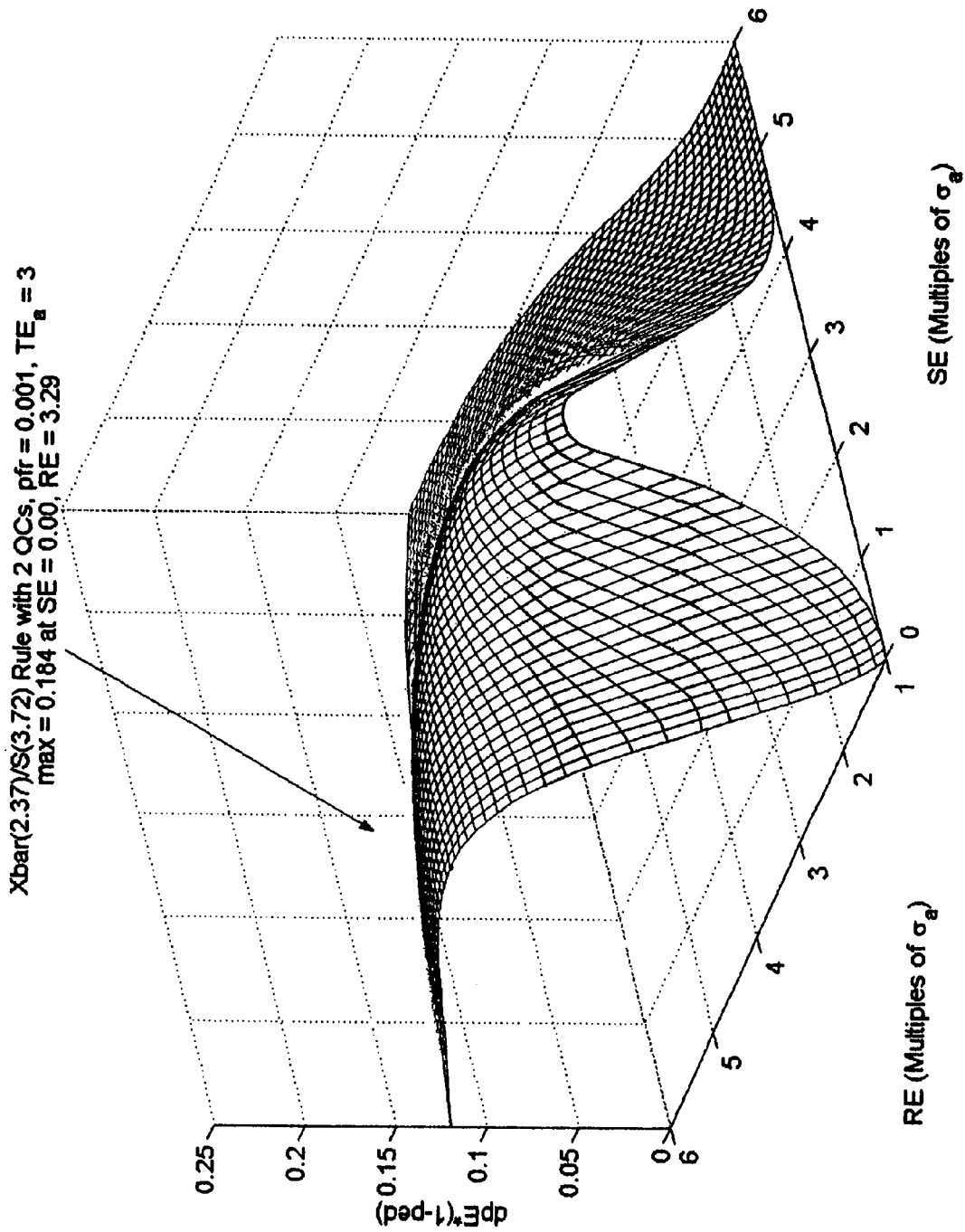

FIGS. 9 and 11 show examples of the probability of error detection (ped) plotted as a function of SE and RE simultaneously, producing a surface plot that generalizes the power function to cover all combinations of systematic and random error conditions. FIG. 13 shows an example of a pQE surface as a function of RE and SE.

Step 4—Vary Error Limits to Minimize pQE

When choosing the QC rule to use after an "event", it is desirable to minimize the worst-case probability of producing "bad" results because of an error-condition associated with the "event." FIGS. 14 through 18 illustrate how assigning error detection ability between $\bar{X}$ and S can be used to select the QC rule to minimize the worst-case probability of "bad" results. As shown, as the $\bar{X}$ and S values vary, the relative power for detecting a shift in the away from the target value (SE) or an increase in stable analytic imprecision (RE) also varies.

Step 5—Vary Rejection Limits to Guarantee that pQE is Never >5%

In this step, $\bar{X}$ and S rejection limits are varied and the number of QC samples over a range of total allowable error specifications ($TE_a$) and false rejection rates ($p_{fr}$) are varied to guarantee that the pQE never exceeds 5%, regardless of the error condition. It should be appreciated that the selection of 5% for the pQE was arbitrary, and it could be smaller or larger as desired. In addition, the number of QC samples is restricted to multiples of two, which is generally the number of samples that labs run for general chemistry tests.

Step 1 and 2 Discussion

Steps 1 and 2 require no further discussion at this time.

Step 3 Discussion

The algorithm is preferably configured to consider out-of-control error conditions that result in a shift from target values (SE), an increase in stable analytic imprecision (RE), and/or an increase in both SE and RE.

FIG. 9 shows power functions for an $\bar{X}/S$ rule with rejection limits set to give three different false rejection rates ($p_{fr}$=0.01,0.001,0.0001) according to one embodiment. The probability of error detection ($p_{ed}$) is plotted as a function of SE and RE simultaneously. The curve represented by the line along the SE axis (RE=1) provides power to detect a systematic error. The curve along the RE axis (SE=0) provides power to detect a random error. This surface plot generalizes the power function to cover all the combinations of systematic and random error conditions. In FIG. 9, the floor defines the SE/RE combinations in multiples of the analytic SD. On the SE scale, which represents a shift, a value of 0 means that there is no systematic error (i.e., the system is in control), a value of 1 means a 1 SD shift from the target value, etc. On the RE scale, a value of one indicates that the analytic imprecision is one multiple of the in-control imprecision, a value of 2 indicates that the stable analytic imprecision has doubled so that it is now twice what it should be when the system is in control, etc. Because the RE scale represents multiples of the SD for random error, an RE of 1 means in-control (i.e., RE=1 indicates that the out-of-control imprecision is equal to the in-control imprecision). RE=2 indicates that the out-of-control imprecision is two times the in-control imprecision. It should be noted that the SE scale ranges from 0 to 6 and the RE scale ranges from 1 to 6.

Figure 10:
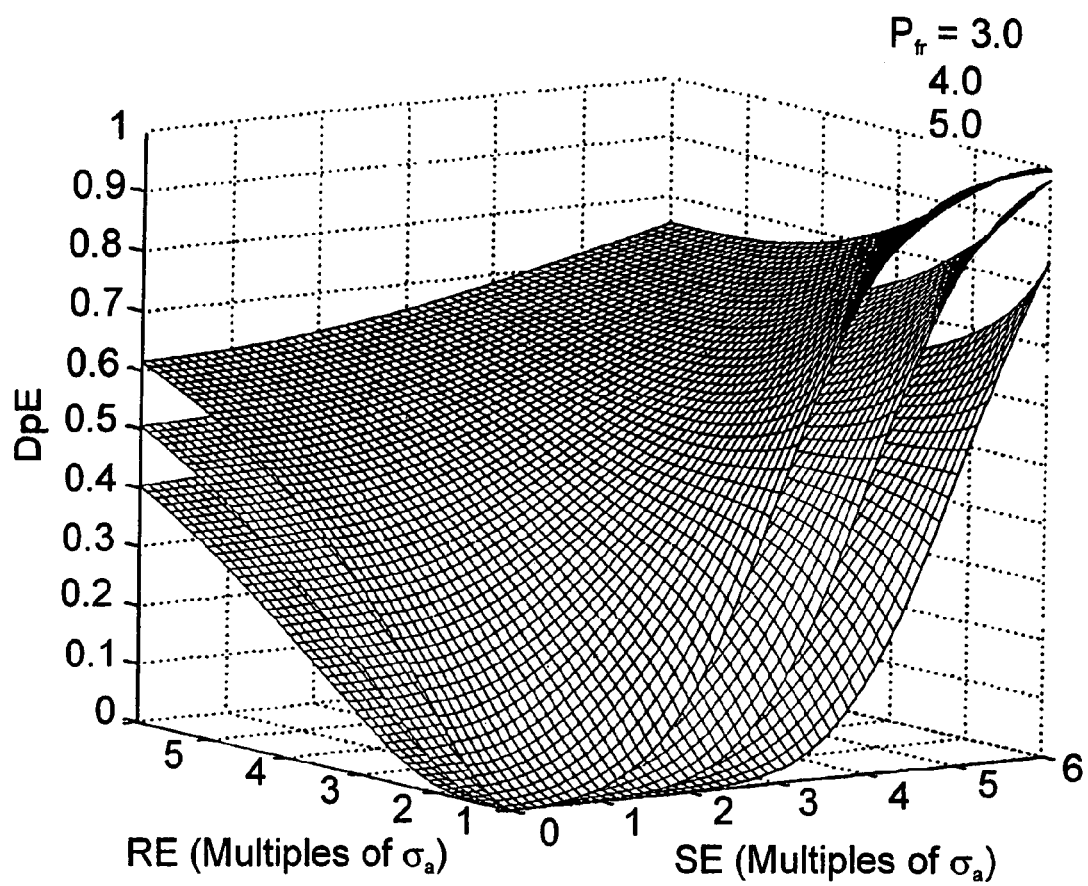
FIG. 10 shows the increase in the probability of producing a "bad" result (dpE) due to an out-of-control error condition, where a "bad" result is defined as a result with an error that exceeds total allowable error specification ($TE_a$), according to one embodiment.

FIG. 10 shows the increase in the probability of producing a "bad" result (dpE) due to an out-of-control error condition, where a "bad" result is defined as a result with an error that exceeds total allowable error specification ($TE_a$), according to one embodiment. The probability of a "bad" result depends on the magnitude of the out-of-control error condition (SE, RE) and on the total allowable error condition. The dpE decreases as the $TE_a$ increases. For example, when $TE_a$=3, the likelihood of producing a bad result is greater than when $TE_a$=6.

Evaluating the X Bar/S Rule

According to one embodiment, a single $\bar{X}$/S rule is preferably used. In certain aspects, an $\bar{X}$ rejection limit of 2.43 and an S rejection limit of 3.53 are used to obtain a 1 in 1000 probability of rejection. It should be understood that other rejection limits may be used. To evaluate the $\bar{X}$ value, according to one embodiment, z scores for each of the two QC values are created and averaged. An average z score with absolute value greater than 2.43 is a rejection. To evaluate the S value, the SD of the two z scores is calculated and an SD greater than 3.53 is a rejection.

When choosing a QC rule to use after an "event", it is desirable to minimize the worst-case probability of producing "bad" results because of an error-condition associated with the "event". The probability of producing "bad" results subsequent to an "event" is a function of the probability of producing "bad" results because of the error condition (see FIG. 10) and the probability of failing to detect the error condition (see FIG. 9).

FIG. 11 shows the probability of error detection for a particular QC rule. The surface shown in FIG. 11 generally depends on the QC rule being used to evaluate data points, the rejection limits, and the number of QC samples tested.

Figure 12:
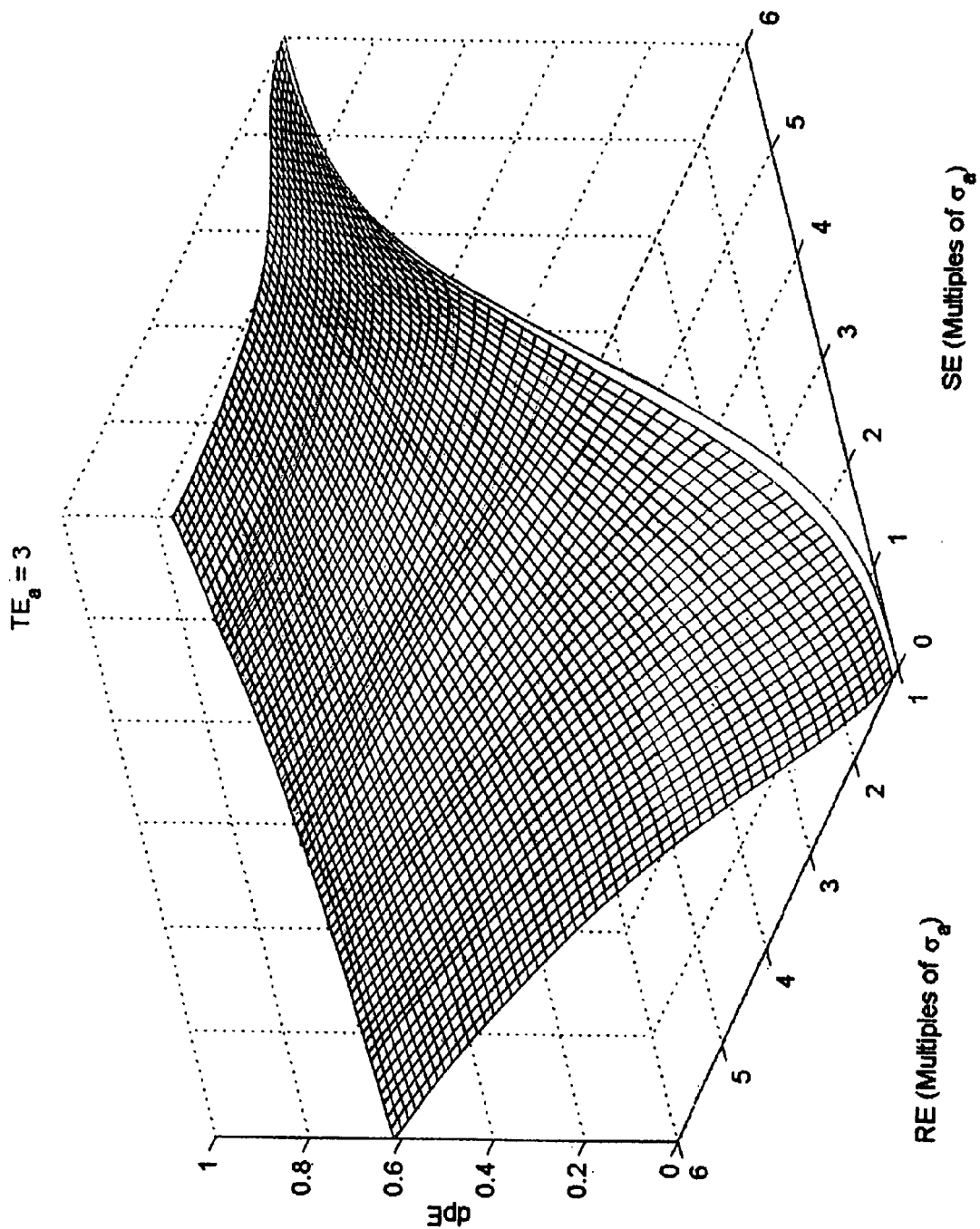
FIG. 12 shows the probability of producing "bad" results according to one embodiment. This "surface" depends on the total allowable error specification ($TE_a$).

FIG. 12 shows the probability of producing "bad" results. This "surface" depends on the total allowable error specification ($TE_a$). FIG. 12 shows the probability of producing "bad" results (dpE) with a total allowable error specification ($TE_a$) of 3. The $TE_a$ determines the surface of the plot. The surface does not depend on the rule.

FIG. 13 shows the probability of producing "bad" results if this QC rule is used after an "event". FIG. 13 is the product of FIGS. 11 and 12. More specifically, FIG. 13 shows the probability of producing "bad" results (pQE) when the QC rule Xbar(2.43)/S(3.53) is used after an "event." pQE is equal to the increase in the probability of producing "bad" results because of the error condition times the probability of failing to detect the error condition: pQE=dpE*(1−ped). The maximum point on the surface in FIG. 13 (an arrow indicates this maximum point) is at an error condition that produces a shift of 2.04 in-control analytical SDs from target and an increase in analytical SD to 2.39 times its in-control level. The probability of producing "bad" results with this QC rule, if this "worst case" out-of-control error condition occurred, is 0.181. In this case, if multiple errors of this type occurred over the next year, 18.1% of results produced after the error condition would be expected to be "bad." How quickly the error condition is detected is a function of the routine testing strategy.

Using FIG. 13, therefore, the probability of producing a bad result (at every possible error condition) subsequent to an error condition that failed to detect with event-related QC testing (i.e., the pQE) can be interpreted.

Step 4 Discussion

In this step, the rejection limits of $\bar{X}$ and SD values are varied to determine the values that produce the smallest pQE. FIGS. 14 through 18 show how the pQE surface changes as the control limits for the $\bar{X}$/S rule are varied to provide more or less error detection for SE errors versus RE errors. As the $\bar{X}$ and SD values are varied, the relative power for detecting a shift in the mean or an increase in imprecision varies. These figures demonstrate that it is possible to find the rejection limits for the $\bar{X}$ and SD that produce the smallest pQE peak. For FIGS. 14 through 18, the following values are held constant:

Number of QC samples=2
$P_{fr}$=0.001
$TE_a$=3.0

Figure 16:
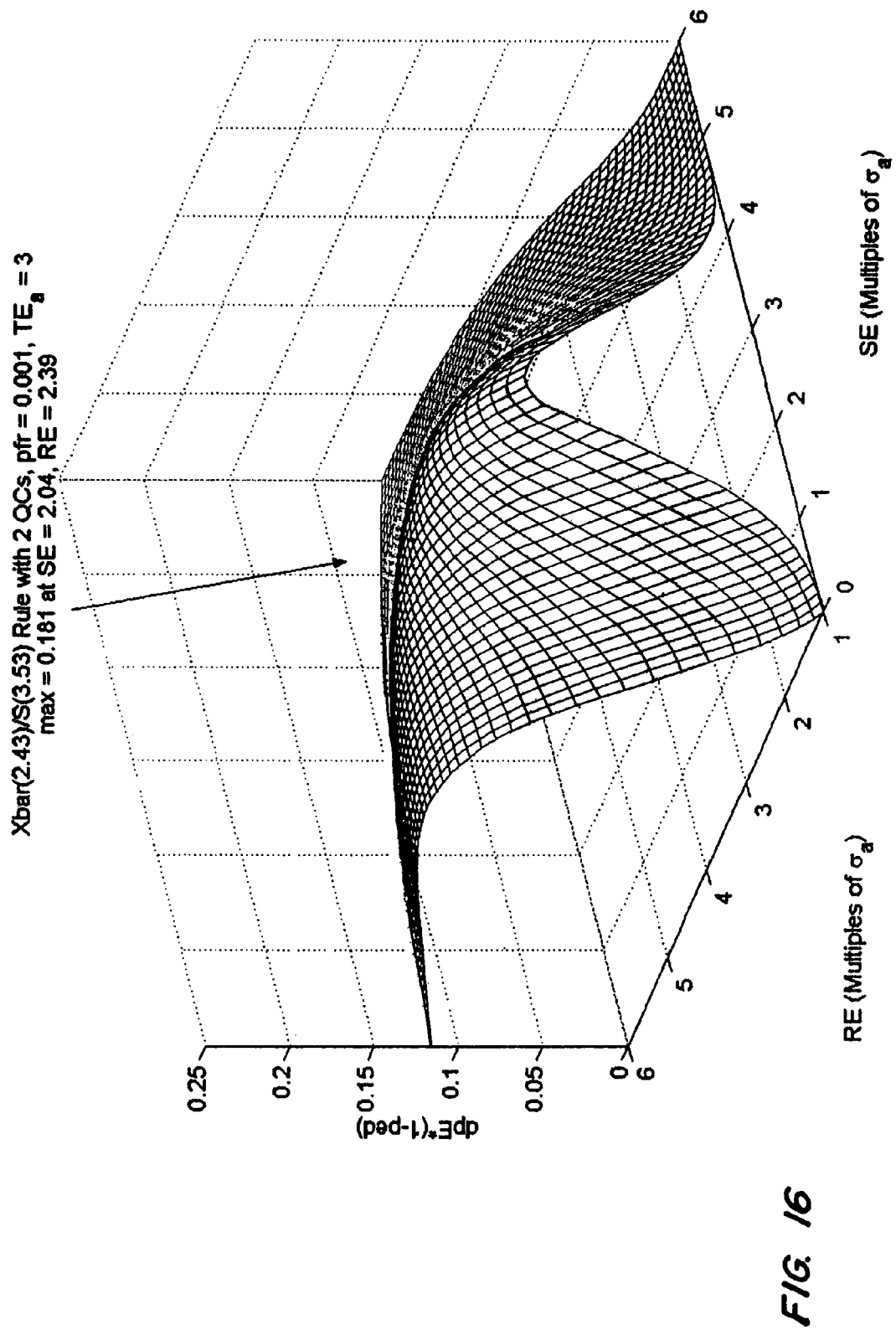
Figure 17:
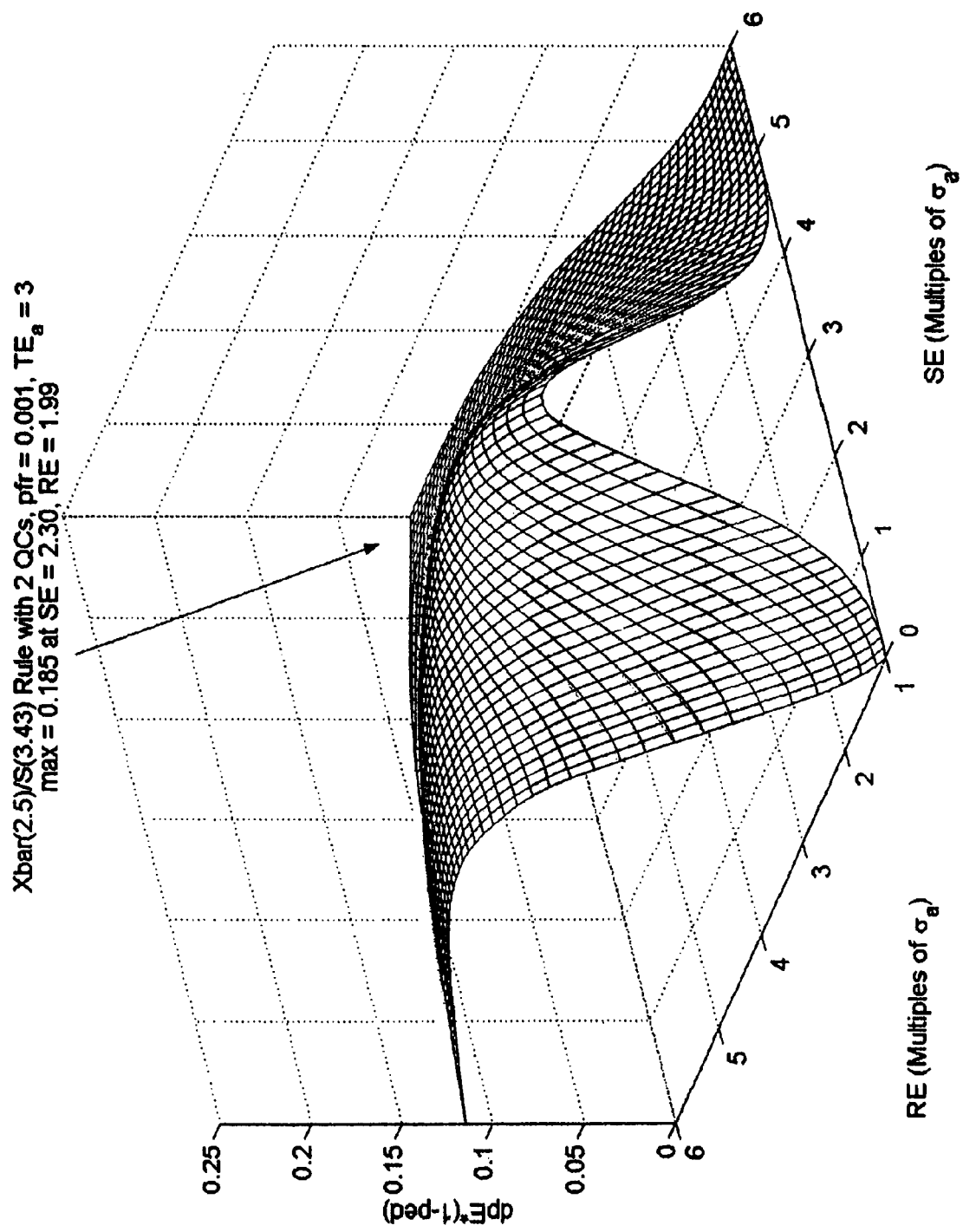
Figure 18:
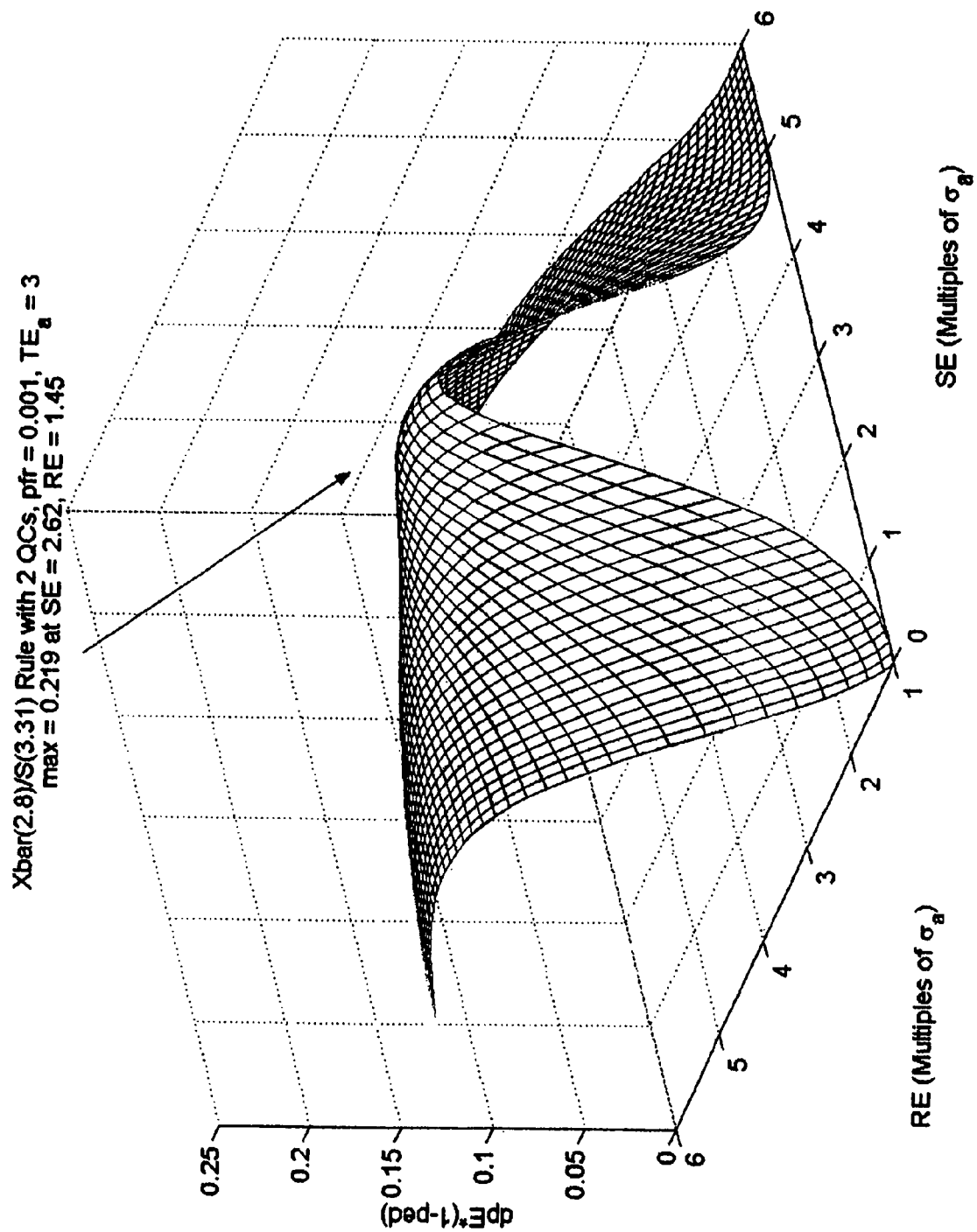
Figure 19:
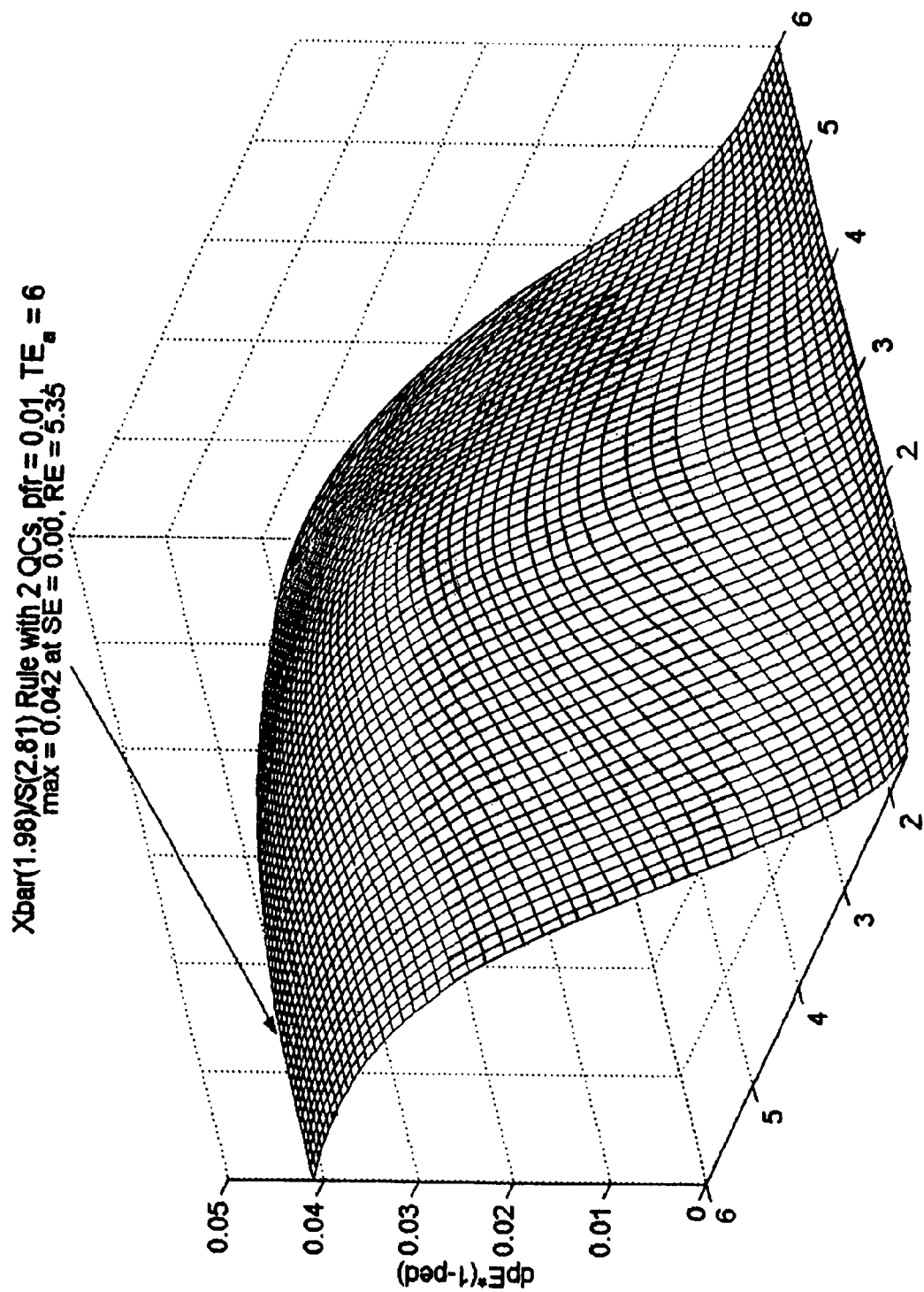
FIGS. 19-34 illustrate the number of QC samples required with the optimal combination of rejection limits for an $\overline{X}/S$ rule so that the maximum probability of producing a "bad" result after QC testing is less than or equal to 0.05 (5%) for the false rejection rates $p_f$=0.01, 0.005, 0.002, 0.001, and total allowable error specifications $TE_a$=3, 4, 5, 6, according to one embodiment.
Figure 20:
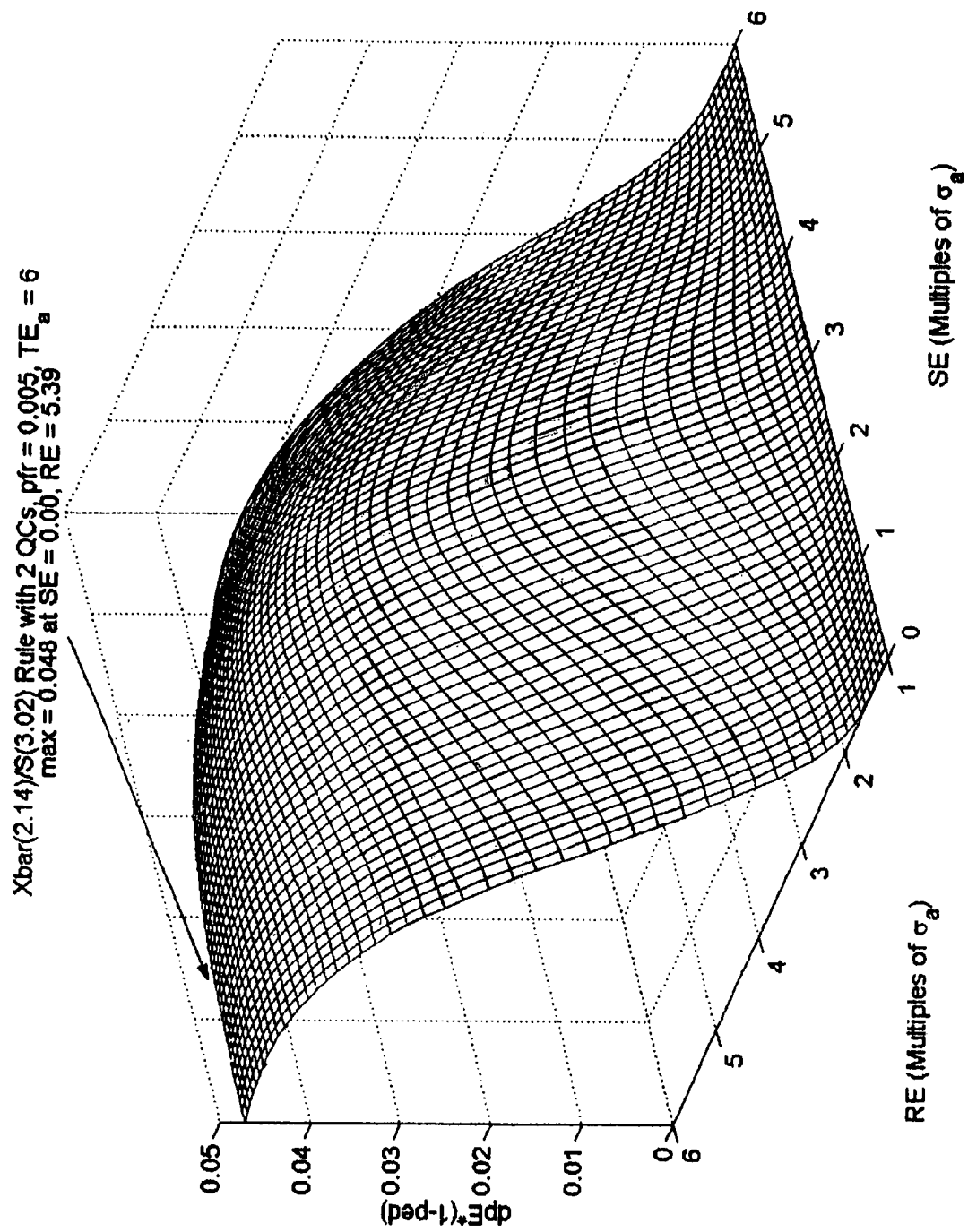
Figure 21:
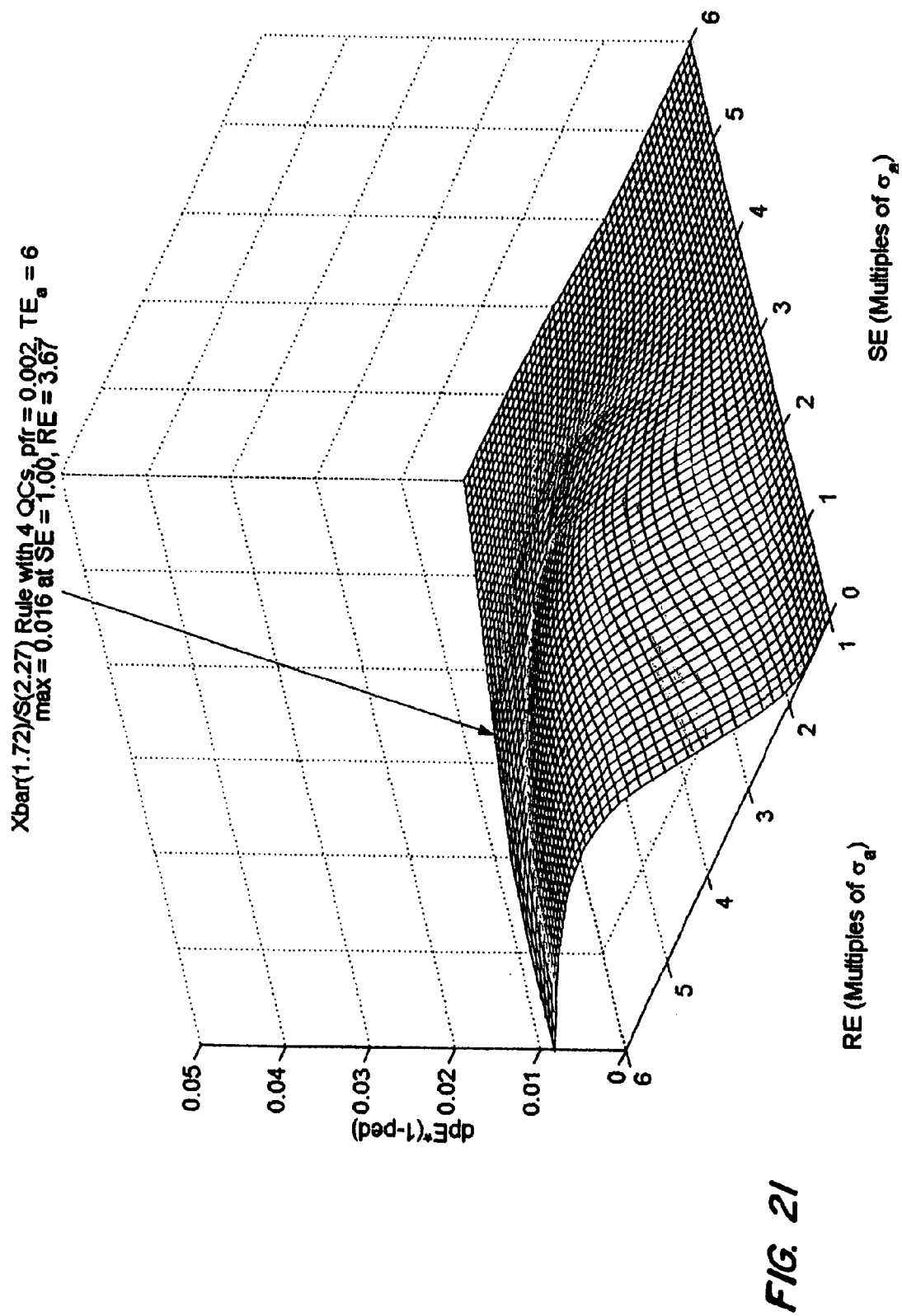
Figure 22:
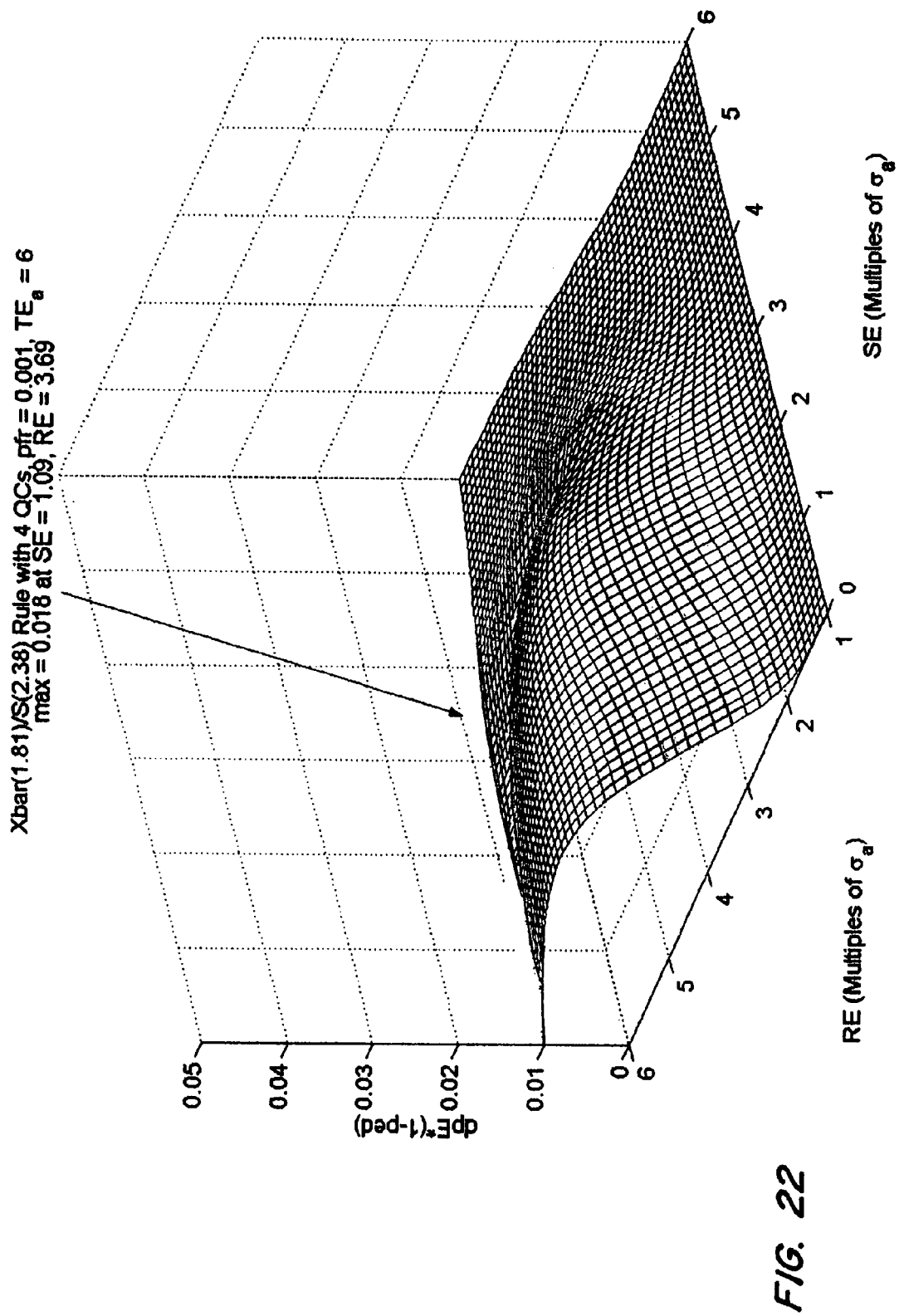
Figure 23:
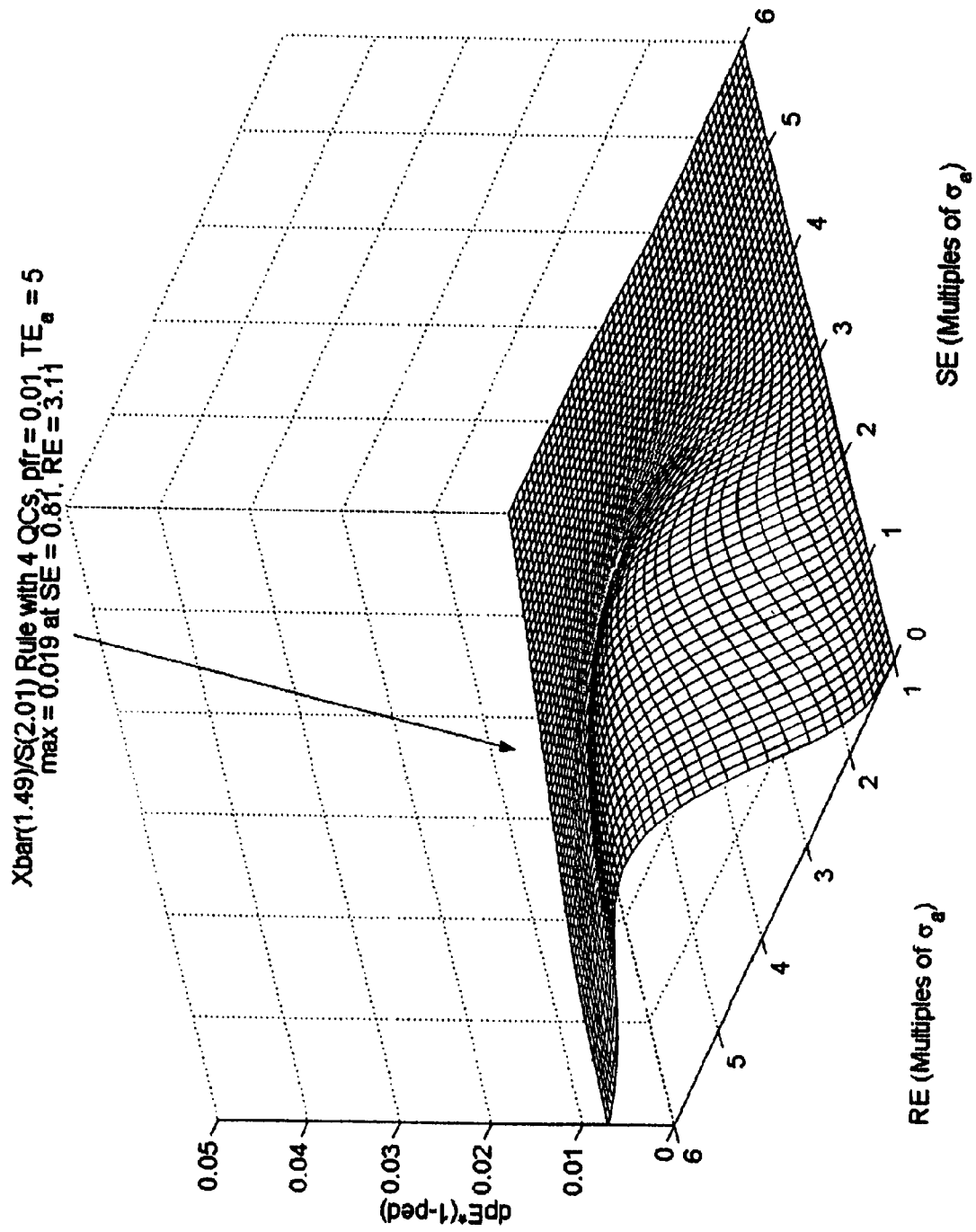
Figure 24:
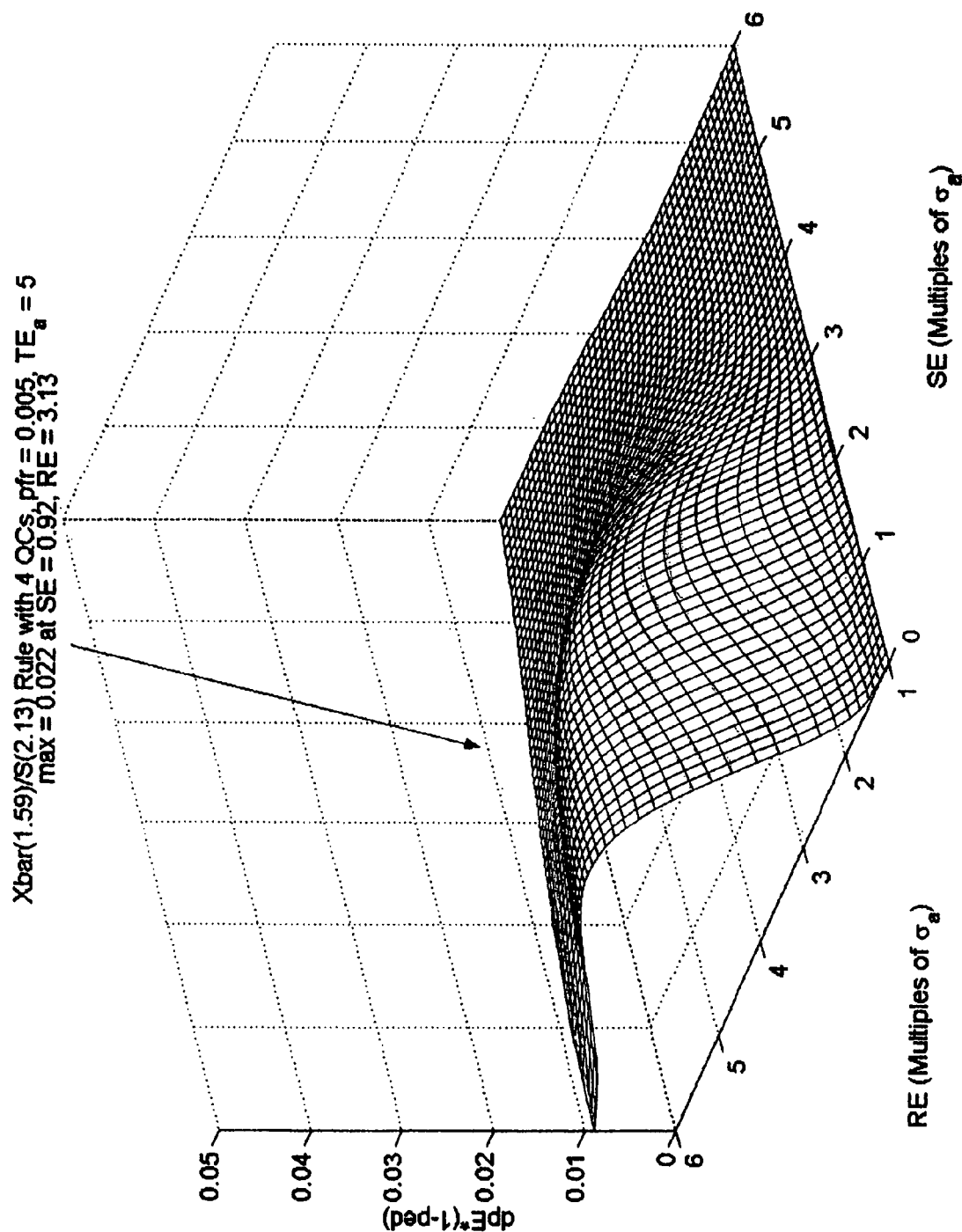
Figure 25:
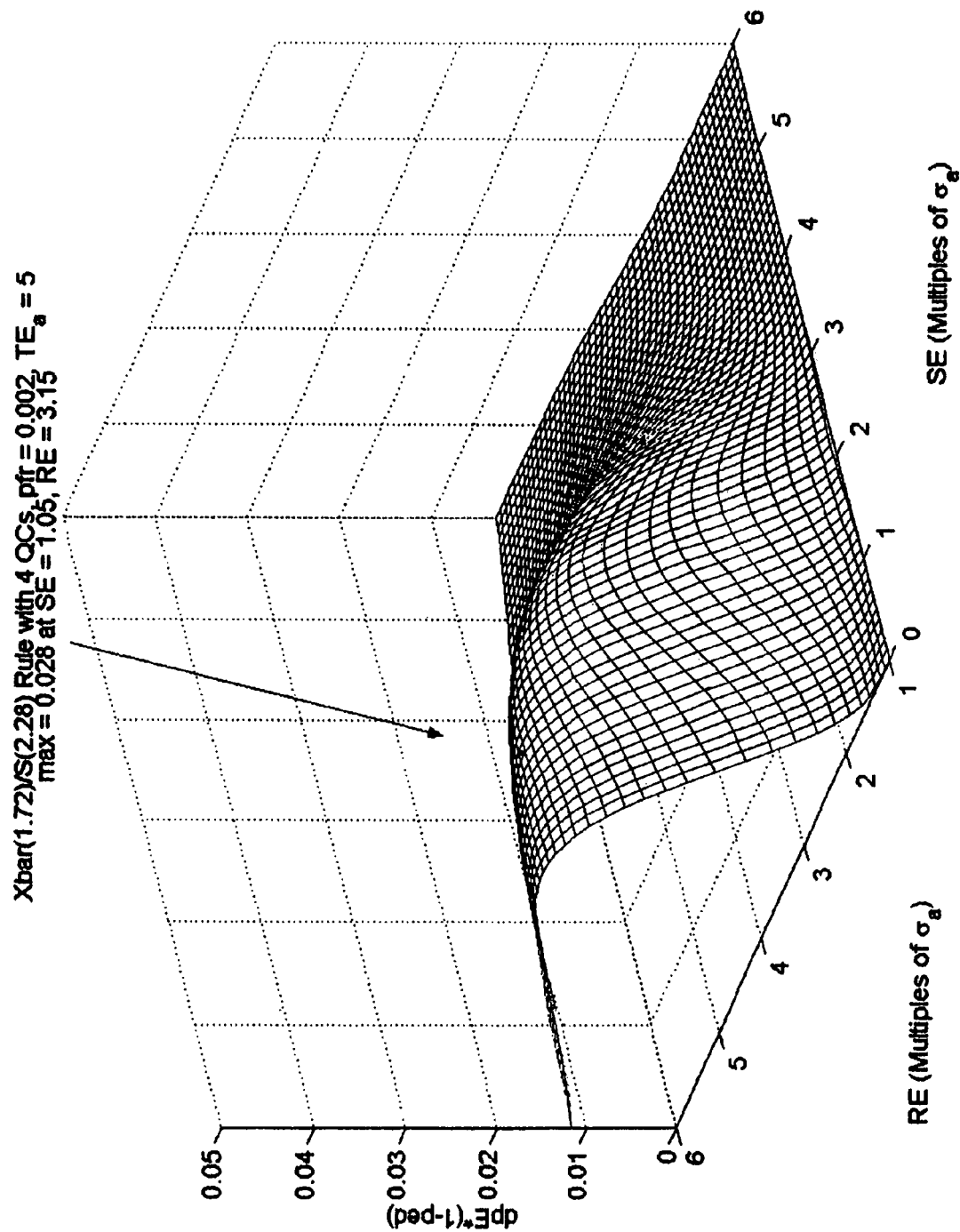
Figure 26:
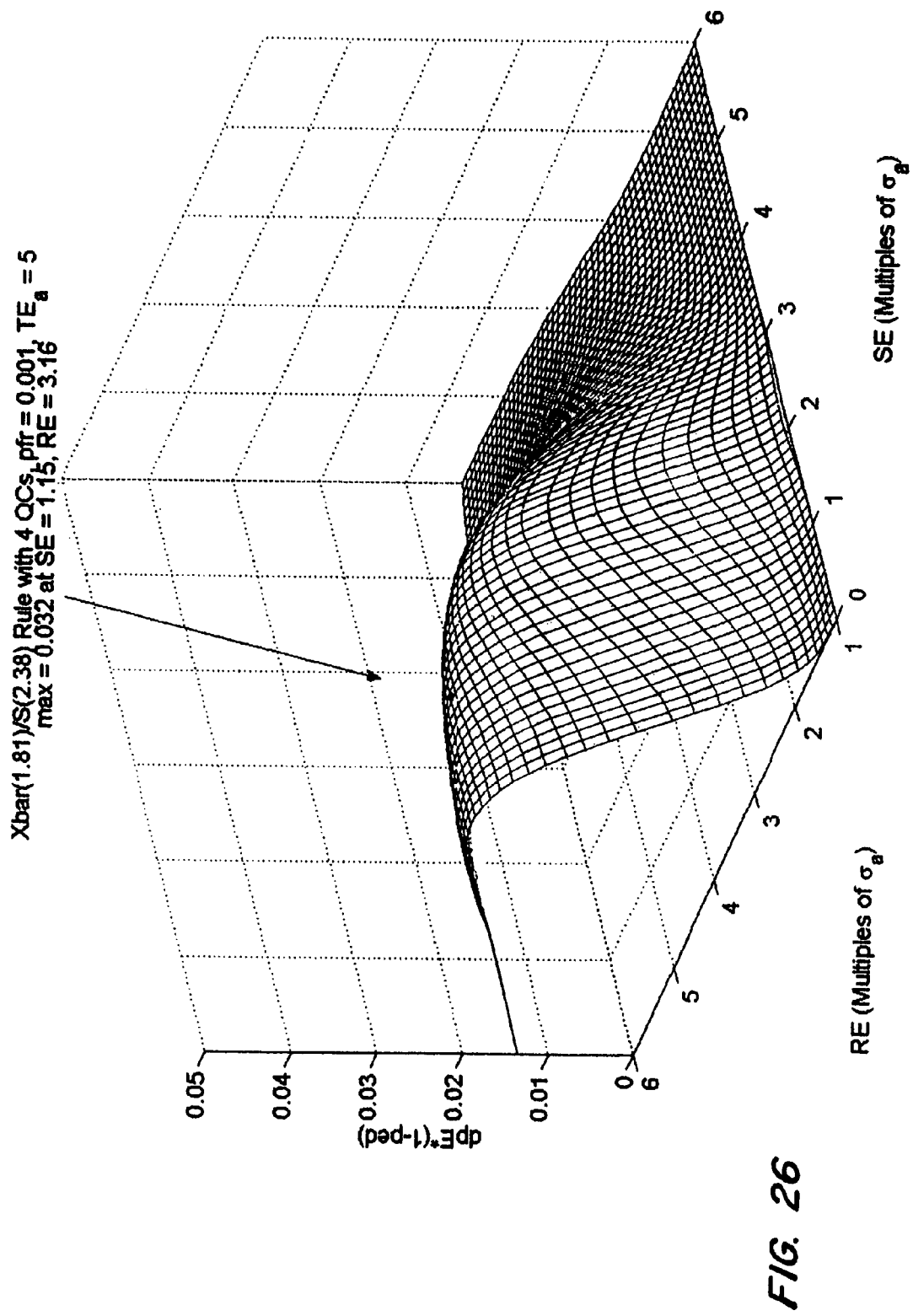
Figure 27:
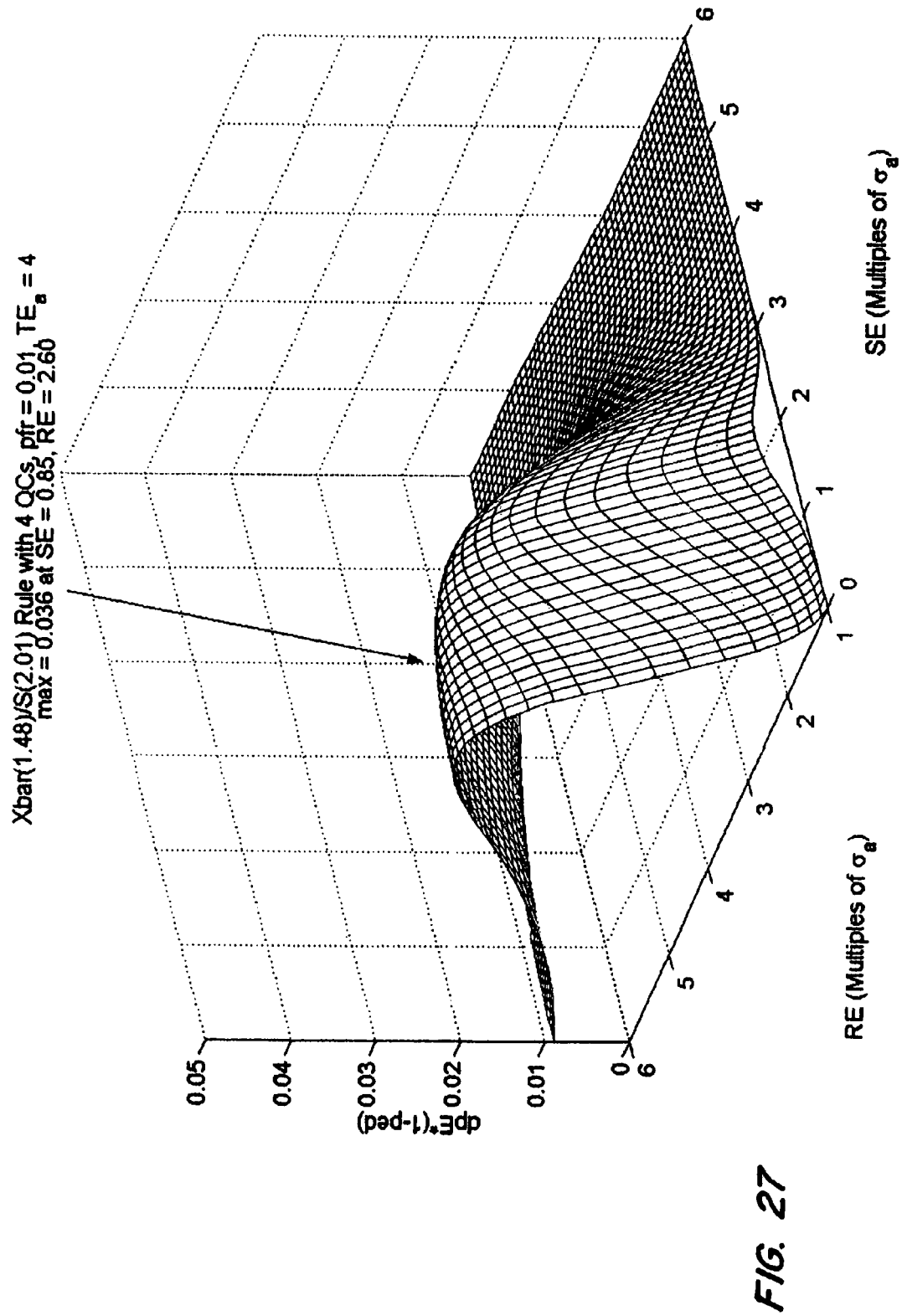
Figure 28:
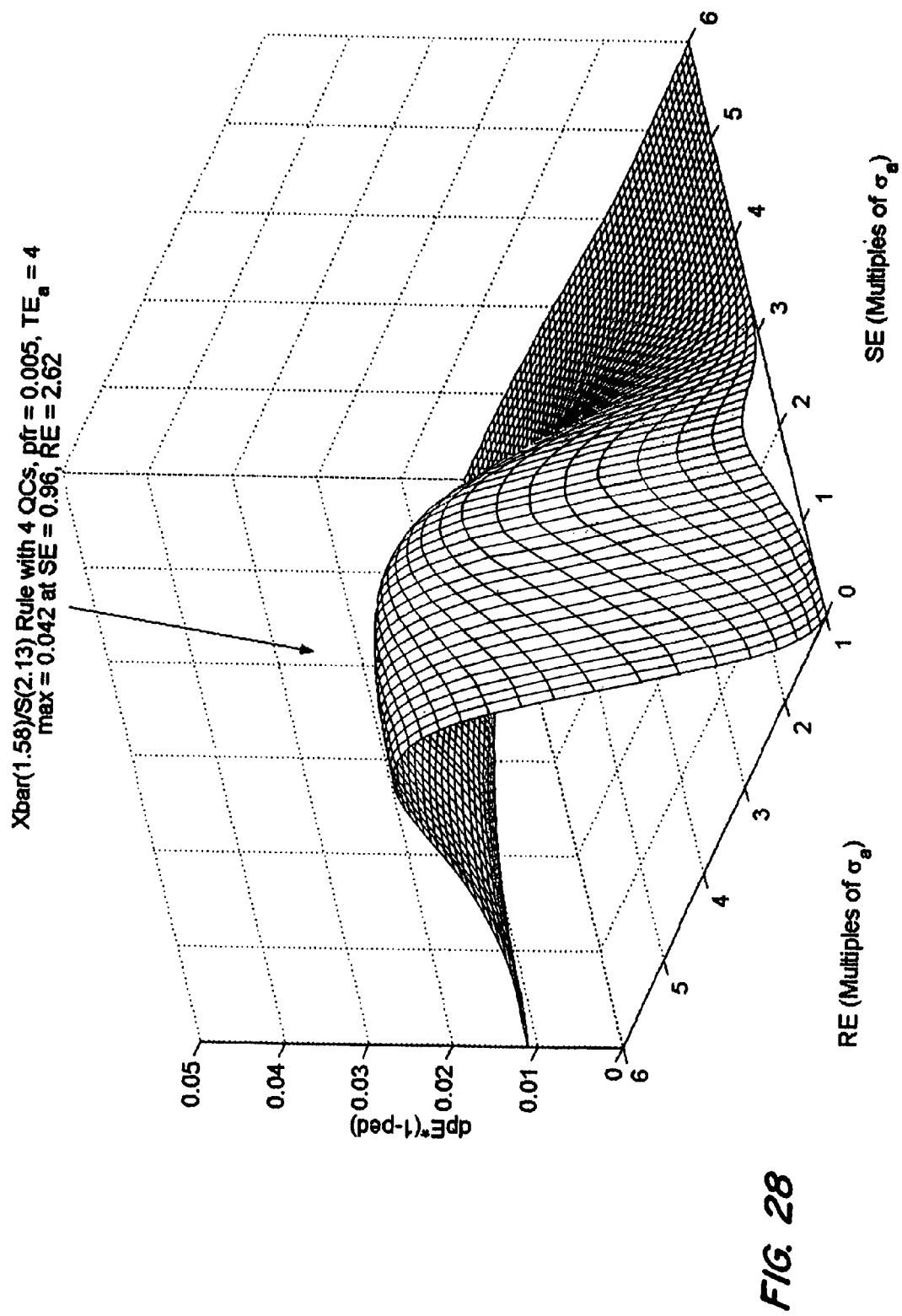
Figure 29:
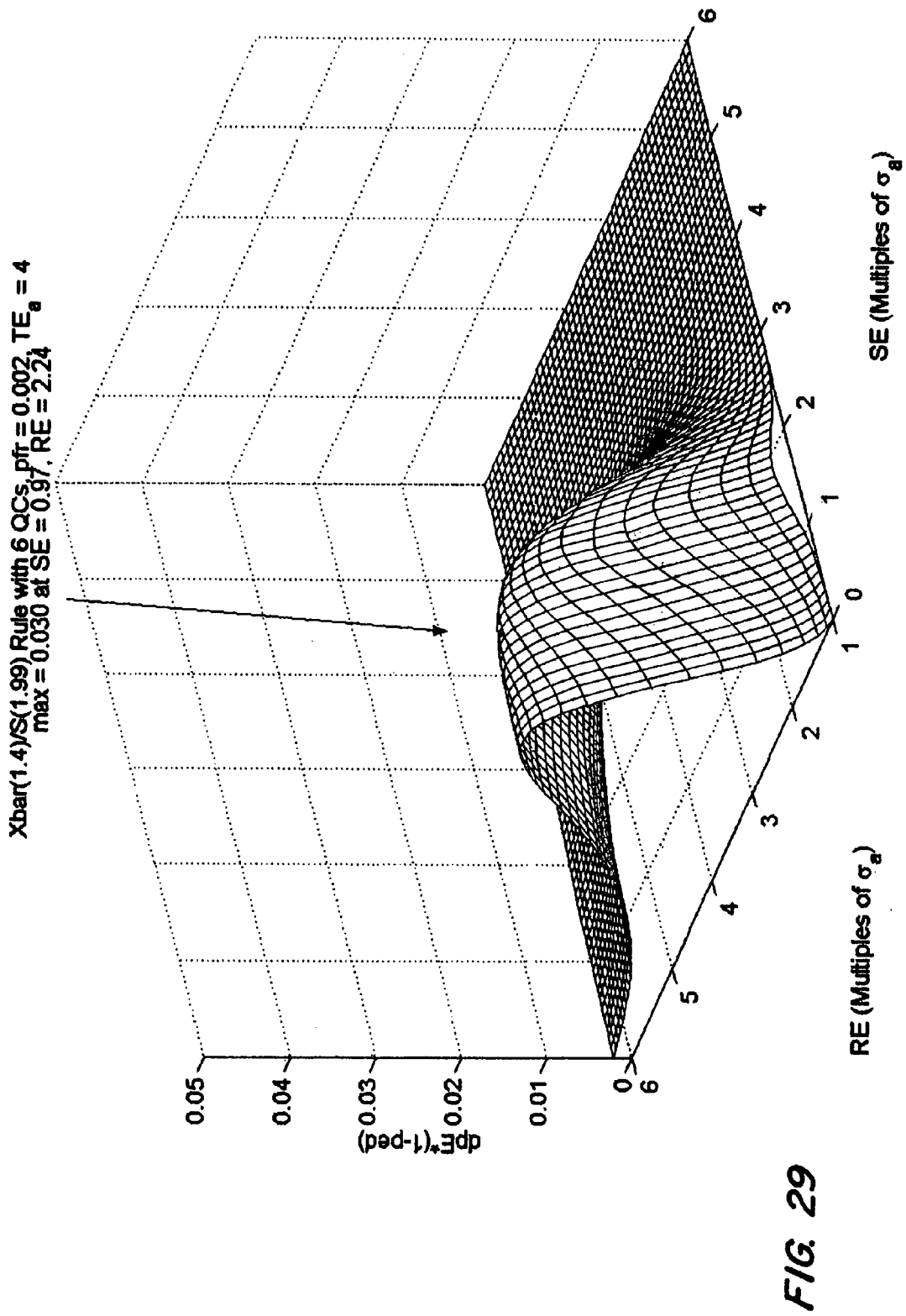
Figure 30:
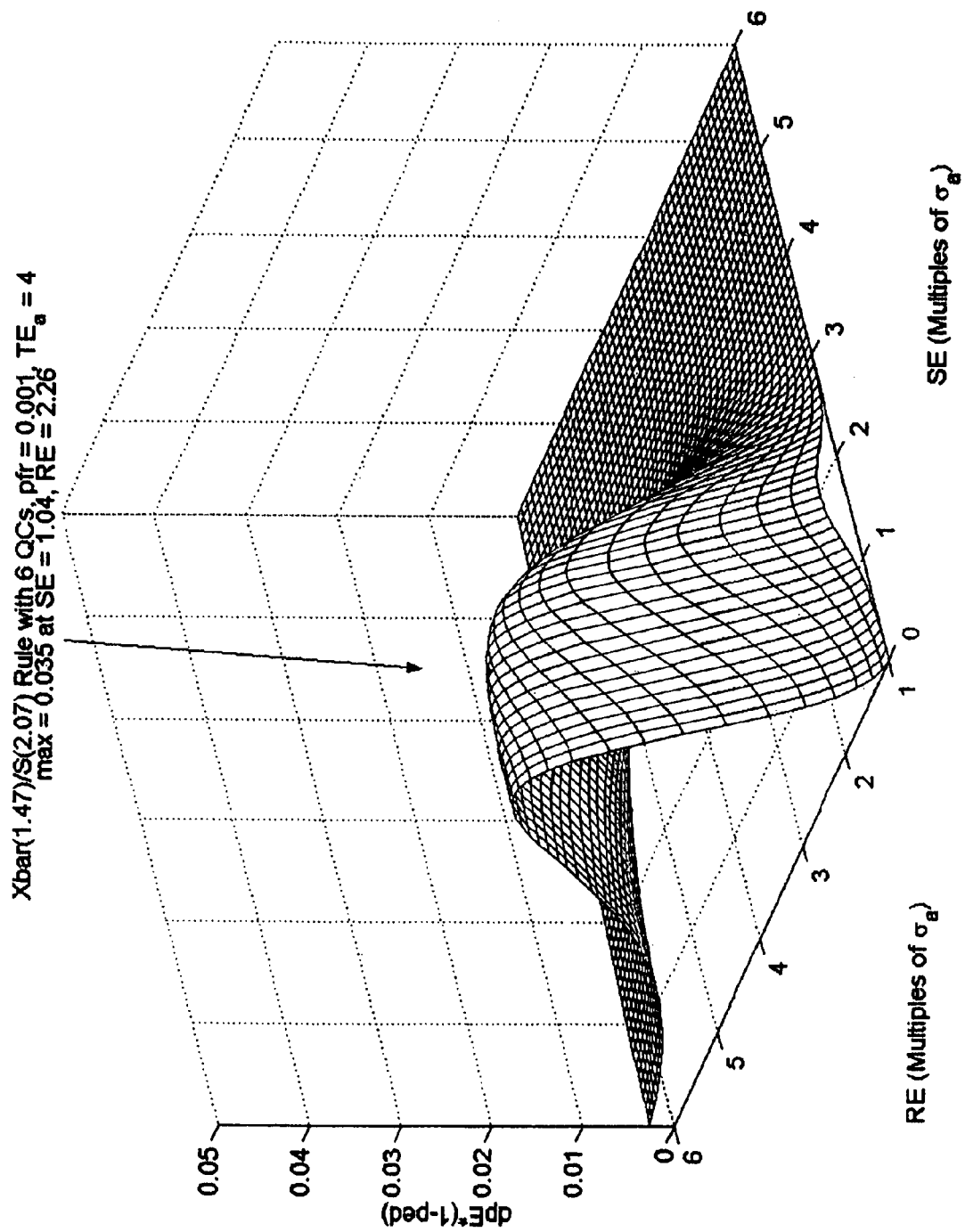
Figure 31:
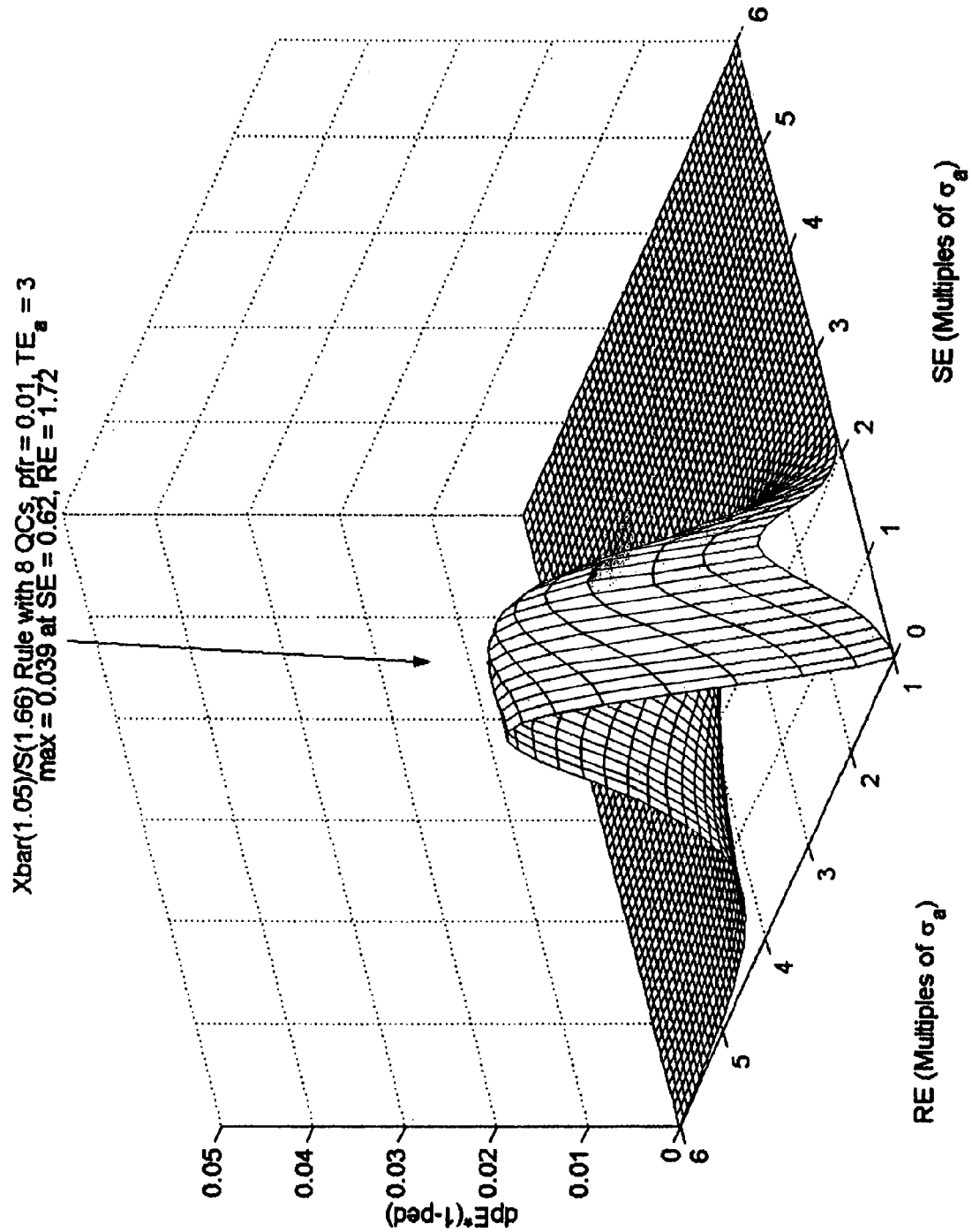
Figure 32:
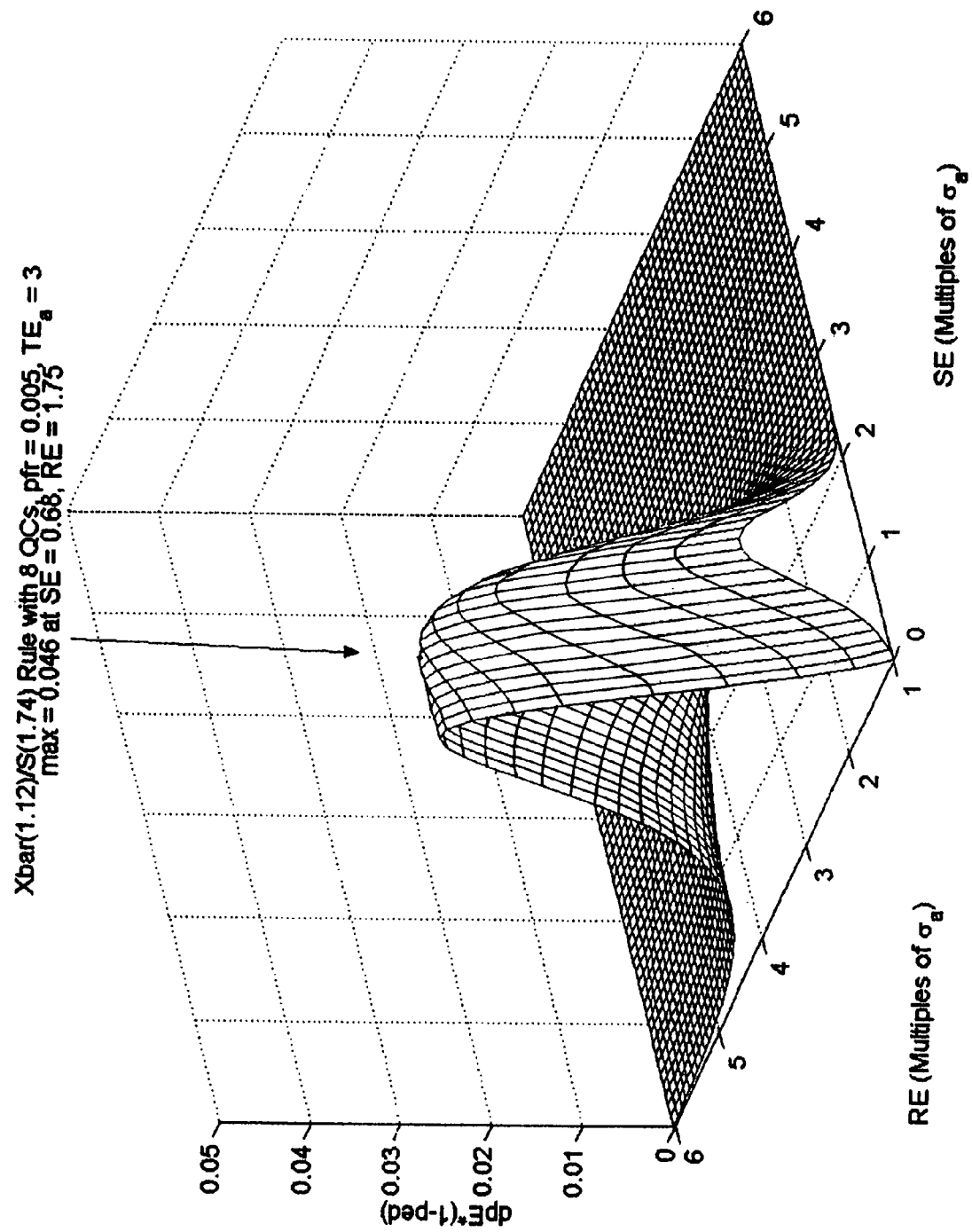
Figure 33:
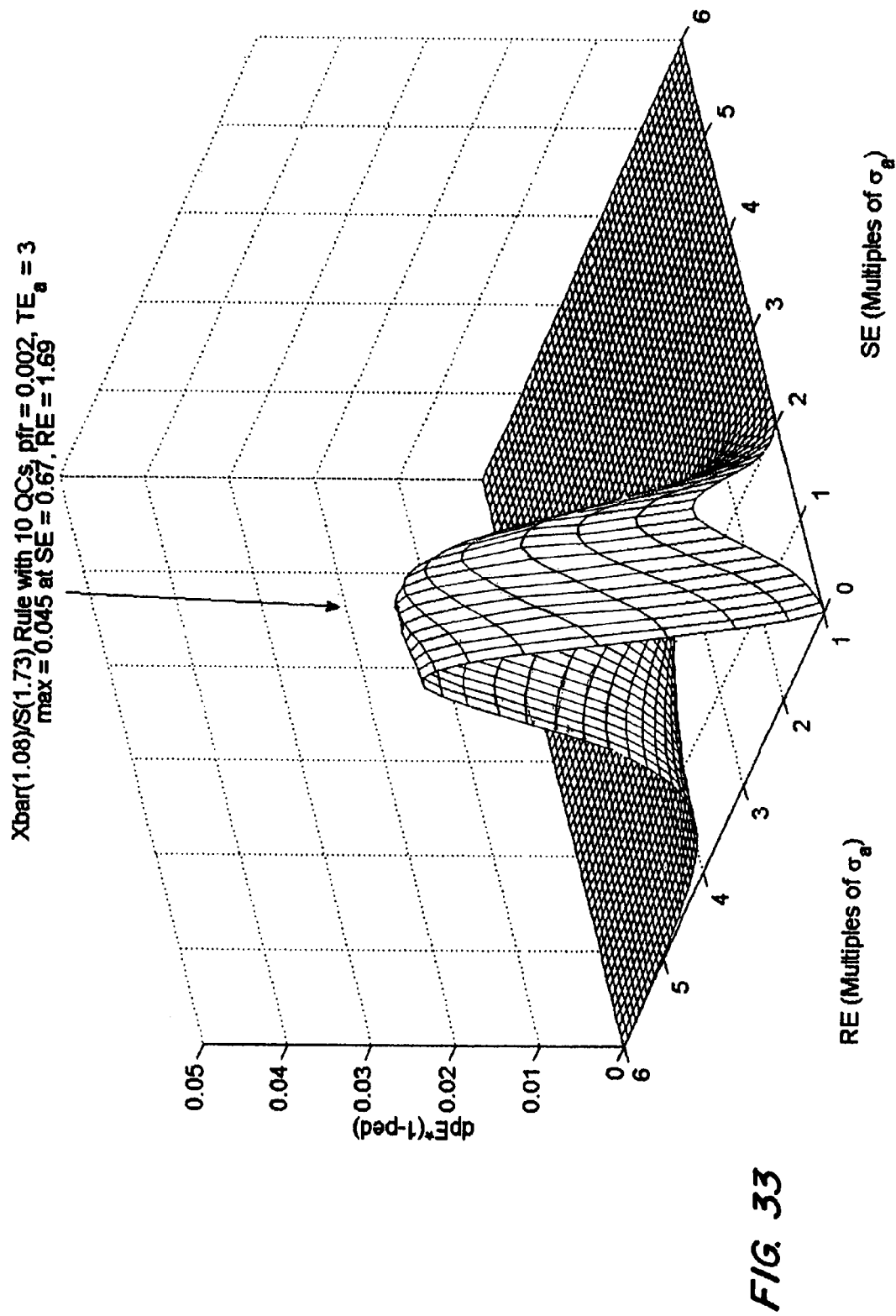
Figure 34:
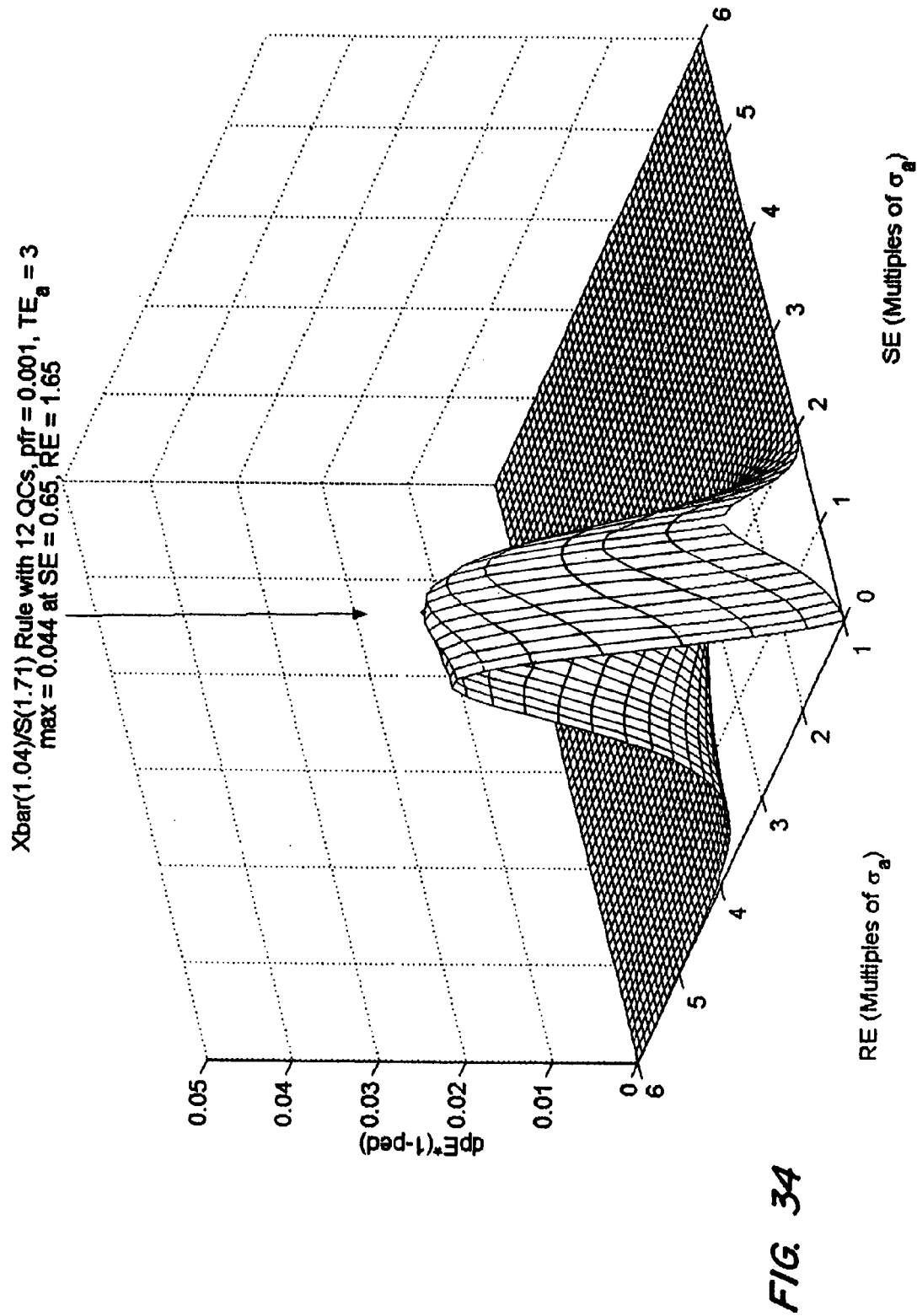

Table 1 summarizes the conclusions drawn from FIGS. 14-18. Note that FIG. 16 shows the rejection limits that minimize the maximum point on the surface. (i.e., it has the smallest peak.)

| FIG. | Xbar | SD | Max. Peak | SE | RE |
| --- | --- | --- | --- | --- | --- |
| 14 | 2.33 | 4.31 | 0.199 | 0.00 | 3.38 |
| 15 | 2.37 | 3.72 | 0.184 | 0.00 | 3.29 |
| 16 | 2.43 | 3.53 | 0.181 | 2.04 | 2.39 |
| 17 | 2.50 | 3.43 | 0.185 | 2.30 | 1.99 |
| 18 | 2.80 | 3.31 | 0.219 | 2.62 | 1.45 |

Step 5 Discussion

In step 4 the rejection limits are varied to determine the optimum number of QC samples to minimize the pQE. In step 5, the $\bar{X}$ and S rejection rates and the number of QC samples are varied over a range of total allowable error specifications ($TE_a$) and false rejection rates ($p_{fr}$) to determine the pQE that never exceeds a desired value, e.g., 5%., regardless of the error condition. FIGS. 19 through 34 are useful for determining the optimal combinations of $\bar{X}$ and SD at different false rejections rates and total allowable error specifications. In particular, according to one embodiment, FIGS. 19-34 illustrate the number of QC samples required with the optimal combination of rejection limits for an $\bar{X}$/S rule so that the maximum probability of producing a "bad" result after QC testing is less than or equal to 0.05 (5%) for the following false rejection rates (pf) and total allowable error specifications ($TE_a$):

$p_{fr}$=0.01, 0.005, 0.002, 0.001

(The run length for these $p_{fr}$ values are 100, 200, 500, and 1000, respectively.)

$TE_a$=3, 4, 5, 6

Restrictions placed on the model as illustrated in FIG. 19-34 include:

The probability of producing a "bad" result (pQE) after QC testing can never be greater than a 5% irrespective of the error condition. The choice of 5% is arbitrary; however, it means that the vertical scale representing pQE=dpE*(1−ped) is never greater than 0.05.

The number of QC samples tested (N) is limited to multiples of 2, based on the assumption that two concentration levels of QC are typically tested and that both levels are represented equally.

Total allowable error specifications ($TE_a$) of 3, 4, 5, and 6 were considered. In general, a third party, such as CLIA, determines the $TE_a$ specifications. $TE_a$ specifications based on biological variation and published by Ricos' group in the Scandinavian Journal of Clinical Lab Investigation are much smaller than the CLIA $TE_a$ specifications. (See, e.g., Ricos, C. et al. Current Databases on Biological Variation. Scand J Clin Lab Invest 1999; Vol 59 No. 7 491-500).

False rejection rates ($p_{fr}$) of 0.01, 0.005, 0.002, 0.001 were considered. The scale remains the same for all charts to make changes to the surface from chart to chart easier to perceive. In addition, the pQE=dpe*(1−ped) scale is never larger than 0.05, because the maximum pQE was set to 5%.

Using the present invention, the number of QC samples required after an event can be determined by varying total allowable error specifications ($TE_a$) and false rejection rates ($p_{fr}$). If event-related QC fails to detect the out-of-control error condition, how long the error condition will persist and, consequently, the number of bad results reported will be a function of the routine QC testing strategy and will depend on the average number of patient samples to error detection ($ANP_{ed}$). (See, e.g., Ye, Jay et. al. Performance Evaluation and Planning for Patient-Based Quality Control Procedures. Amm J Clin Pathol 2000:113:240-248).

The expected number of bad results due to the event is equal to the pQE surface multiplied times the $ANP_{ed}$. For example, if the $ANP_{ed}$ is 20 and the pQE is never allowed to exceed 5%, the expected number of bad results will never exceed 20*0.5 or 1 bad result, which is probably acceptable. However, if the $ANP_{ed}$ is 200, the expected number of bad results will be 10. Whether or not this is acceptable depends on factors such as the probability of this error condition occurring. For example, if the "event" is daily instrument maintenance and the $p_{fr}$ is 1:500, then the likelihood of a $p_{fr}$ associated with daily maintenance is less than once a year. Because the cost of a $p_{fr}$ is probably high, labs will probably want to make the $p_{fr}$ as small as possible. ($p_{fr}$ costs generally include running additional QC samples, additional maintenance, delay in reporting patient results, etc.)

From the above, it can be seen that 4 QC samples (2 each at 2 concentration levels) are adequate to meet the criterion that the worst-case probability of producing "bad" results doesn't exceed 5%, except for relatively small total allowable error specifications ($TE_a$<4), even with the false rejection probability as low as 0.001. If the 5% criterion is lowered, the required Ns will increase. For the "toughest" case considered here (FIG. 26, $TE_a$=3 and $p_{fr}$=0.001), 12 QC samples (6 each at 2 concentration levels) are required to meet the 5% worst case probability of producing "bad" results after QC testing criterion. Using a $TE_a$ of 6 requires a fairly large error condition before the system begins producing "bad" results.

FIGS. 19-34 can be divided into groups of four as shown in Table 2, where:

TABLE 2

| FIG. | $TE_a$ | $p_{fr}$ | Group |
|---|---|---|---|
| 19 | 6 | 0.01 | Group 1 |
| 20 | 6 | 0.005 | |
| 21 | 6 | 0.002 | |
| 22 | 6 | 0.001 | |

TABLE 2-continued

| FIG. | $TE_a$ | $p_{fr}$ | Group |
|---|---|---|---|
| 23 | 5 | 0.01 | Group 2 |
| 24 | 5 | 0.005 | |
| 25 | 5 | 0.002 | |
| 26 | 5 | 0.001 | |
| 27 | 4 | 0.01 | Group 3 |
| 28 | 4 | 0.005 | |
| 29 | 4 | 0.002 | |
| 30 | 4 | 0.001 | |
| 31 | 3 | 0.01 | Group 4 |
| 32 | 3 | 0.005 | |
| 33 | 3 | 0.002 | |
| 34 | 3 | 0.001 | |

Supplemental Sampling QC Procedure

According to one embodiment, the system is configured so that It is also possible to set the number of QC samples tested to a continuous value. This allows N to range from 2 to any number. In one embodiment, this is done using a 2 stage testing approach: initially test 2 QC samples and depending on the values of these 2 samples either accept and assume that the testing system is okay and immediately test additional QC samples. For example, the first 2 QC samples are not accepted and 2 additional samples are immediately tested, a QC rule based on the 4 samples combined is needed. In this case, the number of QC samples tested is a random variable based on whether the first pair of QC samples is accepted or rejected. Using this strategy, it is possible to determine the smallest N that results in a pQE of, e.g., exactly 0.05. It is fairly common practice in the laboratory to repeat out-of-range control samples, and if the repeat controls are within range, to accept them and continue testing.

Such an approach has been disparaged in the past, based mainly on comments by Dr. Westgard which stressed that repeating QC samples is not improving the lab's QC, but rather is lowering the false rejection probability and error detection ability. This is only correct if the rejection limits for the two QC tests are not adjusted so that the overall false rejection probability remains as desired. If the QC rules applied to the first and second set of QC samples, and the false rejection probability associated with the first and second samples are both allowed to vary then this approach is more powerful than just testing a single set of QC samples.

This supplemental approach has several advantages over the mean/range ($\overline{X}$/S) rule. For example, it will generally provide better results, on average, than the mean range rule at detecting error when using the same number of QC samples. Additionally, it is advantageous to have the flexibility to set the number of QC samples to any number. This is particularly useful with tri-level controls where the number of QC samples are in multiples of 3.

Bracketing Batch Data at a Determined Frequency

In another exemplary embodiment and methodology of the present invention, a method of optimizing QC evaluation in batch-type quality control systems while minimizing the number of quality control samples required is provided. As previously described, using the $ANP_{TE}$ performance metric (average number of patient results with an unacceptable total error) to establish a minimum acceptable error is useful when using open-ended, non-bracketed quality control methods, such as when using patient data as a control. However, the $ANP_{TE}$ metric is directly related to the frequency of control testing, thus running controls more frequently always results in a lower $ANP_{TE}$, making the metric less useful in batch processing.

As will be explained in more detail hereinbelow, using a new metric, the expected number of unacceptable results reported $E(N_U)$, an optimum batch size $E(N_B)$ can be determined to set bounds, or "brackets" for determining how frequently controls should be run during processing of a stream of patient samples. The determined frequency of brackets sets an effective batch size of patient data to run between each control. For example, if a desired $E(N_U)$ results in an optimum batch size $E(N_B)$ of thirty, then brackets are set to run controls at a frequency of every thirty patient data samples. Running controls at the determined frequency results in the desired expected number of unacceptable results reported $E(N_U)$ using a minimum number of quality control material.

Figure 35:
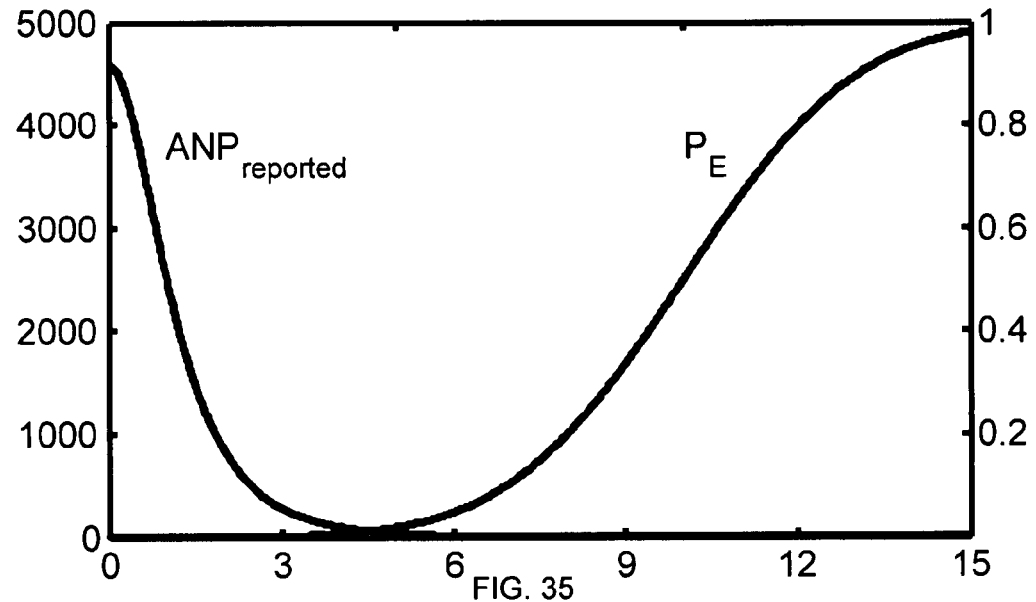
FIGS. 35-38 illustrate the calculation of an optimum batch size for a desired expected number of unacceptable results $E(N_U)$ reported in accordance with an exemplary embodiment of the present invention.

Looking to FIG. 35, calculation of an expected number of unacceptable results reported $E(N_U)$ begins with a determination of the probability of producing unacceptable results due to the presence of an out-of-control condition $P_E$, and the determination of the average number of patients reported during an undetected error state ($ANP_{reported}$). As discussed previously, the probability of producing unacceptable results $P_E$ and the probability of detecting an out-of-control error $P_{ed}$ are known for various QC rules. In FIG. 35, for a Mean/Range Rule, with $N_Q=2$, the magnitude of out-of-control error expressed as a percentage state error (SE(%)) is depicted along the x-axis, with probability shown along the y-axis. As can be seen by the $P_E$ curve of FIG. 35, for small out-of-control error conditions the probability of producing a result with unacceptable error $P_E$ is small, while for large out-of-control error conditions the probability of producing a result with unacceptable error $P_E$ is large. Stated another way, the larger the out-of control error, the higher the probability of producing a result having unacceptable error.

Similarly, looking to the $ANP_{reported}$ curve of FIG. 35, for small out-of-control error conditions, the number of patients reported until detection of the error is large because the probability of not detecting the error is large, thus many control evaluations may be required before it is detected. And, for large out-of-control error conditions, the probability of not detecting the error is small, so the error will be detected at the first control evaluation, thus the number of patients reported will be small. Stated another way, the larger the out-of-control error condition, the smaller the probability of not detecting the error and the smaller the number of patients reported will be. Of course, while FIG. 35 depicts $P_E$ and $ANP_{reported}$ for a mean range rule, with $N_Q=2$, the overall shape and trend of the probability curves will be similar for any selected QC Rule where the probability of error detection remains constant between control evaluations.

Figure 36:
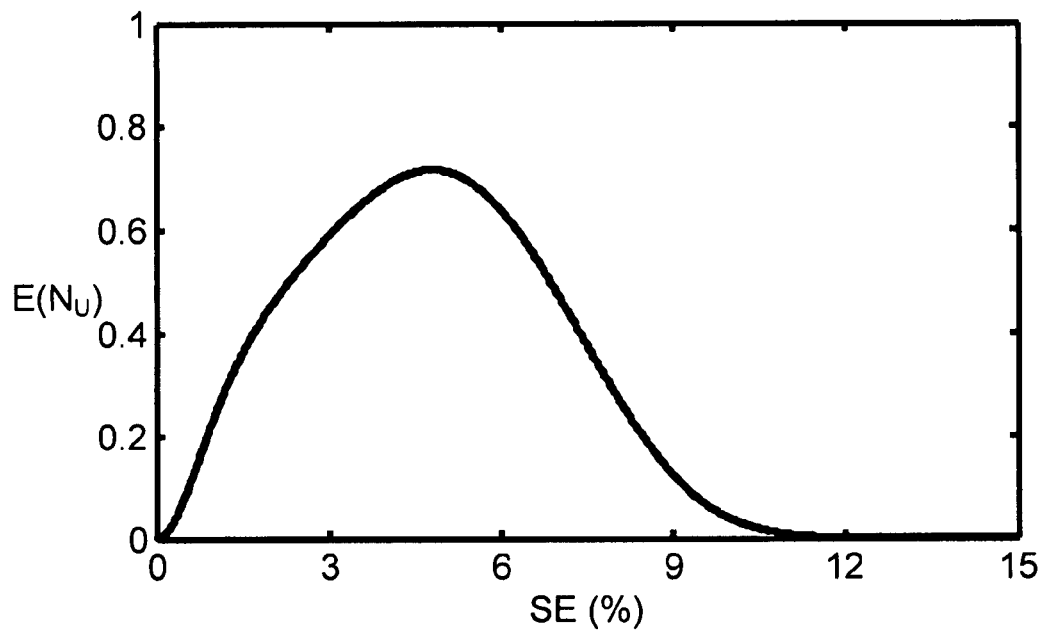

Looking now to FIG. 36, having determined $P_E$ and $ANP_{reported}$, the expected number of unacceptable results reported $E(N_U)$ is calculated by multiplying $P_E \cdot ANP_{reported}$. The $ANP_{reported}$ is computed by multiplying the average run length of an undetected error reported ($ARL_R$) by the batch size $E(N_B)$. $ARL_R$ is computed for a given QC rule by multiplying $(1-P_{ed}) \cdot (1/P_{ed} - \frac{1}{2})$. The average run length of unacceptable results reported ($ARL_U$) is calculated by $P_E \cdot ARL_R$, or $P_E \cdot (1-P_{ed}) \cdot (1/P_{ed} - \frac{1}{2})$. Thus, expected number of unacceptable results reported $E(N_U)$ is derived from both the probability of producing a result that has unacceptable error and the average number of patients reported during the error condition $ANP_{reported}$.

Figure 37:
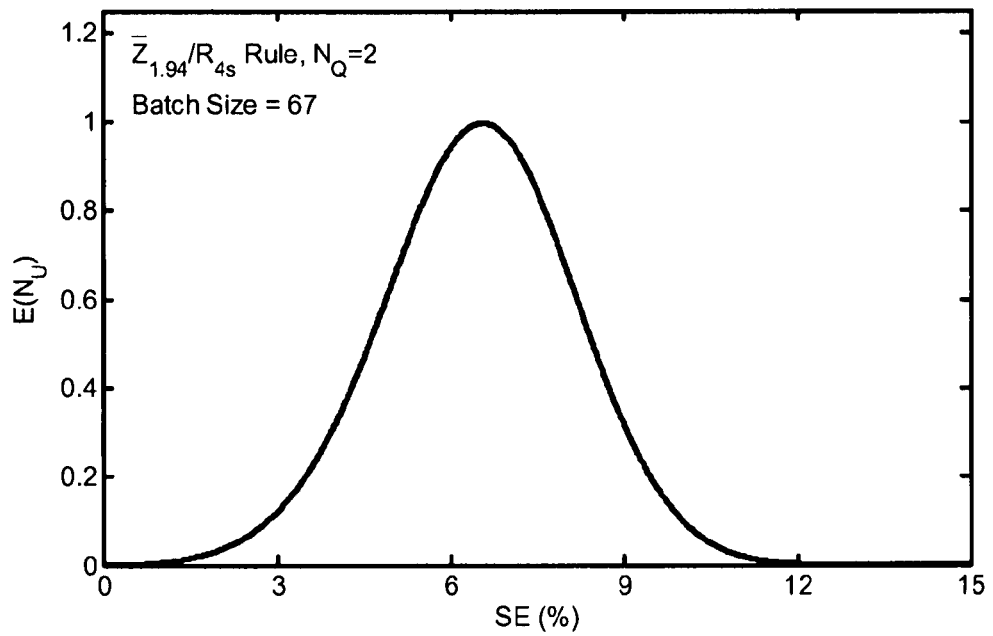

With $ARL_U$ calculated for a particular QC Rule, the expected number of unacceptable results reported $E(N_U)$ can be determined by multiplying $ARL_U$ by the expected number or patient samples in a batch $E(N_B)$, or $E(N_U)=ARL_U \cdot E(N_B)$. Turning to FIG. 37, $E(N_U)$ is calculated for three different patient sample batch sizes $E(N_B)$ by multiplying $ARL_U$ (as shown in FIG. 36) by exemplary patient sample batch sizes $E(N_B)$ of 40, 30, and 20. As seen in FIG. 37, this results in three $E(N_U)$ curves corresponding to the three batch sizes, and having probability peak values of approximately 1.6, 1.2, and 0.8, respectively. Thus, for the selected Mean/Range Rule, with $N_Q=2$, bracketing a patient sample batch size of 40 (corresponding to $E(N_B)=40$) results in, on average, an expected number of unacceptable results reported $E(N_U)$ of 1.6, while bracketing a patient sample batch size of 20 results in, on average, the expected number of unacceptable results reported $E(N_U)$ of 0.8.

As will be apparent to those skilled in the art, a desirable system for a given quality control rule can thus be designed by fixing $E((N_U)$ as a quality specification so that the design parameters of the system become the probability of a false rejection and the number of patients tested per quality control specimen. For example, $E((N_U)$ can be fixed at a value approaching, but less than, 1 (e.g., 0.9999) so that, on average, no unacceptable results are reported. From that fixed $E((N_U)$, a value for $E(N_B)$ can be calculated from the equation $E(N_U)=ARL_U \cdot E(N_B)$, as $E(N_B)=E(N_U)/ARL_U$. With the desired expected number of unacceptable results reported $E(N_U)$ set to approximately 1 (i.e., 0.99999), then $E(N_B) \approx 1/ARL_U$. Thus, for any given QC Rule, $ARL_U$ for that rule can be calculated as described above by multiplying $P_E \cdot (1-P_{ed}) \cdot (1/P_{ed} - \frac{1}{2})$, and $E(N_B)$ for that rule can be calculated using $E(N_B)=E(N_U)/.[P_E \cdot (1-P_{ed}) \cdot (1/P_{ed} - \frac{1}{2})]$.

Figure 38:
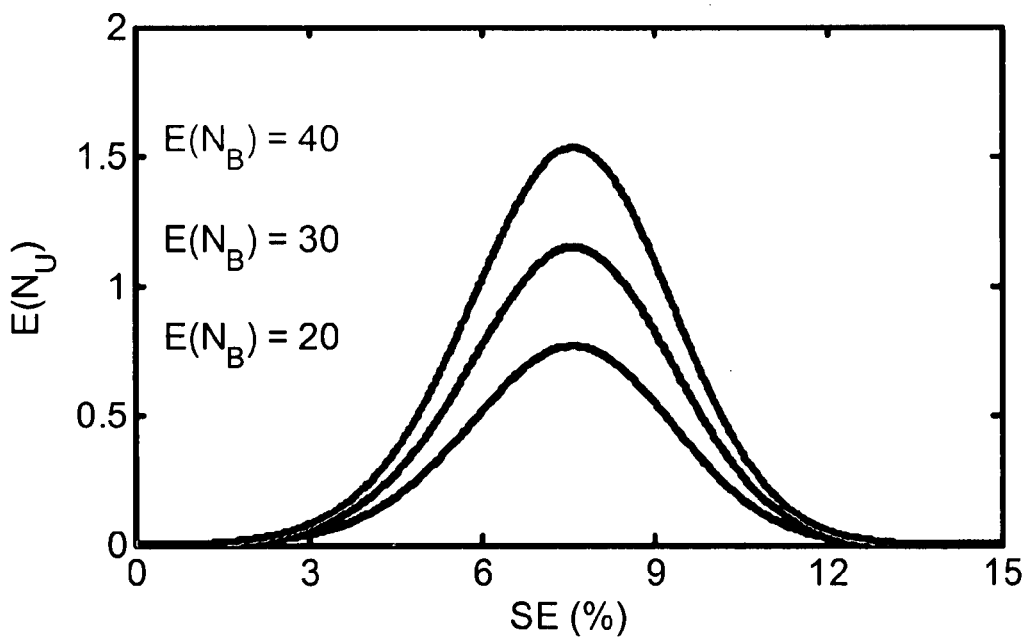

As illustrated in FIG. 38 for a $Z_{1.94}/R_{4S}$ Rule, with $N_Q=2$, an $E((N_U)$ of approximately 1 is desired. Based on the $P_E$ and $P_{ed}$ values for that rule, an optimum batch size of 67 is calculated to provide that desired $E((N_U)$. Thus, bracketing patient sample data at a frequency of 67 (i.e., running a control sample between every 67 patient data samples) would ensure that, on average, no unacceptable results are reported while at the same time minimizing the number of control samples required to achieve that result.

Figure 39:
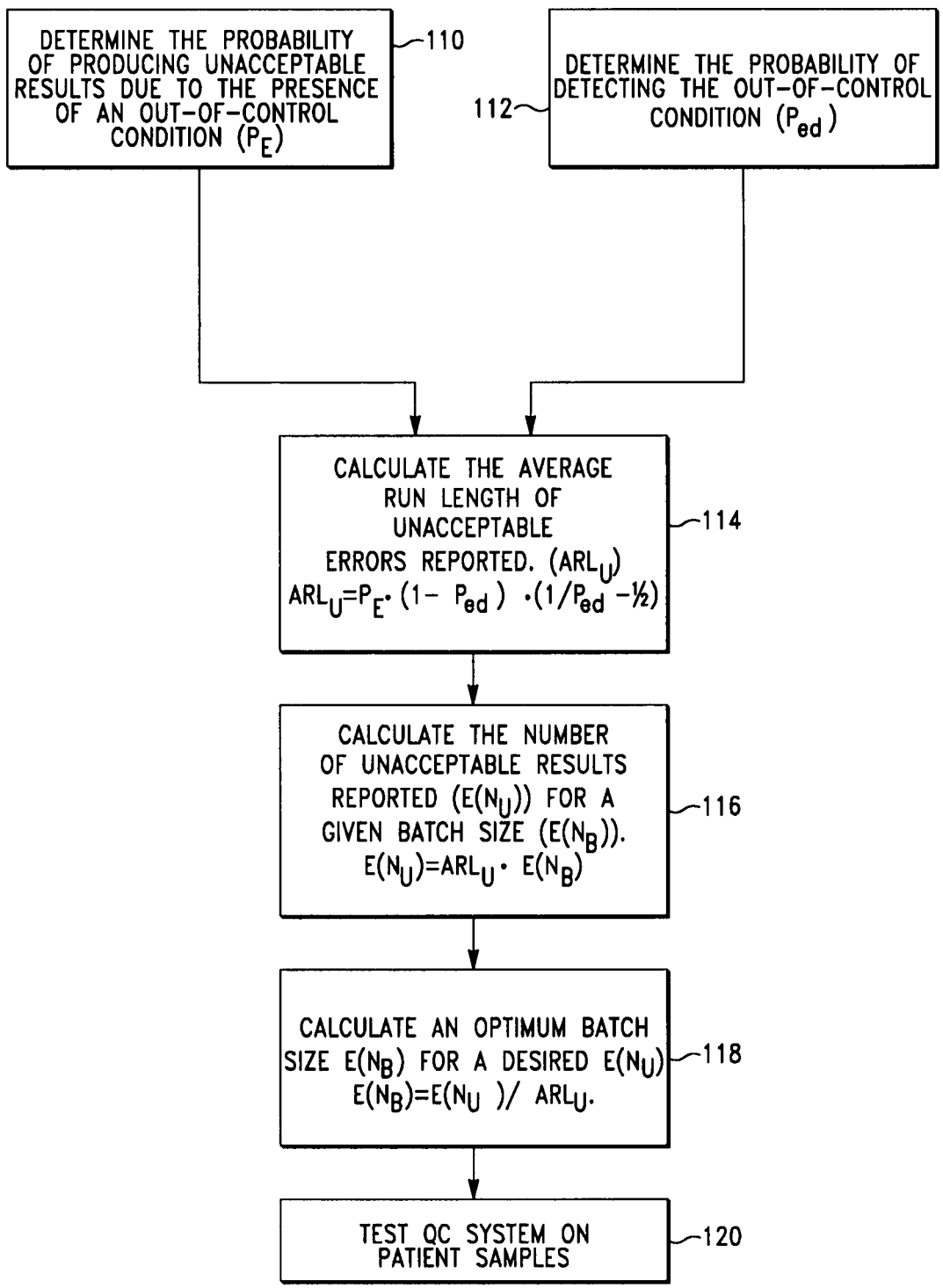
FIG. 39 is a flow diagram of an exemplary method of calculating an optimum batch size for a desired expected number of unacceptable results reported $E(N_U)$ in accordance with an exemplary method of the present invention.

Looking now to FIG. 39, a method of determining an optimum frequency of bracketing patient sample data for a given QC Rule is depicted. At block 110, the probability of producing unacceptable results due to the presence of an out-of-control condition ($P_E$) for that rule is determined. At block 112, the probability of detecting the out-of-control condition ($P_{ed}$) for that rule is determined. At block 114, the average run length of an unacceptable result reported ($ARL_U$) is calculated by $ARL_U=P_E \cdot (1-P_{ed}) \cdot (1/P_{ed} - \frac{1}{2})$.

At block 116, the number of unacceptable results reported ($E(N_U)$) for a given batch size is calculated from $E(N_U)=ARL_U \cdot E(N_B)$. At block 118 an optimum batch size for a given control rule is back-calculated using $E(N_B)=E(N_U)/ARL_U$. At block 120, a QC system is tested on patient samples at a frequency corresponding to the calculated batch size.

A computerized system as described previously with respect to other embodiments of the present invention may be used to implement and test the frequency optimization method just described in a manner similar to that set forth previously. As will be apparent to those skilled in the art, the computerized method may implement and test numerous know QC Rules, or may be used to validate and test new rules. These and other uses and variations on the method described will be apparent to those skilled in the art, and are within the scope of the present invention.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

APPENDIX A

1. Feature: RiliBAK requirements are included in one embodiment of the model.
2. Feature: The application allows for federal and international prescriptions of frequency and type of process control.
3. Feature: The application provides for the highest level of security and encryption for a hospital and laboratory environment to ensure confidentiality of patient data.
4. Feature: The application is able to "de-identify" patient data as required by the laboratory or any lawful regulation. When presented with a test result, the application shall remove any of the following identifiers at the direction of the originator of the data.
   name
   address
   city of residence
   state
   zip or postal code
   country of residence
   age (date of birth)
   gender
   diagnosis Note: The degree or level of de-identification is preferably configurable.
Note: The application preferably has access to the hospital information system (HIS).
5. Feature: The application preferably incorporates relevant requirements of the following NCCLS and EC standards.
   Auto2-P Laboratory Automation: Bar Codes for Specimen Container Identification; NCCLS Proposed Standard 1998
   Auto3-P Laboratory Automation: Communications with Automated Clinical Laboratory Systems, Instruments, Devices, and Information Systems; NCCLS Proposed Standard 1998
   Auto4-P Laboratory Automation: Systems Operational Requirements, Characteristics, and Information Elements; NCCLS Proposed Standard 1999
   Auto5-P Laboratory Automation: Electromechanical Interfaces; NCCLS Proposed Standard 1999
   ENV 1068:1993 (CEN/TC 251) Medical informatics—Healthcare Information Interchange—Registration of Coding Schemes
   ENV 1613:1995 (CEN/TC 251) Medical informatics—Messages for Exchange of Laboratory Information
   ENV 1614:1995 (CEN/TC 251) Healthcare informatics—Structure for Nomenclature, Classification, and Coding of Properties in Clinical Laboratory Sciences
   ENV 12017:1997 (CEN/TC 251) Medical informatics—Medical Informatics Vocabulary
   ENV 12264:1997 (CEN/TC 251) Medical informatics—Categorical Structures of Systems of Concepts—Model for Representation of Semantics
   ENV 12381:1996 (CEN/TC 251) Healthcare informatics—Time Standards for Healthcare Specific Problems
   ENV 12388:1996 (CEN/TC 251) Medical informatics—Algorithm of Digital Signature Services in Healthcare
   ENV 12443:1999 (CEN/TC 251) Medical informatics—Healthcare Information Framework (HIF)
   ENV 12537-1:1997 (CEN/TC 251) Medical informatics—Registration of information objects used for electronic data interchange (EDI) in healthcare—Part 1
   ENV 12537-2:1997 (CEN/TC 251) Medical informatics—Registration of information objects used for electronic data interchange (EDI) in healthcare—Part 2
   ENV 12612:1997 (CEN/TC 251) Medical informatics—Messages for the Exchange of Healthcare Administrative Information
   ENV 12924:1997 (CEN/TC 251) Medical informatics—Security Categorization and Protection for Healthcare Information Systems
   ENV 12967:1998 (CEN/TC 251) Medical informatics—Healthcare Information System Architecture (HISA)—Part 1: Healthcare Middleware Layer
   prENV 12251 (CEN/TC 251) Secure User Identification for Healthcare—Management and Security of Authentication by Passwords.
   prENV 13608-1 (CEN/TC 251) Health informatics—Security for Healthcare Communication—Part 1—Concepts and Terminology
   prENV 13728 (CEN/TC 251) Health informatics—Instrument Interfaces to Laboratory Information Systems
   prENV 13729 (CEN/TC 251) Health informatics—Secure User Identification—Strong Authentication Using Microprocessor Cards
   Requirements of the College of American Pathologists and the Joint Commission on Accreditation of Healthcare Organizations A. General Features
6. Feature: On-demand access is provided to multiple activities at the user interface. The application is designed for ease of use, and navigation is as intuitive.
7. Feature: The application provides multiple input interfaces which may include manual, barcode, wand, touch screen or output from an instrument. Input may also include date, time and operator initials. This information may be provided in a scroll table and stored, e.g., kept for two years or more.
   7a. For each instrument and kit, the application may create monthly and quarterly reports of calibration frequency (number/period of time), frequency of error flags (number/period of time) for each calibrator lot number and reagent lot number singly and in combination and maintained as a record for two years or as required by the user. Users may be able to print these reports on demand. This information may be made available for troubleshooting and to predict the need for calibration.
   7b. In one embodiment, the above information is sent or communicated to the central database. The central application may combine this information with that of other participating laboratories. Interlaboratory comparisons may be provided on request. Manufacturers may also use this information to meet certain FDA requirements.
8. Feature: The application may monitor on-going space temperature and humidity. Data may be maintained as a record according to user requirements. Graphs may be produced on demand and for specific time frames. The data may be maintained as a record for two years or according to user requirements. Alarm thresholds may be user defined. When thresholds are exceeded, the application preferably causes an audible alarm to be heard, provides a dialog box notification, and documents the violation in a log. The log may include a table that summarizes the temperature and humidity integrity daily. Any violation is recorded. The table may also allow for documentation of corrective action. This information may be correlated to any actionable error identified by the system.
9. Feature: The application may monitor on-going freezer, refrigerator, incubator, and water bath temperatures. The software preferably captures instrument incubator temperatures at regular intervals when such information is made available by the instrument. Data may be maintained as a record according to user requirements. Graphs may be produced on demand and for specific time frames. The data may be maintained as a record for two years except for blood bank freezers and refrigerators. This data may be kept as a record for five years or according to user requirements. Thresholds may be user-defined. When thresholds are exceeded the application preferably causes an audible alarm to be heard, provides a dialog box notification, and documents the violation in a log. The log may include a table that summarizes the temperature and humidity integrity daily. Any violation shall also be recorded. The table may also allow for documentation of corrective action. This information may be correlated to any actionable error flag identified by the system.

10. Feature: The application may provide for user documentation of daily, quarterly, monthly, semi-annual and annual maintenance for the life of the instrument. Input may be manual, by barcode, wand or by touch screen. Input may also include date, time and operator initials. These events may be correlated to any actionable error.

10a. When possible the application preferably distinguishes when weekly, monthly, quarterly, semi-annual, and annual maintenance is overdue and give notice to the test operator.

11. Feature: The application maintains summary files of all patient test results processed by gender and age for a period of two years.

11a. Age is calculated from birth date where required.
        11a.1 Birth date should not be kept for privacy reasons.
    11b. The application is able to differentiate between lab-defined normal and abnormal patient test results.
        11b.1 The application should include (incorporate) the NCCLS model for calculating reference ranges.
        11b.2 Differentiation is based on published normal ranges or regional reference ranges.
    11c. The application is able to retrieve age and gender from the HIS. The application is able to link age and gender to specific patient test results.

12. Feature: The application accepts and processes QC and patient data and hands off patient data approved for release to the LIS.

13. Feature: The application is able to accept data from all automated instruments. The application includes bi-directional communication with the LIS and HIS systems.

14. Feature: The application accommodates semi-quantitative test results.

15. Feature: The application accommodates titers.

16. Feature: The application accommodates absorbency readouts.

17. Feature: The application is able to accept probability values.

18. Feature: All QC data and patient data collected, and calculated parameters are preferably communicated back to the central application database at regular intervals.

18a. Laboratory quality control data points and daily baseline population summaries (mean, median, cv) for each test are automatically sent to the central database at least once per day. QC data is sent more frequently for InstantQC.
    18b. The local application maintains individual QC data points and patient test results for each participating laboratory for a period of two years. As data points reach two years and one day they can be purged from the system.
    18c. If the user wishes not to share patient data, then the application is able to automatically submit all other data while retaining restricted data.

19. Feature: All control data is treated in the same manner.

20. Feature: The application allows for on demand access to the internet.

21. Feature: The application maintains various data records specified throughout this document. The application should be able to communicate to the hardware device(s) selected for archival. These may include:
    random array of independent discs (RAID)
    automated tape library
    optical jukebox
    CDRW 22. Feature: The application should be designed to operate on a local server and a virtual server. The local server is defined as a server located in the laboratory. The virtual server is defined as a server located at a remote location; i.e. an application service provider model. With reference to FIG. 2, for example, client 10 in environment 11 (e.g., laboratory) is a local server, and server 60 is a virtual server in one embodiment.

B. Pre-Configuration

The laboratory (or hospital or other environment) provides certain pieces of information before the application is installed and configured. In one embodiment, data processing is typically performed by the central application (i.e., module 40), or by peripheral software and hardware modules in conjunction with the central application. Thus, where the central application is referred to herein as performing a function, peripheral software and/or hardware modules may also perform the function and report results to the central application. The information provided by the laboratory is used to:

23. Feature: Establish routine QC 1ks limits for each test
    23a. Accomplished in collaboration with laboratory management
    23b. The limit is based on total error (biological variation) and/or medical relevance
        23b.1 Lab provides three months (minimum 90 data points) of QC data for each test and level of control.
            23b.1.1 The central application calculates a mean and standard deviation using this data.
            23b.1.2 The central application estimates bias using peer, method, and all instrument group data.
            23b.1.3 The central application calculates current total error and makes a comparison to the total error budget as defined by biological variation as characterized by Dr. Carmen Ricos, Dr Per Petersen, and Dr. Callum Fraser. (See, e.g., Ricos C., Alvarez V., Cava F., Garcia-Lario J. V., Hernandez A. Jimenez C. V., Minchinela J., Perich C., Simon M.: Current databases on biological variation: pros, cons and progress; Scand J Cliln Lab Invest, Vol. 59, No. 7, November 1999, pp 491-500; Fraser C. G., General strategies to set quality specifications for reliability performance characteristics; Scand J Cliln Lab Invest, Vol. 59, No. 7, November 1999, pp 487-490).
        23b.2 The central application recommends 1ks limits.
    23c. Lab provides medical relevance limits where these are preferred to set the 1ks limit.
        23c.1 The central application maintains a record of medical relevance limits as defined by each laboratory for each test to create a master template and reference library.
        23c.2 The medical relevance limit defines the upper and lower limits of acceptability.

24. Feature: Establish baseline population and time-interval baselines for each test using patient data.
    24a. Lab provides one year of time and date stamped patient data for each test. If the laboratory is unable to provide the minimum data required, generic templates or simulations may be substituted until such time as sufficient data is collected from the laboratory.

24a.1 The central application calculates baseline population truncation limits for each test through simulation.

24b. The central application establishes and implements parameters for the baseline population
- 24b.1 The central application calculates a mean, median, standard deviation, low truncation limit and high truncation limit.
- 24b.2 The application tracks the number of patient test results excluded daily from the population baseline by truncation (frequency of exclusion: low and high limit).
  - 24b.2.1 Excluded results are not discarded but retained for future use when the baseline population is updated annually.

24c. The central application updates the baseline population for each test annually.
- 24c.1 All patient results from the previous year (included and excluded) are used in the update
  - 24c.1.1 The application provides an annual comparison of the current and preceding baseline population parameters.

24d. The central application creates time interval baselines from the baseline population for each test using a model to be developed for this purpose.
- 24d.1 Time intervals are specific for hour of the day and day of the week.

Note: A means to depict the time frame may be w/d/hh. Hour should be expressed as a 24-hour clock.
Example: 3:00 PM on Thursday of week three could be expressed as 3.5.1500.

- 24d.2 The central application recommends to the laboratory what time-intervals should be used to gain the highest degree of effectiveness with the EWMA (or CUSUM) and EWMA (or CUSUM) for variance models.
- 24d.3 A mean, median and standard deviation are calculated for the patient data population contained within each time interval for each test.
- 24d.4 The central application creates and maintain libraries of patient baseline populations, truncation limits and time interval parameters for each test. These are determined through simulation using data collected from all participating laboratories. These templates are installed at laboratories that are unable to provide the required time-stamped patient data.

25. Feature: Establish limits for the EWMA (or CUSUM) models for both QC data and patient data.

25a. The central application recommends limits and parameters for EWMA (or CUSUM) based, in certain aspects, on original work published by Crowder in 1989 and Neubaurer in 1997 (EWMA) and Lucas and Crosier in 1982 (CUSUM). (See, e.g., Crowder Stephen V., Design of Exponentially Weighted Moving Average Schemes, Journal of Quality Technology, July 1989, Vol 21. No. 3, pp 155-162; Neubauer A. S., The EWMA control chart: properties and comparison with other quality-control procedures by computer simulation, Clinical Chemistry 43:4, 1997 pp. 594-601; Lucas James M., Crosier Ronald B., Fast Initial Response for CUSUM Quality Control Schemes: Give your CUSUM a Head Start, Technometrics, February 2000, Vol. 42., No. 1, pp. 102-107).
- 25a.1 The EWMA and CUSUM models are modified for patient data to use z scores calculated using the time interval baseline statistics.
- 25a.2 EWMA (or CUSUM) limits are reviewed periodically, e.g., quarterly, in terms of the frequency of false error detection.

C. Configuration

The following specifications describe various examples and embodiments useful for identification of the laboratory, characterization of instruments, tests and methods and establishing technical parameters.

Lab Number (Required)

26. Feature: The Lab Number is the primary number for identifying the laboratory and tracking performance.
- 26a. The Lab Number is alpha numeric.
- 26b. The Lab Number originates from the central system at QSD but can be requested and issued by subsidiaries.
- 26c. The character of the Lab Number is designed so that lab location can be easily identified by visual means. The Lab Number includes abbreviation of state or country|postal code |unique three digit number.

| e.g. | abbreviation of state or country | postal code | unique three digit number |
|---|---|---|---|
| | TX | 75028 | 123 |
| | CAN | P70C12 | 123 |

Lab Number = TX75028123
Lab Number = CANP70C12123

27. Feature: The application provides entry for the following information to further configure the lab number.
- 27a. Laboratory/Institution/Organization name. (required)
- 27b. Department (required)
  - 27b.1. A drop down list provides a selection of departments (areas where testing occurs) in alpha order.
    - 27b.1.1 Departments or areas to be listed include:

| | | | |
|---|---|---|---|
| 01 Ambulatory Care | 02 Blood bank | 03 Cardiac unit | 04 Coagulation |
| 05 Dialysis lab | 06 Electrophoresis | 07 Emergency room | 08 Endocrinology |
| 09 General chemistry/chemistry | 10 Genetics lab | 11 Hematology | 12 Immunoassay |
| 13 Immunology | 14 Infectious Disease | 15 Intensive care | 16 Microbiology |
| 17 Molecular | 18 Oncology | 19 Outpatient Facility | 20 Pharmacy (Therapeutic Drugs) |
| 21 Point of care | 22 RIA | 23 Serology | 24 Special chemistry |
| 25 Stat Lab | 26 Surgical Suite | 27 Toxicology | 28 Transfusion Service |
| 29 Urinalysis | 30 Virology | | |

- 27b.1.2 The department number is a two-digit number and is combined with the Lab Number to create a unique sub-grouping of the Lab Number. All subsequent information (e.g. instrument, test, method) is linked to this sub-group number; i.e. this sub-group creates a unique audit trail. For example, the sub-group number for the coagulation department (04) of Lab Number TX75028123 would be TX7502812304.
- 27b.1.3 If a department exists but is not listed therefore has no code number, a user (e.g., with administrative access) can modify the application to include the new listing and code number.
- 27b.1.4 Modifications to the Department Code list (name and code number) as a general release is issued at regular intervals.
- 27c. Contact Person (required)
  - 27c.1 This field is provided to enter the contact person's name for the department selected.
- 27d. Contact Person Phone Number (required)
  - 27d.1 This field is used to enter the contact person's phone number. Separate fields are provided for country code, city or area code, phone number and phone extension.
- 27e. Contact Person FAX number (optional)
  - 27e.1 This field is used to enter the contact person's FAX number. Separate fields is provided for country code, city or area code, and FAX number
- 27f. Contact Person's Email (optional)
  - 27f.1 This field is used to enter the contact person's Email address.
- 27g. Contact Person's Mailing Address (required)
  - 27g.1 This field is used to identify the contact person's mailing address. Separate fields is provided for street address (required), mail stop (optional) building number (optional) suite (optional) city (required), state or province (required), country (required-selection is made from a drop down list).
  - 27g.2 Address formats are country specific.
  - 27g.3 The postal code entered is used as a part of the Lab Number configuration.
- 27h. When all information is complete, the application creates a lab number sub-group.
- 27i. All user input is converted to upper case letters.
- 27j. This cycle is repeated until all departments within a facility using the system are accounted for.
- 27k. The application allows the user to duplicate the configuration for one lab or lot number to another lab or lot number.

2. Lot Numbers

Lot number is used to identify the control product, the calibrator, and reagent.

28. Feature: Control Products
  - 28a. The application allows the user to select the control product by manufacturer, lot number and expiration date.
  - 28b. The application allows user to select control product categories. Categories include, for example:
    Bio-Rad Branded Products
    Bio-Rad Custom Products
    Bio-Rad Co-labeled Products
    Non-Bio-Rad Products
  - 28c. The application provides a list of control product names depending on the category selected.
  - 28d. When a particular Bio-Rad product name is selected, a list of lot numbers specific to the product is automatically provided for selection.
  - 28e. The Custom Products group provides Custom and co-labeled product names, lot numbers and expiration dates.
  - 28f. Non-Bio-Rad products names may include but are not limited to:
    Abbott
    Beckman
    Dade
    MAS
    Ortho
    Roche
    Sigma
  - 28g. If a non-Bio-Rad product is selected, the user may select the name from a drop down list and then enter the lot number, expiration date, and number of levels from drop down lists or other means.
    - 28g.1 The application may capture from the instrument or require the user to enter a lot number and expiration date.
  - 28h. If the non-Bio-Rad product is a single level, the application allows the user to indicate whether this product is linked to any other lot number (s) of the same manufacture.
    - 28h.1. This is required for reporting mechanisms and use of graphics in the system.
  - 28i. The application is programmed with expiration dates for all Bio-Rad products on the system.
    - 28i.1 When a lot number expires, the application shall not accept any additional QC data generated for that lot. This can affect patient-based and QC-based models because they depend on QC data.
      - 28i.1.a The application provides a mechanism to re-activate whenever there is a circumstance to stop processing data.
    - 28i.2 Prior to expiration, e.g., three months, the system begins to notify the user every 48 hours that a lot is nearing expiration. The application shall also provide a "Do not show me this message again" button each time the warning is issued.
      - 28i.2.1 The application shall automatically notify the appropriate Bio-Rad sales order department that the product requires renewal.
  - 28j. The application accommodates parallel testing of control materials.
    - 28j.1 The application allows the user to copy the configuration of one lot of control product to another lot of control product regardless of who manufactures the product.
  - 28k. The application provides a listing of all control products currently in use showing linkages to instruments and tests.

29. Feature: Calibrators
  - 29a. The application allows the user to enter and track calibrator lot number.
  - 29b. The application allows the user to identify the calibration product by manufacturer, lot number and expiration date.
    - 29b.1 The drop down list of manufacturers for calibrators is the same list of manufacturers for instruments. Additional names on the list may include but are not limited to
      Casco
      Sigma
  - 29c. The application time and date stamps when calibration occurs.

Figure 40:
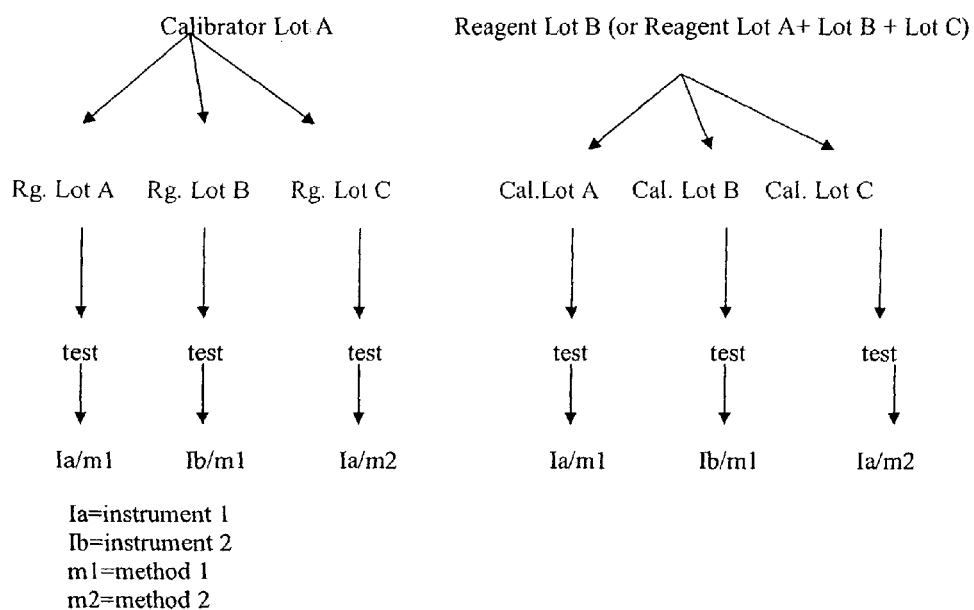
FIG. 40 shows an exemplary instrument/test and calibrator-reagent lot combination in accordance with one embodiment.

Note: Usually when a calibration occurs a multiple number of tests are calibrated as a part of the same event. Other times a single test may be calibrated. The application accommodates either situation.
  - 29c.1 The application marks all graphs and charts to visually indicate when calibration occurs. Placing the cursor over the mark shall reveal the date and time of calibration and the lot number and manufacturer of the calibrator.
    29c.2 Change of calibrator lot does not create a new routine QC database.
  29d. The application also allows the user to identify if the calibration is a scheduled or unscheduled calibration. A scheduled calibration is typically a calibration event prescribed by the manufacturer, instrument manual and/or laboratory policy. An unscheduled calibration is a calibration that occurs for any other reason.
    29d.1 The application provides for input to document the reason for unscheduled calibrations.
  29e. The application calculates the number of days and the number of patient test results processed between calibration events.
    29e.1 The application calculates the mean and median for the number of days and patient test results between calibration events and across calibrator lots.
  29f. When possible the application captures the most recent calibration curve.
    29f.1 Calibration curves are maintained by the application.
    29f.2 The application applies an appropriate statistical model to all calibration data. Tolerance limits are calculated.
    29f.3 The application provides a mechanism to compare the calibrations of two or more instruments.
    29f.4 The application warns the operator when any new curve falls outside calculated tolerance limits.
    29f.5 An EWMA model is implemented for each calibrator level once sufficient data is collected to operate the model.
    29f.6 Tolerance limits are restrictive. The test operator is notified when a calibrator EWMA signal occurs.
  29g. The application tracks, calculates, and maintains as a record the number of actionable errors for each calibrator lot.
    29g.1 The application tracks and calculates the mean and median number of actionable errors across calibrator lots.
  29.h The application tracks, calculates and maintains as a record the number of warnings for each calibrator lot.
    29h.1 The application tracks and calculates the mean and median number of warnings across calibrator lots.
  29i. Data for calibrator and reagent lots shall also be linked and traceable to specific tests, instruments and methods. Example: The application is able to provide on demand the mean time between error detection for Calibrator Lot A/Regent Lot B, as illustrated in FIG. 40.
    29i.1 The application is able to calculate and provide test specific QC and patient-based mean, median, standard deviation, bias and z-score according to calibrator lot, reagent lot, across calibrator lot, across reagent lots, and within and across calibrator-reagent lot combinations.
    29i.2 The application is able to calculate and provide error rates, calibration rates, QC and patient-based mean, median, standard deviation, bias and z-score according to calibrator lot, reagent lot, across calibrator lot, across reagent lots, and within and across calibrator-reagent lot combinations for specific instruments, between instruments, between departments and for tests and instrument/test combinations.

30. Feature: Reagents
In one embodiment, the application identifies reagents in use by lot and tracks key performance characteristics by reagent lot or admixture of reagent lots. This information may be combined with reagent information from other participating laboratories to create a worldwide database available to participating laboratories and manufacturers.
  30a. The application captures from the instrument or provides a mechanism to enter and track reagent lot numbers.
    30a.1. The application allows the user to document reagent lot change. Input may be manual, by barcode, by touch screen or output from the instrument. Input shall also include date, time and operator initials. This information is provided in a table and maintained for a period designated by the user.
    30a.2 The application allows the user to identify the reagent by manufacturer, lot number and expiration date.
      30.a.2.1 A list of reagents is the same as that provided in the UNITY application.
  30b. The application time and date stamps when a new lot number of reagent is put into use.
    30b.1 The application allows the user to input when the reagent(s) was received by the laboratory, when the reagent(s) was put into use, when the reagent(s) expires, the lot of the reagent(s) and some identifier for the person putting the reagent into use.
    30b.2 The application allows the user to indicate when more than one reagent is used to assay the analyte and whether these reagents are mixed prior to putting the reagent on the platform or introduced at the time of assay.
      30.b.2.1 If two or more reagents are mixed to create a new single reagent, the application allows the user to identify by lot which reagents were mixed and to enter a new expiration date.
  30c. The application also directs the user to classify the change as expected or unexpected. For example, an expected reagent change occurs when the reagent expires or is depleted. An unexpected change occurs for any other reason.
    30c.1 The application provides input for documenting the reason for unexpected reagent change.
  30d. The application graphically marks all graphs and charts to visually indicate reagent lot changes. Placing the cursor over the mark shall reveal the date, time put into use and the lot number.
  30e. Change of reagent lot does not create a new routine QC database.
  30f. The application calculates the number of days and the number of patient test results processed for each reagent lot.
  30g. The application calculates the mean and median number of days and patient test results across reagent lots.
  30h. The application tracks and calculates the number of actionable errors for each reagent lot.
  30i. The application tracks and calculates the mean and median number of actionable errors across reagent lots.
  30j. The application tracks and calculates the number of warnings for each reagent lot.
  30k. The application tracks and calculates the mean and median number of warnings across reagent lots.
  30l. The application calculates the number of days and the number of patient test results processed between calibration events for each reagent lot.

30m. The application calculates the mean and median number of days and patient test results across calibrator lots for each reagent lot.

30n. The application tracks and calculates the number of actionable errors for each calibrator-reagent lot combination 30o. The application tracks and calculates the mean and median number of actionable errors across calibrator-reagent lot combinations.

30p. The application tracks and calculates the number of warnings for each calibrator-reagent lot combination.

30q. The application tracks and calculates the mean and median number of warnings across calibrator-reagent lot combinations.

30r. Data for calibrator and reagent lots is linked and traceable to specific tests, instruments and methods.

Example: The application is able to provide on demand the mean time between error detection for Calibrator Lot A/Regent Lot B, as illustrated in FIG. 40.

30r.1 The application is able to calculate and provide test specific QC and patient-based mean, median, standard deviation, bias and z-score according to calibrator lot, reagent lot, across calibrator lot, across reagent lots, and within and across calibrator-reagent lot combinations.

30r.2 The application is able to calculate and provide error rates, calibration rates, QC and patient-based mean, median, standard deviation, bias and z-score according to calibrator lot, reagent lot, across calibrator lot, across reagent lots, and within and across calibrator-reagent lot combinations for specific instruments, between instruments, between departments and for tests and instrument/test combinations.

30r.2.1 Statistical correlation between QC data or patient data to error rates and calibration rates is to be developed.

31. Feature: Instruments

31a. The application allows the user to select the instrument.

31b. The lab number allows for separate identification of two instruments of the same manufacture and model. (e.g. 01, 02, etc.)

31c. The application allows the user to duplicate the configuration for one lab or lot number to another lab or lot number.

32. Feature: Tests

32a. Each test is configured for instrument, method, reagent, temperature and units.

33. Feature: Rules

33a. The application preferably uses only a $1k_s$ rule. This rule is based on total allowable error ($TE_a$) using biological variation studies, known precision as determined by repetitive QC testing, and clinical or medical relevance. This rule is set to detect actionable error only. When this rule is violated, actionable error exists.

33a.1 The $1k_s$ rule is test specific and set in collaboration with laboratory management. The application allows for test-specific error detection limits.

Note The application preferably does not use Westgard rules.

34. Feature: Temperature

34a. Each test (analyte) is configured for assay temperature.

35. Feature: Units

35a. Each test (analyte) is configured for units of measure.

D. Equilibration

Equilibration includes a twelve week period in which both QC data and patient data are collected and analyzed by the Biometric model. While equilibration officially ends after twelve weeks, it may be six months to a year before the model is fully optimized for some tests. The purpose of the equilibration period is to collect sufficient data to recommend QC testing frequencies (routine QC) and to validate and adjust when necessary the operation of EWMA (or CUSUM) models in the laboratory setting.

36. Feature: The $1k_s$ rule, EWMA (or CUSUM) for routine QC, EWMA (or CUSUM) for patient data, and confirmation testing is in effect during the equilibration period.

36a. Routine QC and patient data QC are co-dependent in the Biometric model.

36b. If the $1k_s$ rule is violated for routine QC, actionable error has occurred. The operator shall cease processing patient test results, troubleshoot, take correction action and perform confirmation testing.

36c. If the routine QC EWMA model signals an error, this error is considered actionable. Maintenance, calibration or troubleshooting follow. Confirmation testing is required.

36d. If the patient data EWMA(or CUSUM) model (Pro-Tech E and ProTech C) signals an error, this error is deemed actionable. Otherwise the signal may be attributed to a possible change or shift in the patient population.

37. Feature: The application tracks the magnitude and frequency of actionable errors and false error detection for the $1k_s$ rule for each test. While a 1ks rule violation is deemed to be cause for action, if troubleshooting is unable to identify a root cause, then the error should be considered a false error detection and the application provides a means for the user to modify the characterization of the error. The application recommends adjustment when necessary.

38. Feature: The application tracks the frequency of warnings and/or actionable errors issued by the EWMA (or CUSUM) models for each test. The application recommends adjustments when necessary.

39. Feature: QC materials is tested at prescribed intervals during the equilibration period.

39a. If an analyte is assayed at random throughout the day, each level of QC material (three levels for tri-level controls and two levels for bi-level controls) is assayed once every eight hours.

39b. If an analyte is tested in batch only once in a day, each level of QC material (three levels for tri-level controls and two levels for bi-level controls) is assayed once each day the test is performed.

40. Feature: QC results from confirmation testing are preferably not included in the record of QC results for Routine QC.

41. Feature: At the end of the equilibration period, the frequency and magnitude of actionable errors generated by the $1k_s$ rule and the EWMA (or CUSUM) models in combination with the total error and imprecision of the test are used in a free-standing risk model that outputs schedules of routine QC testing for each test. Each frequency is associated with a predictive risk of reporting patient results with unacceptable quantities of error.

E. Operation

Historically, theoretical work on QC systems for clinical laboratory application has focused primarily on monitoring the analytical process by examining data obtained from quality control materials. In no instance has there been an application that attempts to establish a relationship between control data patterns and patient data patterns. The Biometric model uses statistical models for quality control materials as well as for patient data. Each system operates simultaneously but independently of the other.

While the model utilizes both patient and QC systems simultaneously, these models are presented separately in this specification for clarity.

1. Control-Based Monitoring

Testing of control materials yields data used to determine whether the analytical process is in control. The decision when to test control materials and which levels of control to test has always been arbitrary because the laboratory has never been given any guidance. Process control models such as Westgard make no recommendation about when to test control materials. Governments require testing of control materials at regular intervals but do not direct or guide the user about the timing of testing. Some laboratories test QC once per day at the beginning of the day and other labs will test one level of control at the beginning of a batch and another level of control at the end of the batch. Fundamentally, laboratories use no empirical or scientific basis to determine the frequency or character (i.e., which levels of control are to be tested) of QC testing.

Conversely, the model according to the present invention ("Biometric model") is designed to provide a more rational and intelligent approach to analytical process control. It removes the uncertainty from planning a QC protocol by giving the test operator directions and guidance on when to test QC materials and which levels to test. The Biometric model includes a unique free-standing statistical model that assesses risk which are used to customize the day to day process control scheme. Signals (or lack of signals) from both QC and patient-based systems are used after the equilibration phase to determine the frequency and character of QC testing required for each test.

Control-based monitoring of the analytical process in the Biometric model includes:
- routine QC testing as determined by the risk model
- using a $1k_s$ rule to signal actionable error
- monitoring routine QC by EWMA (or CUSUM)
- event driven QC
  - confirmation testing after troubleshooting and corrective action
  - confirmation testing after a change event a. Monitoring Routine QC by the $1k_s$ Rule Routine QC testing for each test occurs at regular intervals. The laboratory chooses the character and frequency of routine QC testing based on risk assessment. Routine QC is monitored by a $1k_s$ rule, and confirmation testing will be in effect. Troubleshooting, corrective action and confirmation testing occurs when actionable error is identified.

42. Feature: QC materials are tested at regular intervals as determined by the risk model.

43. Feature: A $1k_s$ rule is put into place for each level of control for each test.

43a. Because the limits set for routine QC are based on total error, biological Variation and possibly medical relevance, QC values outside the $1k_s$ limit shall constitute actionable error. Testing and processing of patient samples is halted until troubleshooting, corrective action and confirmation testing have been successfully completed. A $1k_s$ rule violation requires re-testing of patient samples.

43b. All patient test results created after the signal are held. The application uses a statistical model to predict at what point the error likely occurred and only those patient samples subsequent to the location of the error are re-tested.

43b.1 The application requires the user to take some action regarding patient test results involved in an actionable error.

43b.2 The application allows the user to select individual patient test results or a range of patient test results to discard.

44. Feature: At the end of twelve weeks, then again at six months and every six months thereafter (or as required), the system reports:
- The frequency of actionable errors identified by the $1k_s$ rule
- The mean time between actionable errors (MTBF)
- The magnitude of each actionable error in multiples of standard deviation 45. Feature: At six months and annually thereafter (or as required) each routine QC protocol is reassessed for appropriateness and effectiveness based on:
- frequency of actionable error
- frequency of false error detection
- changes in imprecision
- changes in bias 46. Feature: Since frequency of routine QC will typically vary from analyte to analyte, each day the application creates a schedule for routine QC testing by test. The system groups or consolidates QC testing required on a particular day. The test requiring the most frequent QC challenges during the day determines the QC testing interval for the day. If the shortest interval for the day is every 4 hours, for instance, then any test scheduled during a particular four hour interval would be consolidated and tested at the same time. (4 AM, 8 AM, 12 PM, 4 PM, 8 PM, 12 AM)

Note: The schedule is user defined.

47. Feature: The application provides a mechanism to re-activate whenever there is a circumstance to stop processing data.

48. Feature: The application provides a mechanism to compare two or more instruments.

Monitoring Routine QC by EWMA (or CUSUM)

In current laboratory environments, quality control materials are tested and plotted on a Levey-Jennings chart. Statistical process control rules are established to monitor the process. This model is effective for identification of statistical error and characterizing the type of error. It has been demonstrated through simulations that Exponentially Weighted Moving Averages (EWMA) of control data is more useful for monitoring the process and alerting the test operator when shifts or trends in performance occur. While loss of accuracy is certainly important, loss of precision can be of critical importance as well especially for patients that are being monitored over time. Consequently, the model uses EWMA to monitor variance as described by Neubauer. (Neubauer A. S., The EWMA control chart: properties and comparison with other quality-control procedures by computer simulation, Clinical Chemistry 43:4, 1997 pp. 594-601) CUSUM is another statistical technique used to monitor for shifts and trends in data as well variance. While EWMA is the primary model for routine QC, some laboratories may prefer to use CUSUM. The application accommodates both models.

49. Feature: The application allows the user to select either EWMA or CUSUM, but preferably not both.

50. Feature: The EWMA and CUSUM models are implemented (under direction).

51. Feature: An EWMA (or CUSUM) signal for routine QC is considered actionable. Testing/processing of patient samples is halted. The application directs the operator to troubleshoot, take corrective action, perform confirmation testing and re-test appropriate patient samples.

51a. The application tracks and maintains as a record the frequency of EWMA (or CUSUM) warning signals and actionable errors.

52. Feature: An EWMA-S (or CUSUM-S) model is implemented (under direction) and used to monitor variance of QC data.
- 52a. The application applies a variance or variance z-score to an EWMA (or CUSUM) model with defined thresholds.
- 52b. An EWMA-S (or CUSUM-S) signal for variance of QC data is considered actionable. Testing and processing of patient samples is halted. The application shall direct the operator to calibrate, perform maintenance, or troubleshoot as appropriate. Regardless, after one or more of these actions are taken, the operator is required to perform confirmation testing. Re-testing of patient samples shall not be required as a result of an EWMA-S(or CUSUM-S).
  - 52b.1 The application tracks and maintains as a record the frequency of variance signals.

53. Feature: The application provides a report of all actionable errors for each test. This report is subject to electronic signature to document review. The laboratory may modify the time frame of the report.

54. Feature: At six months and annually thereafter, the EWMA (or CUSUM) parameters set for each test are reviewed and adjusted as necessary. Adjustments are made based on statistics prescribed throughout this specification.

55. Feature: The application provides a mechanism to re-activate whenever there is a circumstance to stop processing data.

56. Feature: The application provides a mechanism to compare performance statistics of two or more instruments.

2. Patient Based Monitoring

While the patient data model complements the process control model, it is the patient data model that contributes the most unique value to the overall system. Models for analytical process control currently in use by most laboratories focus on testing of control materials rather than on patient data. The Biometric model is unique because routine QC and patient data QC are co-dependent in one embodiment.

The patient data model evaluates individual patient test results in a time series model alerting the test operator when a potential for error may be present in the test system. The model requires establishment of a time-interval baseline, a mathematical model that evaluates each patient test result as it is produced, and a decision tree for treatment of signals issued by the patient model.

a. The Time-Interval Baseline and Baseline Populations

Any statistical model using patient data for analytical process control should account for the time that testing occurs (hour of the day combined with day of the week or month). It follows that multiple customized time-series baselines are required if a patient-based control system is to be both accurate and sensitive to change. The application accounts for criticality by calculating a truncated mean and standard deviation for each hourly time interval. The time interval mean can be calculated using hourly data or data collected for multiple consecutive hours. Accounting for time-series variability will decrease statistical noise and increase error detection potential. Such customization improves analytical control performance.

There are two critical questions that need to be answered when designing a patient based system. These are:
  what data is to be included in the population
  how is the hourly mean and standard deviation of patient data to be used Baseline populations that contain 100% of the sample are insensitive to change because outlying abnormal (low, high) values often skew the mean and increase the standard deviation. Furthermore, patient populations that are inaccurately derived generate inaccurate comparisons. The peak effectiveness of a baseline patient population is directly related to the character of that population. (See, e.g., Parvin Curtis A., Ye Jay J., Ingels Stephen C, Performance Evaluation and Planning for Patient-Based Quality Control Procedures, Am J Clin Pathol 2000, vol 113, pp. 240-248) In other words, some patient test results are considered to be appropriate for inclusion in the baseline population while other data are not. Appropriateness is determined through pre-defined truncation limits derived by simulation.

Many investigators have used truncation techniques on data sets derived from testing of control materials. Because control data distribution is assumed to be Gaussian, truncation is often symmetrical in that investigators will truncate equal portions at each of the two distribution tails. Those few investigators who have also worked on patient data sets often apply the same rules of truncation used on control materials to patient data populations apparently without considering that such populations are not Gaussian and therefore truncation may or may not be equal at both distribution tails. The optimal truncation limits for each test are unique and depend on analytical imprecision, total error requirements, and biological variation.

57. Feature: The application supports remote data management.

58. Feature: Patient test results are preferably processed sequentially and in the order of time produced.

59. Feature: Preferably one year of time-stamped patient data for all tests is obtained. This data is used to determine through simulation the appropriate baseline population truncation limits (e.g., using truncation limits module 45) for each test in the laboratory menu. A mean and standard deviation for the baseline population is maintained locally and at the central database. The percent of data excluded for each tail is kept on record at the site and at the central database. Time- and date stamped patient data is also used to calculate the appropriate means and standard deviations of the patient population for specific time intervals. Time intervals may vary between laboratories and tests. Interlab parameters maintained by the central database for the baseline and time-interval populations may be offered as templates for use during the twelve week equilibration period and perhaps beyond for laboratories that do not have a sufficient database to calculate these elements.
- 59a. One year of time/date-stamped data is preferably used to characterize a baseline for hour and day within a month including weekend and holiday trends.
  - 59a.1 One year of data is needed to account for regular as well as cyclic utilization of the laboratory such as for outpatients, patients diagnosed with specific diseases such as diabetes, end stage renal disease etc, weekends, and holidays.
    - 59a.1.1 The application accounts for public holidays according to country.

60. Feature: The application calculates and maintains as a record the daily, weekly, monthly and annual frequency of rejection for high and low truncation limits for the baseline population and time interval population.

61. Feature: A separate record is kept of individual patient test results segmented by gender and age. Age is calculated from birth date that is subsequently discarded as a privacy measure. This database is undifferentiated meaning that the database is not truncated. These records shall not be used for analytical process control. Rather these records are used for data mining and future information products and services for the lab.

62. Feature: The central application in conjunction with the central database maintains a file/record of the truncated limits for the baseline population, baseline population standard deviation, mean and median. The central application also maintains the time-interval baseline means, medians and standard deviations for each test and for each laboratory using the system.
- 62a. Feature: The application recalculates the baseline population truncation limits for each test, e.g., at six month intervals or on demand, using data collected for the past year. A new baseline population mean, median, and standard deviation is calculated and maintained locally and by the central application.
- 62b. The application performs a test for significance every six months between the truncation limits in use and newly calculated limits.
- 62c. Truncation limits are automatically communicated to the central application so a universal statistical comparator can be developed.
- 62d. Low volume tests, designated by the user, may be evaluated at different intervals.

63. Feature: The application recalculates the time-interval baseline means, medians, and standard deviations for each test, e.g., at six month intervals or on demand, using data collected for the past year.

63a. The application performs a test for significance every six months between the truncation limits in use and newly calculated limits.

63b. Truncation limits are automatically communicated to the central database so a universal statistical comparator can be developed.

64. Feature: The application performs a test for significance, e.g., every six months between the time interval means, medians and standard deviations in use and newly calculated means, medians and standard deviations.
- 64a. Time interval means and standard deviations are automatically communicated to the central database so a universal statistical comparator can be developed.

65. Feature: The application provides:
- a semi-annual report of truncation limits (e.g., past 6 months and current)
- standard deviation, mean, and median (e.g., past 6 months and current) for the baseline population
- time interval means, medians and standard deviations (e.g., past 6 months and current) for each hour of each day of an average month.

This report is used for annual system performance review or troubleshooting.

b. EWMA (or CUSUM) as the Patient-Based Model

66. Feature: When a patient test result is created it is made available to the application. The result is first screened by the baseline population truncation limits. If the result is within limits, it is then passed to the time interval screen. If the result is within the limits defined for the appropriate time interval, a z score is calculated based on the time interval parameters of mean and standard deviation.
- 66a. The application retains a record of all patient data points by test configuration that are found to be reportable by the application.
- 66b. If the result does not pass the baseline screen, the result is passed to an exclusion table. The frequency of exclusion is calculated daily with each new excluded result. If user defined thresholds for exclusion are exceeded, an alert is issued. The operator determines if the root cause is internal or external to the test system. If internal, then patient testing/processing is halted and troubleshooting, corrective action and confirmation testing is required. If the root cause is determined to be external, then patient testing/processing shall continue.
- 66c. If the result does not pass the time interval screen, the result is passed to a time interval exclusion table. The frequency of exclusion is calculated daily with each new excluded result. If user defined thresholds for exclusion are exceeded, an alert is issued. The operator determines if the root cause is internal or external to the test system. If internal, then patient testing/processing is halted and troubleshooting, corrective action and confirmation testing is required. If the root cause is determined to be external, then patient testing/processing shall continue.

67. Feature: The calculated z score is passed to an EWMA (or CUSUM) model for evaluation (ProTech-E or ProTech-C). The signed z-score is added to the EWMA (or CUSUM) total.
- 67a. The ProTech-E (or ProTech-C) model is implemented.
- 67b. If the result triggers a signal from the ProTech model, actionable error may be present. QC is tested. If the results of this testing confirm that error is present, then testing and processing of patient samples is halted. The application directs the operator to troubleshoot, take corrective action and perform confirmation testing. Re-testing of patient samples is required as a result of a ProTech-E or ProTech-C signal supported by QC EWMA (or CUSUM).
- 67c. If routine QC does not support the signal issued by the ProTech-E (or ProTech-C) model, testing and processing of patient samples resumes. This type of error is likely due to a change or shift in patient population. This needs to be verified by the operator before testing resumes.

68. Feature: The ProTech-ES (or ProTech-CS) model is implemented (under direction) and used to monitor variance of time interval and baseline populations. Time interval daily mean is the mathematical average of all patient results occurring during a single 24 hour day for the designated time period. Time interval daily variance is the calculated imprecision of all patient results occurring during a single 24 hour day for the designated time period. The grand mean is an average of daily time interval means. The grand variance is the average of daily time interval variances.
- 68a. The application calculates the variance for the daily time interval baseline and baseline populations.
- 68b. The application identifies the grand mean and variance for all daily time interval baseline and baseline population variances.
- 68c. The application calculates a z-score using the daily time interval or baseline population variance and the grand mean and variance for the respective baseline.
- 68d. The application applies the variance z-score to an EWMA model with defined thresholds.
- 68e. A ProTech-ES or ProTech-CS signal for variance data is considered a warning signal. The application shall advise the operator to calibrate, perform maintenance, or troubleshoot as appropriate. Regardless, if one or more of these actions are taken, the operator is required to perform confirmation testing. Re-testing of patient samples shall not be required as a result of this type of signal.
  - 68e.1 The application tracks and maintains a record of the frequency of variance warning signals.

69. Feature: If the test result fails either the baseline population or time-interval screen, the result is not evaluated further. The result is retained as a part of the overall baseline population for the test. A daily, weekly, monthly and annual record of the percent of data points excluded from each tail for each test is kept as a record. The test operator can request a table/report of this information on demand.

70. Feature: When a patient data EWMA (or CUSUM) signal is issued the result that triggered the event and all subsequent test results are rejected/discarded if actionable error is identified. The application uses a statistical model to predict at what point the error likely occurred. All samples subsequent to the time or placement predicted by the model are re-tested. The databases are recalculated where necessary.
    70a. The application is able to identify the patient sample by number, date/time.

71. Feature: The application provides a mechanism to re-activate whenever there is a circumstance to stop processing data.

72. Feature: The application provides a mechanism to compare performance statistics for EWMA (or CUSUM) and ProTech models for two or more instruments.

F. Event Driven QC

73. Feature: The application preferably requires the user to perform confirmation testing whenever a change events occur, including, for example:
    calibration
    change of reagent lot number
    any maintenance other than daily maintenance
    notice from the manufacturer of test component modification or change
    platform application updates/upgrades
    any change that has potential to alter the measurement process of the analytical system 74. Feature: Confirmation testing is used to validate the process remains unchanged after one of the previously listed events occurs.
    74a. QC results from confirmation testing are preferably not included in the routine QC database.
    74b. The application requires confirmation testing. It can not be deferred.

75. Feature: The number and concentrations of QC materials to be tested for confirmation testing is determined by a statistical.

G. Troubleshooting and Error Resolution

Actionable events require evaluation, troubleshooting, confirmation testing and documentation. Actionable events include:
    A 1 $k_s$ rule violation
    An EWMA (or CUSUM) signal for routine QC.
    An EWMA (or CUSUM) signal for patient data supported by routine QC testing.

The following specifications describe various examples and embodiments useful for evaluation, troubleshooting and confirmation testing.

76. Feature: When an actionable error occurs, testing of patient samples is halted. The test operator is directed to evaluate key parameters, troubleshoot, undertake corrective action and then perform confirmation testing.

1. Troubleshooting: General Requirements

77. Feature: The system is able to recognize and characterize recurring trends in both patient data and QC data, then alert the test operator when such trends are identified.

78. Feature: Instrument-specific or kit-specific troubleshooting guidance with keyword search is available online or through internet access.
    78a. The application is able to access and interact with internet-based technical manuals.

79. Feature: When actionable error occurs for a particular test, the application provides the user statistical reports that aids in troubleshooting the error. These reports may include, for example:
    a statistical comparison of the last calibration curve to a comparator calibration curve derived from an appropriate statistical model based on all previous calibrations
    a report of the frequency, and magnitude of actionable and warning errors for the test
    the nearness in time of the last calibration and whether it was expected or unexpected
    the nearness in time of the last reagent and reagent lot change and whether it was expected or unexpected.
    the nearness in time for daily, weekly, monthly, semi-annual, and annual maintenance
    a reflex check of all EWMA (or CUSUM) charts and statistics for each analyte that share common characteristics (wave length, number of reagents, incubator temperature, etc.) with the analyte under question.
    corrective actions taken within a user-defined period of time in code format (see above). When the cursor is placed over the code, a description of the action taken is provided along with the date and test operator initial.
    link CVs/precision, error rates, and calibration frequency to maintenance records and previous troubleshooting.

80. Feature: The application provides the following key parameters on demand:
    a standard Levey-Jennings chart for plotting QC data comparable to UNITY application
    a standard Levey-Jennings chart for plotting QC data with 95% confidence intervals surrounding each data point
    a standard Levey-Jennings chart for plotting QC data reflecting total allowable error
    a normalized Levey-Jennings chart for:
    multiple levels of QC data points for a single test for a user defined time period
    QC data for a single test but for multiple instruments
    a standard Levey-Jennings chart of QC data points scaled according to lab, peer, method and all instrument group over a user defined time period.
    a Youden plot of QC data points scaleable to 7 days, 30 days or six months. The application allows the test operator to choose which pairs of control levels will be displayed on the Youden plot if the control is a tri-level control and values have been obtained for each level.
    the current EWMA (or CUSUM) charts for routine QC and QC variance
    the current EWMA (or CUSUM) charts for patient data and patient data variance 81. Feature: The system tracks and maintains a record of the percent of daily results excluded by the low limit and by the high limit of the baseline population. The percent excluded on the low side is negatively signed. The percent excluded on the high side is positively signed.
    81a. An exclusion score is calculated by adding the percent excluded (low) to the percent excluded (high) for the day only.
    81b. Whenever a data point is excluded, the appropriate file (low/high percent) is updated.
    81c. Scores and percents are zeroed at midnight.
    81d. An ongoing record of the final score for each day is kept by the system locally. These scores can be monitored at random and may be consulted as a part of troubleshooting.

82. Feature: The application provides a 7-day, 30 day or six month report on demand of all actionable errors and warnings for each test. This report is subject to electronic signature to document review. A user may modify the time frame of the report.

83. Feature: The application assesses error flags based on the following interpretative grid.

| | EWMA (or CUSUM) Results | | | |
|---|---|---|---|---|
| Patient Data | Flag | Flag | No Flag | No Flag |
| QC Data | Flag | No Flag | Flag | No Flag |
| Interpretation | Actionable error; Method or system problem or change; | Change in patient population | QC limits may need adjustment. | System Stable |

2. Troubleshooting: Indices a. Calibration Index

The calibration index helps distinguish error flags that are due to faulty or non-optimal calibrations.

84. Feature: The application stores all calibration curves for each test on each platform.
 84a. An appropriate statistical technique is applied to estimate a best fit curve.
 84b. The statistical parameters of this best fit curve is available on demand.

85. Feature: The application maintains a mean, median, and standard deviation of the values for each calibrator level collected over time.
 85a. The application calculates a standard deviation index for each level of calibrator for the current calibration using the calibrator value from the best fit curve and the standard deviation of the values collected for the calibrator over time.
 85b. The application maintains an on-going record of the SDIs for each calibrator level for each calibration event.
 85c. The record is available on demand.

b. Temperature Index

The temperature index can isolate incubator temperatures as the source of error when the assay incubation temperature fluctuates or changes.

86. Feature: Each test monitored by the model is coded for specific temperature (see Configuration).

87. Feature: The application allows the user to choose a temperature and assay platform of interest.
 87a. The application provides a list of all assays on the platform that are tested at the temperature selected.
 87b. The application provides the current QC and patient data EWMA graphs (or CUSUM statistics) for each test selected when an error flag occurs or on demand for the purpose of comparison.
 87c. The application uses a statistical model to be developed to calculate a temperature index for the QC and patient data populations for the tests selected.
  87c.1. The numerical result of the cumulative index should indicate whether a relationship exists between the tests selected.

c. Clinical Index

The clinical index can differentiate between a test system malfunction and a change in patient population.

88. Feature: The clinical index is based on the clinical inter-relationships between tests.

Note: These relationships exist for patient data.

89. Feature: If the patient data EWMA (or CUSUM) signals an error, the application displays the graph or EWMA (or CUSUM) statistic for all clinically related tests.
 89a. The application is configured to identify clinically related tests.
 89b. If all related tests show a similar change, no error exists. The change is due to a shift in patient population.
 89c. If only the test in question has changed, then analytical error may be present.
 89d. This comparison shall also be available on demand.

d. Analytical Index

The analytical index can identify when a problem may exist with a method or reagent.

90. Feature: The analytical index is based on the analytical or method inter-relationships between tests.

Note: These relationships exist for both patient data and QC data.

91. Feature: If either the patient data or routine QC EWMA (or CUSUM) signals an error, the application displays the graph or CUSUM statistic for all analytically related tests.
 91a. The application is configured to identify analytically related tests.
 91b. This comparison shall also be available on demand.

e. Wavelength Index

The wavelength index focuses on the optical component of a medical device. Since many tests use the same optical filter, grouping tests by wavelength can help identify when an optical system of a medical device is malfunctioning.

92. Feature: All tests are categorized according to the wavelength(s) used during the assay.
 92a. Tests are categorized according to specific single or dual wavelengths.

93. Feature: The current EWMA graph or CUSUM statistic is displayed for all tests with the same wavelength when an error flag occurs or on demand for comparison purposes.

f. Reagent Dispense Index

The relationship between the number of reagents used in the assay may be used to indicate when problems occur with the dispensing system.

94. Feature: All tests are categorized according to the number of reagents used during the assay.

95. Feature: The current EWMA graph or CUSUM statistic is displayed for all tests with the same number of reagents when an error flag occurs or on demand for comparison purposes.

g. Point of Care (POCT) Index

The POCT index is used to monitor the reliability of POCT results.

96. Feature: The application calculates for all tests performed outside the main lab (POCT) a daily, weekly, monthly and annual mean, median, and standard deviation for the patient data population generated by POCT.

97. Feature: For the same tests, the application calculates a daily, weekly, monthly, and annual mean, median and standard deviation of the patient data population generated by the main laboratory.

98. Feature: A simple ratio is calculated by dividing the POCT statistics by the main laboratory statistics.
 98a. Values of 1.0 or less indicate a good comparison. Values over 1.0 would indicate varying levels of non-conformity or disagreement between POCT testing and the main laboratory.

3. Corrective Action

99. Feature: A log of corrective actions is kept for each instrument/test. The log reports the action taken in code format. When the cursor is placed over the code, a description of the action is provided. The table also reports the corrective action date, time and operator.

100. Feature: The application provides a library of action logs as well as free text entry for documenting corrective action.

101. Feature: The laboratory may modify the action log library.

4. Confirmation Testing

Confirmation testing validates successful process correction.

102. Feature: The scope and character of confirmation testing is test dependent. A statistical model (e.g., implemented by confirmation testing module 46) is used to determine the number and concentration of materials to be tested.

102a. The application provides a table that lists QC results from confirmation testing, whether these results are within +/−1 $k_s$, and an area for the test operator to document action taken. This table becomes a record kept for two years or according to user requirements. It is time and date stamped and includes operator initials and final review by a second individual if required by laboratory policy.

102b. The QC data collected as a result of confirmation testing should not be included in the routine QC database. These data are used solely for validation of process correction.

102c. Confirmation testing is successful if all values are within prescribed limits.

102d. When confirmation testing is complete, the application provides the operator a Disposition Record having two choices:
Overall process is within acceptable limits
Overall process is unacceptable 102e. If a mean/standard deviation rule violation occurs during confirmation testing, the operator should indicate that the process is unacceptable. Troubleshooting and the confirmation sequence are repeated. The Disposition Record for repeat confirmation testing is linked to all previous records for the particular event.

H. Charts and Graphs and Tables

The following specifications apply to each test on the system. All charts, graphs and tables are made available for troubleshooting.

103. Feature: The application provides the statistics, tables and graphs described in the Operation section of this document.

103a. Data mining is available to the user. Users are able to create special tables, charts and reports to meet specific needs.

104. Feature: The central application creates, for example, a monthly and quarterly interlaboratory report. This report may include:
calibration frequency
mean and median number of days and patient samples between calibrations
mean and median number of days and patient samples between calibrations for each calibrator lot, reagent lot and calibrator-reagent lot combination.
mean and median number of days and patient samples between actionable errors
mean and median number of days and patient samples between actionable errors for each calibrator lot, reagent lot and calibrator-reagent lot combination.
This information is maintained for two years or according to user requirements.

105. Feature: The user is able to print any chart, graph or table or range of charts, graphs and tables on demand.

105a. For comparative purposes, the application allows the user to specify a specific time range to be applied to any table, chart or graph offered by the system.

106. Feature: For comparative purposes, the application provides the ability to create all charts, graphs, and tables with data derived from two instruments regardless of manufacture.

107. Feature: The application maintains a rolling 7-day (7D), 30-day (30D), six months and lot to date (LTD) mean, median, standard deviation and coefficient of variation for each level of control in tabular format.

108. Feature: For each test, a standard Levey-Jennings chart is provided for plotting routine QC. The scale is +/−3s but shall also allow for display and graphing of the +/−1$k_s$ rule limit. Scaling and display is as with Unity application. Calibration, maintenance and reagent lot changes is illustrated on the chart.

109. Feature: The application calculates and plots the z-score for each QC value within each level of control on a normalized Levey Jennings plot based on peer, method and all instrument group data. Calibration, maintenance and reagent changes are illustrated on the plot.

109a For each test, the application provides a normalized plot of QC values for each level of control. z-scores are calculated from a target mean and standard deviation (peer, method and all instrument). Multiple graphs are available-one for each level of control and one graph with z-scores for all levels plotted. Calibration, maintenance and reagent lot change are illustrated on the chart.

110. Feature: Bias for each analyte relative to peer, method and all instrument groups is expressed as a percent and as a measurable quantity in tabular format and plotted on a standard bias plot. Calibration maintenance and reagent changes are illustrated on the plot.

110a. Daily updates of the peer, method and all instrument groups are internet available. Daily comparisons are based on a 7-day window.

110b. Since every result produced by an instrument, kit or method includes the absolute true value plus some component of true or relative bias and random error, the application calculates for each level of control either relative bias or true bias for each test. Relative bias is calculated by subtracting the observed value or mean from peer, method or all instrument consensus values. Bias is calculated by subtracting the observed value or mean from a reference value. The application provides a mechanism for entering reference values to estimate bias. The application provides a scrollable standard bias plot for each level of control and one plot for all levels of control. The application provides a mechanism for entering consensus values to calculate relative bias. The application provides a scrollable standard bias plot for each level of control and one plot for all levels of control based on relative bias.

111. Feature: The system provides data mining capabilities so labs can segment and analyze control data and patient data based on laboratory interest or need.

112. Feature: Maintenance, calibration, and reagent lot change are illustrated on EWMA (or CUSUM) charts, normalized plots of z-scores and bias plots.

113. Feature: The user is able to capture an image of a chart, graph or table to attach to an email.

114. Feature: The central application preferably has electronic access to all system tables locally held in the laboratory. Access includes the ability to manipulate but not change data and to make system adjustments remotely.

114a. If the laboratory restricts access then a mechanism is available in the application for laboratory personnel to move selected data to a secure area and then send this data to the central application or allow access to this secure area.

114b. The application shall notify laboratory staff at regularly scheduled intervals to prepare data for access.

114c. The application should comply with all HIPPA requirements.

115. Feature: The application provides a normalized plot for the daily mean z-score of patient test results passed by the baseline population truncation screen for each test. z-scores are calculated using the current baseline population mean and standard deviation.

116. Feature: The application provides a normalized plot for the standard deviation z-score of the daily patient test results passed by the baseline population truncation screen for each test. z-scores are calculated using the current baseline population standard deviation.

117. Feature: For each test, the application maintains a daily mean and standard deviation for each time interval of patient data successfully screened by the preset time-interval truncation limits. This data is not used for EWMA (or CUSUM).

118. Feature: For each test, the application calculates a 95% Confidence Interval for the mean of the time interval baseline. The application calculates a 95% Confidence Interval for each daily, weekly and 6-month time interval mean for comparison.

119. Feature: For each test, the application provides a floating three month window Youden plot for routine QC. The user is able to pair specific levels for tri-level controls.

120. Feature: For each test, the application provides floating three month window Youden plot of paired daily peer-base, method-based, and all instrument z-scores for the routine daily QC mean.

121. Feature: For each test, the application provides a floating three month window Youden plot of paired z-scores calculated for daily routine QC precision (normal QC only) and daily variance of the patient data within the normal range that passed screening.

121a. If QC is not run for the day or no patients test results were processed for the day then no plot is performed for the day.

122. Feature: The application plots a frequency histogram of daily patient values over the reportable range that successfully passed baseline population truncation screening overlaid onto the frequency histogram of the reference baseline population for each test.

123. Feature: The application provides a floating twelve week frequency histogram of routine QC values for each level of control including a percentile distribution.

124. Feature: The application provides a floating twelve week frequency histogram of the baseline population patient test results including a percentile distribution.

125. Feature: The application provides an operator activity record for laboratory management that shall document and time stamp the involvement of each test operator for such activities as:
    calibrations
    reagent changes
    error flags
    performance of confirmation testing
    documentation of corrective action
    number of samples repeated due to tests rejected by the operator Statistical Characterizations 126. Feature: The application is configured to generate statistical characterizations including, for example:
    inter-laboratory mean and median time and patient samples between failures and warnings for all calibrator lots by manufacturer.
    inter-laboratory mean and median time and patient samples between failures and warnings for all reagent lots by manufacturer
    inter-laboratory mean and median time and patient samples between failures and warnings for all calibrator-reagent lot combinations by manufacturer
    inter-laboratory total, mean and median number of days and patient samples between calibrator lots
    inter-laboratory total, mean and median number of days and patient samples between reagent lots
    inter-laboratory total, mean and median number of days and patient samples between calibrator-reagent lot combinations
    immediate identification of where specific lots of calibrators and reagents are in use
    inter-laboratory frequency of calibration by instrument platform for each test
    inter-laboratory imprecision of instrument platforms by test and method over time based on patient data
    imprecision of instrument platforms by test and method over time based on control data
    inter-laboratory characterization of patient data for each test by gender and age
    inter-laboratory characterization of patient data for each test by known disease state
    a ranking of instruments and methods by performance scores using precision, bias, and frequency of actionable error in a model to be developed.

127. Feature: All of the above characterizations are available by postal/zip code, state/province, region, or country.

APPENDIX B

Glossary

General Definitions $1-p_{ed}$: The probability of failing to detect an error condition. See $p_{ed}$.

Actionable errors (test system failures): a 1ks rule violation during routine QC or an in excess of limit signal sent from the patient-based EWMA (or CUSUM) model that is supported by the routine QC EWMA (or CUSUM) model.

Analysis: Determining the measure of a substance contained in a patient sample: testing.

Analyte: A single constituent of a human matrix such as serum or urine; test.

Analytical process: The steps involved in performing an assay on a sample of, e.g., human serum, plasma, whole blood, urine, spinal fluid, etc.

AON: Average of Normals.

ARL: Average Run Length; average length of a run in terms of QC values, patient test results or time before a statistical model issues a warning or signal.

avg(hrwk): The average of the results within the window for hour, hrwk.

Bad result: A result with an error condition that exceed the total allowable error specification ($TE_a$). The probability of a bad result depends on the magnitude of the out-of-control error condition (SE, RE) and on the total allowable error specification.

Baseline population: A truncated population of patient data that includes all time intervals and all days of the week. It is less definitive than the time-interval baseline.

Baseline, time-interval: A truncated population of patient data for a specific time period and day of the week or month.

Bias: The quantifiable difference between an observed value and a value obtained by a reference method. The systematic signed deviation of the test results from the accepted reference value. The difference between the expectation of the test results and an accepted reference value.

Bias, relative: The quantifiable difference between an observed value and a value obtained by some consensus method; use of peer group consensus data as the point of measure; not a true bias.

Biometric model: The application and mathematical algorithms that underlie the Biometric QC processes.

Biometric QC: A process based on traditional QC and biology for monitoring the analytical processes in use by a clinical diagnostic laboratory.

CEN: Committee for European Normalization; standards setting body for the European Community; divided into Technical Committees that develop standards and requirements CEN/TC 251: A CEN Technical Committee developing standards for Healthcare/Medical Informatics; parallel committee is ISO TC 251

CEN/TC 212: A CEN Technical Committee developing standards for Laboratory Quality; parallel committee is ISO TC 212

Change Event: See Event.

CLIA: Clinical Laboratory Improvement Act.

Coefficient of variation ratio: The ratio of the laboratory coefficient of variation for a particular test to the peer coefficient of variation for the same test and time period.

Confirmation testing: A modeled process used to confirm that the analytical process is operating within specifications.

CUSUM: Cumulative Sums; a statistical model used to detect shifts and trends in the data.

CUSUM for Variance (CUSUM-S): A statistical model used to detect shifts and trends in the imprecision of data sets.

De-identify: To strip data of all references that could make the data traceable to the patient from which they were derived.

dpE: Probability of producing a bad result due to an out-of-control error condition.

Error flag: A signal to the operator that the analytical process is not operating within specifications.

Event: Any event that has the potential to affect the analytical process subsequent to the event. Change Events include calibration, change of reagent lot, any instrument maintenance (other than daily), a notified change in a test system such as new antibody or reagent reformulation, a change in the operator for technique sensitive tests, corrective actions taken after either a routine QC failure or a patient-based QC failure, etc.

Event-based QC: QC sample testing that is triggered by a change event.

EWMA: Exponentially weighted moving average: an accepted statistical model used to monitor time-series data; a statistical model used to detect shifts and trends in performance using means or variance derived from QC data.

EWMA for variance (EWMA-S): Exponentially Weighted Moving Averages for variance; a statistical model used to detect shifts and trends in performance using variance derived from QC data.

Frequency and character of QC testing: The time of day and day of the week at which certain concentrations of QC are tested.

hrwk: The hour of the week for each result (e.g., hrwk may range from 1 to 168).

ISO: International Organization for Standardization; an international body that sets quality standards; an organization formed to develop and harmonize international standards.

Laboratory utilization: A use pattern that varies by time and day of week and is directly related to the ratio of healthy patients to unhealthy patients.

LAN: Local Area Network.

LIS: Laboratory Information System.

med: The middle value of a set of scores.

N: Number of QC samples.

Normalized: see z-score.

Nres: Total number of patient results.

Nresout: The number of results that are <tlo or >thi

Nresin(hrwk): The number of results used in the calculations for hour, hrwk.

Nreslo: The number of results that equal tlo.

Nresthi: The number of results that equal thi.

Patient data: Result(s) derived from laboratory analysis of, e.g., human serum, plasma, whole blood, urine, spinal fluid, etc.: test result.

Patient sample: A quantity of human serum, plasma, whole blood, urine, spinal fluid, etc. collected from an individual.

pctresout: Percentage of results outside truncation limits, where pctresout=Nresout/Nres.

pctout: The target percent of results to truncate.

PDA: Personal Digital Assistant.

$p_{ed}$: Probability of error detection. See $1-p_{ed}$.

$p_{fr}$: False rejection rate pQE: The probability of producing "bad" results when using a specific QC rule after an event. The pQE is generally equal to the increase in the probability of producing "bad" results because of the error condition times the probability of failing to detect the error condition. $pQE=dpE*(1-p_{ed})$.

QC: Quality control.

Quality Control (QC) materials: For example, lyophilized or frozen materials with a known range of values that are designed to mimic a patient sample. After being reconstituted, e.g., with water or thawed, the materials are tested alongside patient samples.

Random error (RE): Statistical error that is inherent in every test method. It is expressed as imprecision. External factors can cause an increase in random error beyond what is expected and this error must be detected and controlled by the laboratory.

RE: Stable analytic imprecision. See random error.

RiliBAK rules: Statistical process control scheme required for German laboratories Risk: The potential number of patient test results containing unacceptable error; expressed as a part of a whole, e.g., 1/10,000 or 1/1,000,000.

Routine QC: Testing of quality control materials of varying levels of concentration at specified times on specified days.

resin: A collection of patient results that are within truncation limits.

SD Standard Deviation, calculated as:

$$SD = \sqrt{\frac{\sum (x^2) - \frac{(\sum x)^2}{n}}{n-1}}.$$

SDres: The standard deviation of all results.

SDBresin(hrwk): The week-to-week (between-week) standard deviation of patient results within truncation limits for hour hrwk.

SDrestlo: The standard deviation of the results that are >tlo and ≤thi (excludes results that equal tlo).

SDTresin(hrwk): The total standard deviation of patient results within truncation limits for hour hrwk.

SDresthi: The standard deviation of the results that are ≧tlo and <thi (excludes results that equal thi).

SDWresin(hrwk): The within-week standard deviation of patient results within truncation limits for hour hrwk.

SE: A shift from the target (i.e., correct value). See systematic error.

Special processing day: A regular day of the week or month when the laboratory processes samples from a medically defined group of patients such as, for example, end stage renal disease patients or cancer patients.

Statistical process control: A set of statistical rules, used singly or in combination, with theoretical power to detect undesired changes in the expected value or precision of patient results produced by the analytical process.

Surface plot: A chart used to find optimum combinations between two sets of data. As in a topographic map, colors and patterns indicate areas that are in the same range of values.

Systematic error (SE): A change in the analytical process that can be sudden in onset and that produces a constant measurement error in subsequent results; bias.

tlo: The lower truncation limit.

thi: The upper truncation limit.

$TE_a$: The total allowable error specification.

Test result: See patient data.

Test/Testing: Determining the measure of a substance contained in a patient sample: analysis.

Total error allowable (patient data): 1.65 times the biological imprecision plus the biological bias for 95% confidence or 2.33 times the biological imprecision plus the biological bias for 99% confidence. The biological bias is defined as 0.25 times the square root of the sum of the squares of the between patient CV and the within patient sample CV. The biological imprecision is defined as 0.5 time the within patient CV.

Total error allowable (QC): Twice the imprecision of the peer group or method group. This definition assumes bias is zero for the peer group and method group.

Truncation: The lopping off of either high or low (or both) patient results by simulation; truncation is test specific and often asymmetric; the exclusion of high or low (or both) values from inclusion in the main population of data.

Truncation limits: A positive and/or negative endpoint (or threshold) at which certain data points within a population of data are excluded.

ures: The collection of unique patient values.

WAN: Wide Area Network.

Warning(s): An in excess of limit signal sent by the EWMA (or CUSUM) QC model not supported by the EWMA (or CUSUM) patient data model, or an in excess of limit signal sent by the EWMA-S (or CUSUM-S) model that does not agree with the EWMA (or CUSUM) model for patient data, or for either patient or routine QC data.

whlfwdth: The half-width of the moving window (in hours) used to calculate the hour of the week means and standard deviations.

wkn: The week number of the result (e.g., if there are 13 weeks of data in resin then wkn ranges from 1 to 13).

$\bar{X}/S$ rule: The mean/range rule, a preferred QC rule for testing a single group of QC samples. Also referred to as the Xbar/S rule.

Z-score: Transforming a measured result by subtracting the expected value of the result and then dividing by the standard deviation of the result; a normalized statistic. The number of standard deviations that a value is above or below the mean.

What is claimed and desired to be secured by Letters Patent is as follows:

1. A computer-implemented method of determining a bracketed quality control testing strategy on patient test data, comprising;
    acquiring patient test data from one or more laboratory instruments;
    determining an average run length, using the computer, having a desired number of unacceptable errors reported for a selected QC Rule;
    calculating an optimum frequency of testing control samples, using the computer, to achieve a desired number of unacceptable results; and
    testing the strategy on said patient data.

2. The method of claim 1, wherein the desired number of unacceptable results reported has a value less than 1.

3. The method of claim 2, wherein said value is greater than 0.90.

4. The method of claim 3, wherein said value approaches 1.

5. The method of claim 1, further comprising calculating a number of unacceptable results reported for a selected frequency of testing control samples.

6. A computer-implemented method of implementing a bracketed quality control testing strategy on patient data, comprising;
    acquiring patient data from one or more laboratory instruments;
    selecting a QC Rule;
    for the selected QC Rule, calculating an average run length, using the computer, before an unacceptable error is reported;
    selecting a number of unacceptable errors reported for the selected QC Rule;
    calculating an optimum frequency of testing control samples, using the computer, to achieve the selected number of unacceptable results reported; and
    applying the strategy to said patient data.

7. The method of claim 6, wherein the desired number of unacceptable results reported has a value less than 1.

8. The method of claim 7, wherein said value is greater than 0.90.

9. The method of claim 8, wherein said value approaches 1.

10. The method of claim 6, further comprising:
    selecting a frequency of testing control samples; and
    calculating a number of unacceptable results reported for the selected frequency of testing control samples.

11. A computer-implemented method of determining a bracketed quality control testing strategy on patient test data, comprising:
    acquiring patient test data from one or more laboratory instruments;
    determining an average run length, using the computer, having a desired number of unacceptable errors reported for a selected QC Rule;
    calculating an optimum frequency of testing control samples, using the computer, to achieve a desired number of unacceptable results;
    testing the strategy on said patient data by testing said control samples at the optimum frequency; and
    providing an alert if one of the tested control samples exceeds an established quality control limit for the selected QC Rule.

12. The method of claim 11, wherein the desired number of unacceptable results reported has a value less than 1.

13. The method of claim 12, wherein said value is greater than 0.90.

14. The method of claim 13, wherein said value approaches 1.

15. The method of claim 11, further comprising calculating a number of unacceptable results reported for a selected frequency of testing control samples.

* * * * *